United States Patent
Lan et al.

(10) Patent No.: US 11,613,552 B2
(45) Date of Patent: *Mar. 28, 2023

(54) PHARMACEUTICAL AGENTS, COMPOSITIONS, AND METHODS RELATING THERETO

(71) Applicant: Alltech, Inc., Nicholasville, KY (US)

(72) Inventors: Zi-Jian Lan, Lexington, KY (US); Ronan Power, Lexington, KY (US); Alexandros Yiannikouris, Lexington, KY (US); Thirupathi Reddy Yerramreddy, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/238,354

(22) Filed: Apr. 23, 2021

(65) Prior Publication Data

US 2021/0238216 A1 Aug. 5, 2021

Related U.S. Application Data

(63) Continuation of application No. 16/490,836, filed as application No. PCT/US2018/030371 on May 1, 2018, now Pat. No. 11,014,954.

(60) Provisional application No. 62/508,730, filed on May 19, 2017.

(51) Int. Cl.
*A61K 31/7076* (2006.01)
*C07H 19/16* (2006.01)
*A61P 3/10* (2006.01)
*C07H 19/167* (2006.01)

(52) U.S. Cl.
CPC .......... *C07H 19/16* (2013.01); *A61K 31/7076* (2013.01); *A61P 3/10* (2018.01); *C07H 19/167* (2013.01)

(58) Field of Classification Search
None
See application file for complete search history.

(56) References Cited

U.S. PATENT DOCUMENTS

| | | |
|---|---|---|
| 8,796,241 B2 | 8/2014 | Lubin et al. |
| 9,642,874 B2 | 5/2017 | Power et al. |
| 9,833,486 B2 | 12/2017 | Power et al. |
| 10,201,558 B2 | 2/2019 | Power et al. |
| 10,201,559 B2 | 2/2019 | Power et al. |
| 11,014,954 B2 * | 5/2021 | Lan .................. C07H 19/16 |
| 2003/0055016 A1 * | 3/2003 | Huang ................. C07H 5/08 544/243 |
| 2006/0093684 A1 | 5/2006 | Takeda et al. |
| 2006/0198906 A1 | 9/2006 | Majeed et al. |
| 2007/0077238 A1 | 4/2007 | Teo et al. |
| 2009/0137520 A1 | 5/2009 | Elzein et al. |
| 2012/0094947 A1 | 4/2012 | Lubin et al. |
| 2016/0045533 A1 * | 2/2016 | Power ..................... A61P 3/08 514/46 |
| 2016/0082033 A1 | 3/2016 | Power et al. |
| 2016/0090397 A1 | 3/2016 | Zhou et al. |
| 2020/0123191 A1 | 4/2020 | Lan et al. |

FOREIGN PATENT DOCUMENTS

| | | |
|---|---|---|
| EP | 3144001 A1 | 3/2017 |
| RU | 2298557 C2 | 10/2007 |
| WO | WO-03/014137 | 2/2003 |
| WO | WO-2013/151975 A1 | 10/2013 |
| WO | WO-2014/144776 A1 | 9/2014 |
| WO | WO-2015/137983 A1 | 9/2015 |
| WO | WO-2017/048253 A1 | 3/2017 |
| WO | WO-2018/212980 A1 | 11/2018 |

OTHER PUBLICATIONS

Wolff, Manfred E. "Burger's Medicinal Chemistry, 5ed, Part I", John Wiley & Sons, 1995, pp. 975-977 (Year: 1995).*
Banker, G.S. et al, "Modern Pharmaceutics, 3ed.", Marcel Dekker, New York, 1996, p. 596 (Year: 1996).*
Arnaudguilhem, C. et al., Selenium metabolomics in yeast using complementary reversed-phase/hydrophilic ion interaction (HILIC) liquid chromatography-electrospray hybrid quadrupole trap/Orbitrap mass spectrometry, Anal. Chim. Acta., 757:26-38 (2012).
Ashton, T.D. et al., N6-substituted C5'-modified adenosines as A1 adenosine receptor agonists, Bioorg. Med. Chem., 16(4):1861-73 (2008).
Banker, G. and Rhodes, C., Modern Pharmaceutics, 3rd Edition, Marcel Dekker, New York, p. 596 (1996).
Bierla, K. et al., Comprehensive speciation of selenium in selenium-rich yeast, Trends in Anal. Chem., 41:122-132 (2012).
Bothwell, I. R. et al., Large-Scale, Protection-Free Synthesis of Se-Adenosyl-L-selenomethionine Analogues and Their Application as Cofactor Surrogates of Methyltransferases, Org. Lett., 16(11):3056-3059 (2014).
Candow, D. and Chilibeck, P., Differences in size, strength, and power of upper and lower body muscle groups in young and older men, J Gerontol A Biol Sci Med Sci., 60(2):148-56 (2005).
Carrasco, N. et al., Synthesis of Selenium-Derivatized Nucleosides and Oligonucleotides for X-Ray Crystallography, Nucleosides, Nucleotides & Nucleic Acids, 20(9):1723-34 (2001).
Clee, S. et al., Positional cloning of Sorcs1, a type 2 diabetes quantitative trait locus, Nat Genet, 38(6):688-93 (2006).
Coleman, D.L., Obese and diabetes: two mutant genes causing diabetes-obesity syndromes in mice, Diabetologia, 14(3):141-8 (1978).
De Felice, F. et al., How does brain insulin resistance develop in Alzheimer's disease?, Alzheimer's & Dementia, 10(1S):S26-32 (2014).
Duclos, R.I. et al., Synthesis and characterization of Se-adenosyl-L-selenohomocysteine selenoxide, J. Sulphur Chem., 36(2):135-144 (2015).
Glass, D. and Roubenoff, R., Recent advances in the biology and therapy of muscle wasting, Ann N Y Acad Sci.,1211:25-36 (2010).

(Continued)

*Primary Examiner* — Traviss C McIntosh, III
(74) *Attorney, Agent, or Firm* — Choate, Hall & Stewart LLP; John P. Rearick; Brennan A. Murphy

(57) ABSTRACT

The present disclosure provides compounds of formulas (1)-(3), and compositions and methods of use thereof. The present disclosure also provides methods of preparing a provided compound and composition, and methods of characterizing a provided compound and composition.

31 Claims, 31 Drawing Sheets

(56) References Cited

OTHER PUBLICATIONS

Hardie, D.G., Metformin-acting through cyclic AMP as well as AMP?, Cell Metab, 17(3):313-4 (2013).
International Search Report for PCT/US2018/30371 (Pharmaceutical Agents, Compositions, and Methods Relating Thereto, filed May 1, 2018), issued by ISA/US, 3 pages (Aug. 10, 2018).
Kogami, M. et al., An efficient method for the synthesis of selenium modified nucleosides: its application in the synthesis of Se-adenosyl-L-selenomethionine (SeAM), Org. Biomol. Chem., 13(36):9405-9417 (2015).
Lan, Z. et al., GCNF-dependent repression of BMP-15 and GDF-9 mediates gamete regulation of female fertility, EMBO J, 22(16):4070-81 (2003).
Lan, Z. et al., Non-peptidyl small molecule, adenosine, 5'-Se-methyl-5'-seleno-, 2',3'-diacetate, activates insulin receptor and attenuates hyperglycemia in type 2 diabetic Lepr$^{db/db}$ mice, Cellular and and Molecular Life Sciences, 77:1623-1643 (2020).
Li, Z. et al., Reduced white fat mass in adult mice bearing a truncated Patched 1, Int J Biol Sci., 4(1):29-36 (2008).
Ouerdane, L. et al., Comprehensive speciation of low-molecular weight selenium metabolites in mustard seeds using HPLC-electrospray linear trap/Orbitrap tandem mass spectrometry, Metallomics, 5(9):1294-1304 (2013).
Preud'Homme, H. et al., Large-scale identification of selenium metabolites by online size-exclusion-reversed phase iquid chromatography with combined inductively coupled plasma (ICP-MS) and electrospray ionization linear trap-Orbitrap mass spectrometry (ESI-MS(n)), Metallomics, 4(5):422-432 (2012).
Reddy, P. et al., Oocyte-specific deletion of Pten causes premature activation of the primordial follicle pool, Science, 319(5863):611-3 (2008).
Ryall, J. et al., Cellular and molecular mechanisms underlying age-related skeletal muscle wasting and weakness, Biogerontology, 9(4):213-28 (2008).
Sakuma, K. and Yamaguchi, A., Novel intriguing strategies attenuating to sarcopenia, J. Aging Res., 2012:251217, 11 pages (2012).
SciFinder, Kogami_2015_Org_Bio_Chem_Structures, ACS, 2015, structure 31, 1805788-83-3, 8 pages.
Singh, S., et al., Facile Chemoenzymatic Strategies for the Synthesis and Utilization of S-Adenosyl-(L)-Methionine Analogues, Angew. Chem. Int. Ed., 53(15):3965-3969 (2014).
White, M. F., Insulin signaling in health and disease, Science, 302(5651):1710-1 (2003).
Wolff, Manfred E., Burger's Medicinal Chemistry and Drug Discovery, 5th Edition, Part I, John Wiley & Sons, 975-977 (1995).
Written Opinion for PCT/US2018/30371 (Pharmaceutical Agents, Compositions, and Methods Relating Thereto, filed May 1, 2018), issued by ISA/US, 5 pages (Aug. 10, 2018).
Belikov, V. G., Pharmaceutical Chemistry, Moscow "MEDpress-inform," 4 pages (2007).
Dyson, T. and May, L., Chemistry Synthetic Medicinal Substances, 9 pages (Moscow 1964).
Smirnova, I.G. et al., Optical Isomery and Biological Activity of Drugs, Bulletin of the Moscow University, Series 2, Chemistry, 53(3):147-156 (2012).
Zhulenko, V.N. and Gorshkov, G.I., Pharmacology, Textbooks and Manuals for Higher Education Students, 3 pages (2008).

* cited by examiner

D

E

F

PHARMACEUTICAL AGENTS, COMPOSITIONS, AND METHODS RELATING THERETO

PRIORITY CLAIM

This application is a continuation of U.S. patent application Ser. No. 16/490,836, filed Sep. 3, 2019 (now U.S. Pat. No. 11,014,954), which is a U.S. National Stage Application of International Patent Application No. PCT/US2018/030371, filed May 1, 2018, which claims priority to U.S. Provisional Patent Application Ser. No. 62/508,730, filed May 19, 2017. The entire content of each application is incorporated herein by reference.

BACKGROUND

Diabetes is a group of metabolic diseases in which there are high blood sugar levels over a prolonged period. There are various types of diabetes. Type I diabetes results from the pancreas's failure to produce enough insulin. Type II diabetes begins with insulin resistance, a condition in which cells fail to respond to insulin properly, and may cause a lack of insulin as the disease progresses. There are about 400 million diabetes patients worldwide, with type II diabetes making up about 90% of the cases. Insulin, or insulin analogs, are generally used for treating type I diabetes. Metformin is generally recommended as a first line treatment for type II diabetes.

SUMMARY

Prior work (see WO2015/137983, US2016/0045533 (issued at U.S. Pat. No. 9,642,874), and US2016/0082033, each of which is incorporated herein by reference) has defined certain selenoorganic compounds that show interesting and valuable activity in certain disease model systems. Specifically, this work has defined compounds of formulas I, II, and III, depicted below:

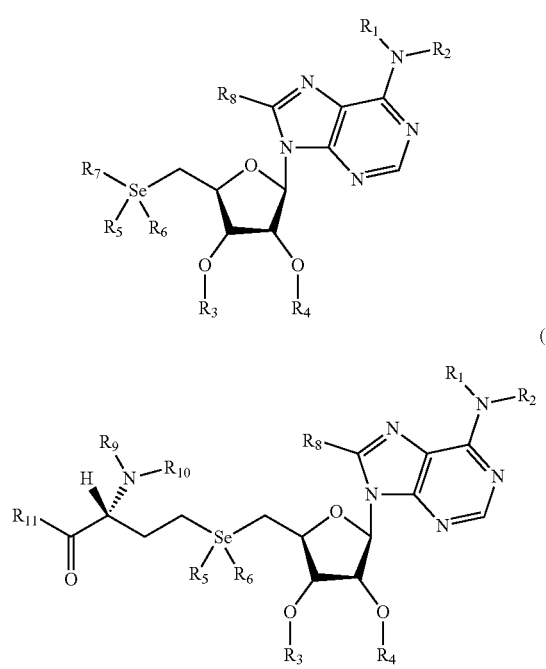

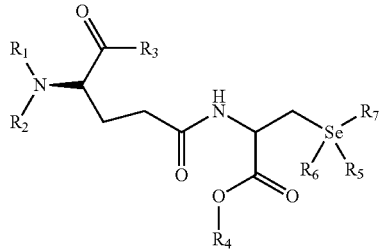

for which it reports that:
1. A combination of the following three compounds: 5'-Methylselenoadenosine (compound C, which is a compound of formula I), Se-Adenosyl-L-homocysteine (compound D, which is a compound of formula II), and Gamma-glutamyl-methylseleno-cysteine (Compound E, which is a compound of formula III),

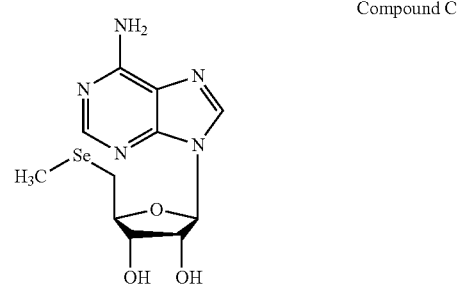

Compound C

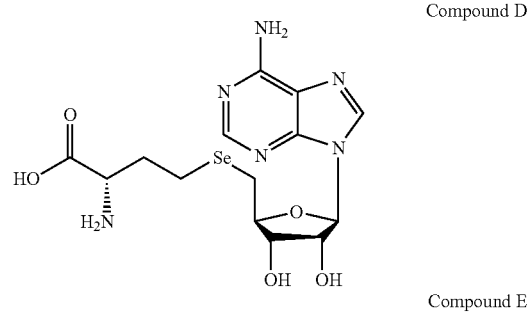

Compound D

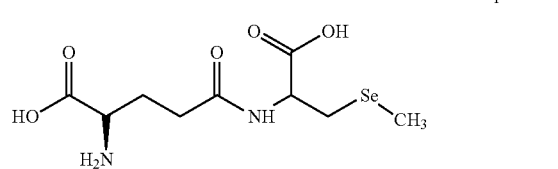

Compound E but not the individual compounds, can significantly attenuate G6pc expression, thereby representing a novel way to reduce hepatic glucose output (See, WO2015/137983);
2. Compounds C and D each individually can enhance mitochondrial (MT) potential in mouse skeletal muscle myoblast C2C12 cells, which suggests that compounds C and D can be potentially useful in the area of T2DM research and control (See, WO2015/137983);
3. A combination of compounds C, D and E can reduce hepatic glucose output and improve glucose tolerance in an insulin-resistant, diabetic mouse model, so that a combination of compounds C, D and E can be useful in treatment of obesity, hyperglycemia, and diabetes (See, US20160045533);
4. Compounds C and D may be useful in treating sarcopenia caused by progressive loss of MT function in the kidney or skeletal muscle (See, WO2015/137983);

5. Compound C can enhance gluconeogenesis in brain cells which may be beneficial for the survival of brain cells in AD (See, US20160082033); and
6. Compounds C and D can inhibit Tau hyperphosphorylation in AD brains (See, US20160082033).

Thus, prior work demonstrates that compounds C, D, and E may be useful in certain contexts; specifically teaching that, in some contexts (e.g., inhibiting Tau hyperphosphorylation in AD brains, and enhancing gluconeogenesis in brain cells), compound C or compound D might be useful alone. In other contexts (e.g., reducing hepatic glucose output, improving glucose tolerance and/or otherwise effectively treating obesity, hyperglycemia, and/or diabetes), these compounds are shown not to be useful individually, but to be effective in combination.

The present disclosure provides new selenium-containing compounds, sharing some structural relationship with compounds of formulas I and II above (and specifically with compounds C and D), that surprisingly show potent activity alone in a variety of contexts.

The present disclosure demonstrates, among other things, that provided compounds exhibit bioactivity comparable to or better than the CDE combination in reducing hepatic glucose output and/or improving glucose tolerance in insulin-resistant, diabetic subjects. The present disclosure also teaches that provided compounds likely have bioactivity comparable to or better than Compounds C and/or D in enhancing gluconeogenesis (e.g., in brain cells), and/or in inhibiting Tau hyperphosphorylation (e.g., in AD brains).

The present disclosure provides compositions that contain and/or deliver such compounds (and/or one or more degradants and/or active metabolites thereof), as well as various methods (e.g., of manufacture, characterization, and/or use) and/or materials (e.g., intermediates, degradants, metabolites [in particular, active metabolites], etc) related to such provided compounds. In some embodiments, provided technologies relate to and/or are particularly useful in modulating glucose metabolism; enhancing AS160 phosphorylation for translocation of glucose transporter proteins (GLUTs) from cytosolic vesicles to plasma membrane for glucose uptake; and/or enhancing glucose uptake in both liver and skeletal muscles. In some embodiments, provided technologies relate to and/or are particularly useful in treatment of hyperinsulinemia, obesity, diabetes, hyperglycemia, polycystic ovary syndrome (PCOS), Alzheimer's disease (AD), and/or sarcopenia. In some embodiments, provided technologies relate to and/or are particularly useful in treatment of type II diabetes related disorders, such as diabetic retinopathy, nephropathy, neuropathy, and vascular disorders.

In some embodiments, the present disclosure provides a compound of formula (1):

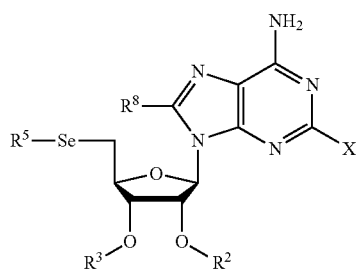

or a pharmaceutically acceptable salt, prodrug, or isomer thereof, wherein each of $R^2$ and $R^3$ is independently H or —C(O)—R, wherein each R is independently $C_{1-6}$alkyl or 3-8 membered carbocyclic or heterocyclic, wherein $R^2$ and $R^3$ cannot be both H;

or $R^2$ together with $R^3$ form —(CH$_2$)$_n$—C(O)—(CH$_2$)$_m$—, wherein each of n and m is independently 0-3, and n+m≤3;

$R^5$ is —$C_{1-6}$alkyl or —$C_{1-6}$alkyl-CH(NH$_2$)COOH;

$R^8$ is H or halogen; and

X is H or halogen, wherein each of the carbocyclic, heterocyclic, —(CH$_2$)$_n$—, and —(CH$_2$)$_m$— moieties, independently, may optionally be substituted 1-3 times by —OH, halogen, NH$_2$, CN, or $C_{1-6}$alkyl; and each $C_{1-6}$alkyl moiety, independently, may optionally be substituted 1-3 times by —OH, halogen, NH$_2$, or CN.

In some embodiments, the present disclosure provides a compound of formula (2):

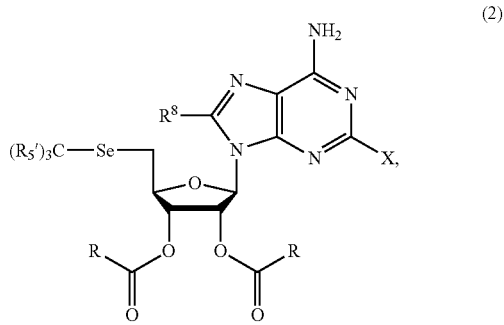

or a pharmaceutically acceptable salt, prodrug, or isomer thereof, wherein $R^8$ is H or halogen;

X is H or halogen;

each $R_5'$ is independently H or halogen; and each R is independently $C_{1-6}$alkyl, each of which, independently, may optionally be substituted 1-3 times by halogen.

In some embodiments, the present disclosure provides a compound of formula (3):

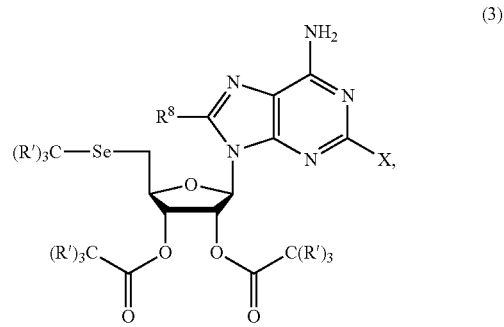

or a pharmaceutically acceptable salt, prodrug, or isomer thereof, wherein $R^8$ is H or halogen;

X is H or halogen; and each R' is independently H or halogen.

In some embodiments, the present disclosure provides compositions which comprise or deliver a compound of any one of formulas (1)-(3). In some embodiments, the present disclosure provides compositions comprising a compound of any one of formulas (1)-(3), or a pharmaceutically acceptable salt, prodrug, or isomer thereof. In some embodiments, the present disclosure provides compositions which deliver an active moiety of a compound of any one of formulas (1)-(3).

In some embodiments, the present disclosure provides methods of treating a disease, disorder, or condition by administering a compound or composition as described herein. In some embodiments, provided methods enhance AS160 phosphorylation for translocation of glucose transporter proteins (GLUTs) from cytosolic vesicles to plasma membrane for glucose uptake. In some embodiments, provided methods enhance glucose uptake in both liver and skeletal muscles. In some embodiments, provided methods attenuate hyperinsulinemia without impairing kidney function and/or resulting in liver damage.

In some embodiments, the present disclosure provides methods for treating an insulin-related disorder, comprising administering a therapeutically effective amount of a compound of any one of formulas (1)-(3), or a pharmaceutically acceptable salt, prodrug, or isomer thereof.

In some embodiments, the present disclosure provides methods for treating insulin resistance disorder comprising administering a therapeutically effective amount of a compound of any one of formulas (1)-(3), or a pharmaceutically acceptable salt, prodrug, or isomer thereof.

In some embodiments, the present disclosure provides methods for treating glucose metabolism disorders, comprising administering a therapeutically effective amount of a compound of any one of formulas (1)-(3), or a pharmaceutically acceptable salt, prodrug, or isomer thereof. In some embodiments, glucose metabolism disorders involve a blood glucose level which is not within the normal range. In some embodiments, glucose metabolism disorders relate to defective glucose uptake and/or transport. In some embodiments, glucose metabolism disorders are Diabetes Mellitus, glyceraldehyde-3-phosphate dehydrogenase deficiency, glycosuria, hyperglycemia, hyperinsulinism, or hypoglycemia.

In some embodiments, the present disclosure provides methods for treating disorders of glucose transport, comprising administering a therapeutically effective amount of a compound of any one of formulas (1)-(3), or a pharmaceutically acceptable salt, prodrug, or isomer thereof. In some embodiments, disorders of glucose transport are glucose-galactose malabsorption, Fanconi-Bickel syndrome, or De Vivo disease (GLUT1 deficiency syndrome (GLUT1DS)).

In some embodiments, the present disclosure provides methods for treating obesity comprising administering a therapeutically effective amount of a compound of any one of formulas (1)-(3), or a pharmaceutically acceptable salt, prodrug, or isomer thereof.

In some embodiments, the present disclosure provides methods for treating diabetes comprising administering a therapeutically effective amount of a compound of any one of formulas (1)-(3), or a pharmaceutically acceptable salt, prodrug, or isomer thereof.

In some embodiments, the present disclosure provides methods for treating hyperglycemia comprising administering a therapeutically effective amount of a compound of any one of formulas (1)-(3), or a pharmaceutically acceptable salt, prodrug, or isomer thereof.

In some embodiments, the present disclosure provides methods for treating polycystic ovary syndrome (PCOS) comprising administering a therapeutically effective amount of a compound of any one of formulas (1)-(3), or a pharmaceutically acceptable salt, prodrug, or isomer thereof.

In some embodiments, the present disclosure provides methods for treating Alzheimer's disease (AD) comprising administering a therapeutically effective amount of a compound of any one of formulas (1)-(3), or a pharmaceutically acceptable salt, prodrug, or isomer thereof.

In some embodiments, the present disclosure provides methods for treating sarcopenia comprising administering a therapeutically effective amount of a compound of any one of formulas (1)-(3), or a pharmaceutically acceptable salt, prodrug, or isomer thereof.

In some embodiments, the present disclosure provides methods for inhibiting glucose production, comprising administering a compound of any one of formulas (1)-(3), or a pharmaceutically acceptable salt, prodrug, or isomer thereof.

In some embodiments, the present disclosure provides methods for increasing glucose tolerance, comprising administering a compound of any one of formulas (1)-(3), or a pharmaceutically acceptable salt, prodrug, or isomer thereof.

In some embodiments, the present disclosure provides methods for activating and/or restoring insulin receptor function and its downstream signaling in a subject in insulin-resistant state, comprising administering a compound of any one of formulas (1)-(3), or a pharmaceutically acceptable salt, prodrug, or isomer thereof.

In some embodiments, the present disclosure provides methods for treating mitochondria-associated diseases (e.g., caused by dysfunctional mitochondria), comprising administering a therapeutically effective amount of a compound of any one of formulas (1)-(3), or a pharmaceutically acceptable salt, prodrug, or isomer thereof. In some embodiments, mitochondria-associated diseases can be degenerative diseases (e.g., cancer, cardiovascular disease and cardiac failure, type 2 diabetes, Alzheimer's and Parkinson's diseases, fatty liver disease, cataracts, osteoporosis, muscle wasting such as sarcopenia, sleep disorders and inflammatory diseases such as psoriasis, arthritis and colitis). In some embodiments, the present disclosure provides methods for enhancing mitochondrial function, comprising administering a therapeutically effective amount of a compound of any one of formulas (1)-(3), or a pharmaceutically acceptable salt, prodrug, or isomer thereof.

In some embodiments, the present disclosure provides methods for enhancing gluconeogenesis in the brain, comprising administering a therapeutically effective amount of a compound of any one of formulas (1)-(3), or a pharmaceutically acceptable salt, prodrug, or isomer thereof. In some embodiments, provided methods increase glucose uptake in the brain. In some embodiments, provided methods are for maintaining or restoring brain functions including memory and learning.

In some embodiments, the present disclosure provides methods for preparing a compound of any one of formulas (1)-(3), or a pharmaceutically acceptable salt, prodrug, or isomer thereof.

In some embodiments, the present disclosure provides methods for characterizing a compound of any one of formulas (1)-(3), or a pharmaceutically acceptable salt, prodrug, or isomer thereof.

In some embodiments, the present disclosure provides methods for preparing a composition as described herein.

In some embodiments, the present disclosure provides methods for characterizing a composition as described herein.

DETAILED DESCRIPTION OF CERTAIN EMBODIMENTS

Definitions

Figure 1:
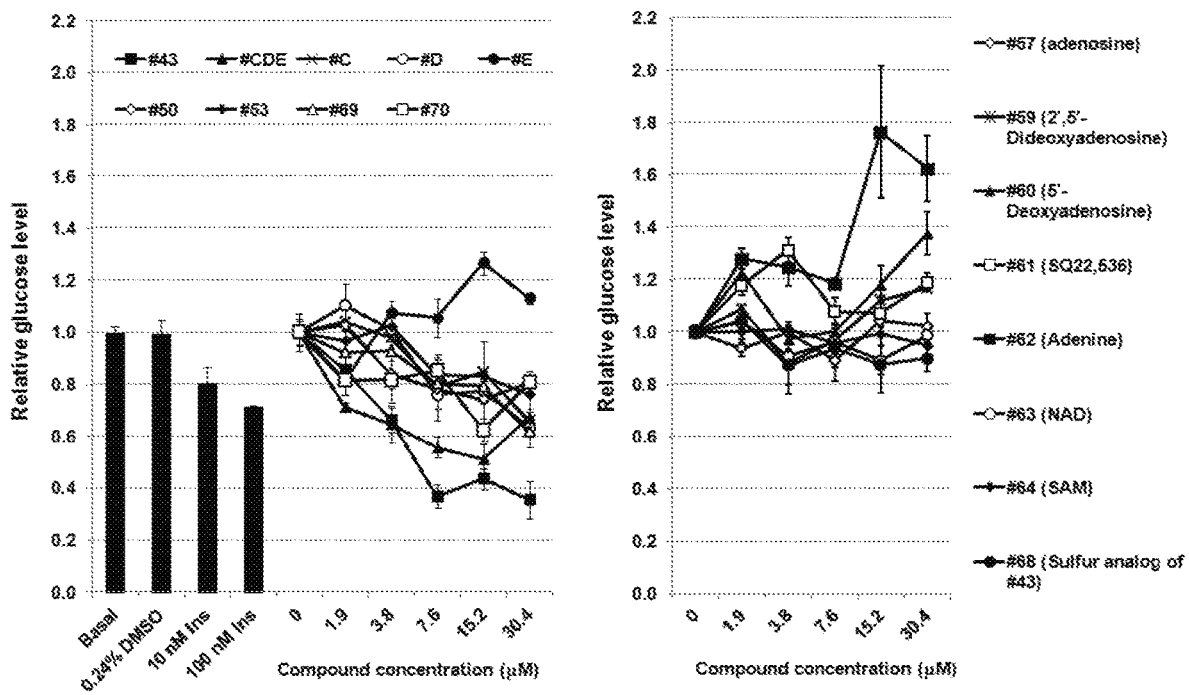
FIG. 1. Effects of insulin and pure compounds (listed in Table 1) on glucose production in HepG2 cells. Cells were treated with 0.24% DMSO (the maximal volume of tested compound solvent), insulin or listed compounds in serum-free glucose production media for 48 hr. Data were normalized by cell number as described above, and presented as mean±SEM of at least 3 samples per group.

Definitions of specific functional groups and chemical terms are described in more detail below. For purposes of this disclosure, chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

The singular forms "a", "an", and "the," as used herein and in the claims, include the plural reference unless the context clearly indicates otherwise. Thus, for example, a reference to "a compound" includes a plurality of such compounds.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Alzheimer's disease: As used herein, the term "Alzheimer's disease", or "AD", refers to a progressive disease of the human central nervous system. Brain insulin signaling is important for learning and memory, and insulin resistance in the brain is a major risk factor for AD. The restoration of insulin signaling has emerged as a potential therapy for AD (White M F, Science 2003; 302:1710-1; De Felice D G et al, Alzheimer's & Dementia 2014; 10: S26-S32). In certain embodiments, it is manifested by dementia typically in the elderly, by disorientation, loss of memory, difficulty with language, calculation, or visual-spatial skills, and by psychiatric manifestations. In certain embodiments, it is associated with degenerating neurons in several regions of the brain. The term "dementia" as used herein includes, but is not restricted to, Alzheimer's dementia with or without psychotic symptoms. In certain embodiment, the therapeutic methods provided herein are effective for the treatment of mild, moderate and severe Alzheimer's disease in a subject. Phases of Alzheimer's further include "moderately severe cognitive decline," also referred to as "moderate or mid-stage Alzheimer's disease," "severe cognitive decline," also referred to as "moderately severe or mid-stage Alzheimer's disease," and "very severe cognitive decline," also referred to as "severe or late-stage Alzheimer's disease." Moderately severe cognitive decline is characterized by major gaps in memory and deficits in cognitive function emerge. At this stage, some assistance with day-to-day activities becomes essential. In severe cognitive decline, memory difficulties continue to worsen, significant personality changes may emerge and affected individuals need extensive help with customary daily activities. Late stage Alzheimer's disease or very severe cognitive decline is the final stage of the disease when individuals lose the ability to respond to their environment, the ability to speak and, ultimately, the ability to control movement.

Biologically activity: As used herein, the term "Biologically activity" refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agents or modalities to a subject receiving the other agents or modalities in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Diabetes: A central characteristic of diabetes is impaired β-cell function. One abnormality that occurs early in disease progression in both type I and II diabetes is the loss of eating-induced rapid insulin response. Consequently, the liver continues to produce glucose, which adds to glucose that is ingested and absorbed from the basic components of a meal.

Type II Diabetes: One characteristic of type II diabetes is impaired insulin action, termed insulin resistance. Insulin resistance manifests itself as both a reduced maximal glucose elimination rate (GERmax) and an increased insulin concentration required to attain GERmax. Thus, to handle a given glucose load more insulin is required and that increased insulin concentration must be maintained for a longer period of time. Consequently, the diabetic patient is also exposed to elevated glucose concentrations for prolonged periods of time, which further exacerbates insulin resistance. Additionally, prolonged elevated blood glucose levels are themselves toxic to β-cells. Another characteristic of type II diabetics is a delayed response to increases in blood glucose levels. While normal individuals usually begin to release insulin within 2-3 minutes following consumption of food, type II diabetics may not secrete endogenous insulin until blood glucose begins to rise, and then with second-phase kinetics, that is a slow rise to an extended plateau in concentration. As a result, endogenous glucose production is not shut off and continues after consumption and the patient experiences hyperglycemia (elevated blood glucose levels). Type II diabetes arises from different and less well understood circumstances. The early loss of early phase insulin release, and consequent continual glucose release, contributes to elevated glucose concentrations. High glucose levels promote insulin resistance, and insulin resistance generates prolonged elevations of serum glucose concentration. This situation can lead to a self-amplifying cycle in which ever greater concentrations of insulin are less effective at controlling blood glucose levels. Moreover, as noted above, elevated glucose levels are toxic to β-cells, reducing the number of functional β-cells. Genetic defects impairing the growth or maintenance of the microvasculature nourishing the islets can also play a role in their deterioration (Glee, S. M., et al. Nature Genetics 38:688-693, 2006). Eventually, the pancreas becomes overwhelmed, and individuals progress to develop insulin deficiency similar to people with type I diabetes.

Type I Diabetes: Type I diabetes occurs as a result of the destruction of insulin-producing cells of the pancreas (β-cells) by the body's own immune system. This ultimately results in a complete insulin hormone deficiency.

Dosage form or unit dosage form: As used herein, the term "dosage form or unit dosage form" refers to a physically discrete unit of an active agent (e.g., a therapeutic or diagnostic agent) for administration to a subject. In some embodiments, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: As used herein, the term "excipient" refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Honeymoon phase: As used herein, the term "honeymoon phase" of type 1 diabetes refers to early stages of the disease characterized by loss of early phase insulin release and the remaining β-cell function produces some insulin, which is released with second-phase kinetics.

Hyperglycemia: As used herein, the term "Hyperglycemia" refers to a disease, disorder, or condition characterized by a higher than normal fasting blood glucose concentration. In some embodiments, hyperglycemia is characterized by a blood glucose concentration of 126 mg/dL or higher. In some embodiments, hyperglycemia is characterized by a blood glucose concentration of 280 mg/dL (15.6 mM) or higher.

Hypoglycemia: As used herein, the term "hypoglycemia" refers to a disease, disorder, or condition characterized by a lower than normal blood glucose concentration. In some embodiments, hypoglycemia is characterized by a blood glucose concentration of 63 mg/dL (3.5 mM) or lower. In some embodiments, hypoglycemia causes symptoms such as cognitive impairment, behavioral changes, pallor, diaphoresis hypotonia, flush and weakness that are recognized symptoms of hypoglycemia and that disappear with appropriate caloric intake. In some embodiments, hypoglycemia is severe such that glucagon injections, glucose infusions, or help by another party are required.

Improve, increase, inhibit or reduce: As used herein, the terms "improve", "increase", "inhibit', and "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Insulin-related disorder: As used herein, the term "insulin-related disorders" refers to disorders involving production, regulation, metabolism, and action of insulin in a mammal. Insulin-related disorders include, but are not limited to, pre-diabetes, type I diabetes, type II diabetes, hypoglycemia, hyperglycemia, insulin resistance, secretory dysfunction, sarcopenia, loss of pancreatic β-cell function, and loss of pancreatic β-cells.

Non-insulin dependent patients having insulin-related disorders: As used herein, the term "non-insulin dependent patients having insulin-related disorders" refers to patients with disorders for which therapy with exogenously-provided insulin is not the current standard treatment upon diagnosis. Non-insulin dependent patients having insulin-related disorders which are not treated with exogenously-administered insulin include early type II diabetes, type I diabetes in the honeymoon phase, pre-diabetes and insulin-producing cell transplant recipients.

Insulin resistance: As used herein, the term "insulin resistance" refers to the inability of a patient's cells to respond to insulin appropriately or efficiently. The pancreas responds to this problem at the cellular level by producing more insulin. Eventually, the pancreas cannot keep up with the body's need for insulin and excess glucose builds up in the bloodstream. Patients with insulin resistance often have high levels of blood glucose and high levels of insulin circulating in their blood at the same time.

Insulin resistance disorder: As used herein, the term "insulin resistance disorder" refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

Isomer: As is known in the art, many chemical entities (in particular many organic molecules and/or many small molecules) can exist in a variety of structural (e.g., geometric, conformational, isotopic) and/or optical isomeric forms. For example, any chiral center can exist in R and S configurations, double bonds can exist in Z and E conformational isomers, certain structural elements can adopt two or more tautomeric forms, certain structures can be substituted with one or more isotopically enriched atoms (e.g., deuterium or tritium for hydrogen, $^{12}C$ or $^{14}C$ for $^{13}C$, $^{131}I$ for $^{129}I$, etc.). In some embodiments, as will be clear to those skilled in the art from context, depiction of or reference to a particular compound structure herein may represent all structural and/or optical isomers thereof. In some embodiments, as will be clear to those skilled in the art from context, depiction of or reference to a particular compound structure herein is intended to encompass only the depicted or referenced isomeric form. In some embodiments, compositions including a chemical entity that can exist in a variety of isomeric forms include a plurality of such forms; in some embodiments such compositions include only a single form. For example, in some embodiments, compositions including a chemical entity that can exist as a variety of optical isomers (e.g., stereoisomers, diastereomers, etc.) include a racemic population of such optical isomers; in some embodiments such compositions include only a single optical isomer and/or include a plurality of optical isomers that together retain optical activity.

Parenteral: As used herein, the terms "parenteral administration" and "administered parenterally" refer to modes of administration other than enteral and topical administration, usually by injection. In some embodiments, parenteral administration may be or comprise intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and/or infusion.

Partially Unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. Those skilled in the art will appreciate that, in general, any composition that is formulated for administration to a human or animal subject, may, in some embodiments, be considered to be a pharmaceutical composition, whether or not its administration requires a medical prescription. Thus, for example, in some embodiments, a food or food supplement composition (e.g., a liquid or solid consumable composition such as a shake or sports drink or nutritional supplement powder) may be considered to be a pharmaceutical composition. Alternatively or additionally, in some embodiments, a pharmaceutical composition may be a formulation that is specifically regulated and approved for administration to relevant subjects by an appropriate government agency such as, for example, the Food and Drug Administration in the United States. In some embodiments, a pharmaceutical composition is one that cannot legally be administered without a prescription from a licensed medical practitioner.

Pharmaceutically acceptable: As used herein, the term "pharmaceutically acceptable" applied to a carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" refers to a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pre-Diabetes: As used herein, the term "pre-diabetes" refers to a disease, disorder, or condition where the patients have impaired fasting glucose, and/or impaired glucose tolerance. In some embodiments, pre-diabetic patients have a fasting blood glucose level between 100 mg/dL (5.5 mmol/L) and 126 mg/dL (7.0 mmol/L). In some embodiments, pre-diabetic patients have a 2 hour post-prandial blood glucose level between 140 mg/dL (7.8 mmol/L) and 200 mg/dL (11.1 mmol/L).

Prodrug: As used herein, the term "prodrug" refers to a pharmacologically active or more typically an inactive compound that is converted into a pharmacologically active agent by a metabolic transformation. Prodrugs of a compound of any of the formulas as described herein are prepared by modifying functional groups present in the compound of any of the formulas in such a way that the modifications may be cleaved in vivo to release the parent compound. In vivo, a prodrug readily undergoes chemical changes under physiological conditions (e.g., are hydrolyzed or acted on by naturally occurring enzyme(s)) resulting in liberation of the pharmacologically active agent. Prodrugs include compounds of any of the formulas as described herein wherein a hydroxyl, amino, or carboxyl group is bonded to any group that may be cleaved in vivo to regenerate the free hydroxyl, amino or carboxyl group, respectively. Examples of prodrugs include, but are not limited to esters (e.g., acetate, formate, and benzoate derivatives) of compounds of any of the formulas as described herein or any other derivative which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

Proliferative condition: As used herein, the term "proliferative condition" refers to a disease or disorder associated with cell proliferation. In some embodiments, a proliferative disease or disorder is or comprises cancer. In some embodiments, a proliferative disease or disorder is an inflammatory disease or disorder. In some embodiments, a proliferative disease or disorder is an autoimmune disease or disorder. In some embodiments, a proliferative disease or disorder is a microbial infection (e.g., a bacterial infection).

Reference: As used herein, the term "reference" refers to a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Risk: As used herein, the "risk" of a disease, disorder, and/or condition refers to the likelihood that a particular individual will develop a disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Solid form: As is known in the art, many chemical entities (in particular many organic molecules and/or many small molecules) can adopt a variety of different solid forms such as, for example, amorphous forms and/or crystalline forms (e.g., polymorphs, hydrates, solvates, etc.). In some embodiments, such entities may be utilized as a single such form (e.g., as a pure preparation of a single polymorph). In some embodiments, such entities may be utilized as a mixture of such forms.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Therapeutically effective amount: As used herein, the term "Therapeutically effective amount" refers to an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to administration of a therapy that partially or completely alleviates, ameliorates, relieves, inhibits, delays onset of (e.g., relative to an established onset time or period), reduces severity of, and/or reduces incidence of one or more symptoms, features, and/or causes of a particular disease, disorder, and/or condition. In some embodiments, treatment may be of a subject who does not exhibit signs or symptoms of the relevant disease, disorder and/or condition, and/or of a subject who is not diagnosed suffering the relevant disease, disorder and/or condition, and/or of a subject who exhibits only early signs of the disease, disorder, and/or condition. Alternatively or additionally, in some embodiments, treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. In some embodiments, such treatment refers to reducing risk of developing the disease, disorder and/or condition and/or to delaying onset of one or more characteristics or symptoms of the disease, disorder or condition. In some embodiments, treatment is administration of therapy according to a regimen that has been demonstrated to achieve a relevant result (e.g., to partially or completely alleviate, ameliorate, relieve, inhibit, delay onset of, reduce severity of, and/or reduce incidence of one or more symptoms, features, and/or cause of a particular disease, disorder, and/or condition) with statistical significance when applied to a relevant population or system (e.g., model system). In some embodiments, treatment administered after diagnosis and/or onset of one or more symptoms is considered to be "therapeutic" treatment, whereas treatment administered prior to diagnosis and/or to onset of symptoms is considered to be "prophylactic" treatment.

Unit dose: As used herein, the term "unit dose" refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Alkyl: As used herein, the term "alkyl" refers to linear or branched alkyl groups. Exemplary $C_{1-6}$alkyl groups include, but are not limited to, methyl, ethyl, propyl, isopropyl, butyl, isobutyl, tert-butyl, pentyl, isopentyl, neopentyl, and hexyl.

Heteroatom: As used herein, the term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Carbocyclic: As used herein, the term "carbocyclic" refers to a monocyclic hydrocarbon that is completely saturated or that contains one or more units of unsaturation, but which is not aromatic, that has a single point of attachment to the rest of the molecule.

Heterocyclic: As used herein, the term "heterocyclic" refers to a stable monocyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of 3-8 membered heterocyclic include tetrahydrofuranyl, tetrahydrothiophenyl, pyrrolidinyl, piperidinyl, pyrrolinyl, oxazolidinyl, piperazinyl, dioxanyl, dioxolanyl, diazepinyl, oxazepinyl, thiazepinyl, and morpholinyl.

Halogen: As used herein, the terms "halogen" and "halo" refer to F, Cl, Br, or I.

Compound C: The term "Compound C", as used herein, refers to 5'-Methylselenoadenosine; also known as (2R, 4S, 5S)-2-(6-amino-9H-purin-9-yl)-5-((methylselanyl)methyl)tetrahydrofuran-3,4-diol, CAS Registry Number 5135-40-0, and includes any pharmaceutically acceptable salts thereof.

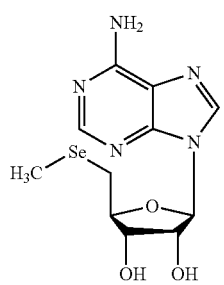

Compound C

Compound D: The term "Compound D", as used herein, refers to 5'-Selenoadenosyl homocysteine; also known as (2R)-2-amino-4-(((((2S,3S,5R)-5-(6-amino-9H-purin-9-yl)-3,4-dihydroxytetrahydrofuran-2-yl)methyl)selanyl)butanoic acid, CAS Registry Number 4053-91-2, and includes any pharmaceutically acceptable salts thereof.

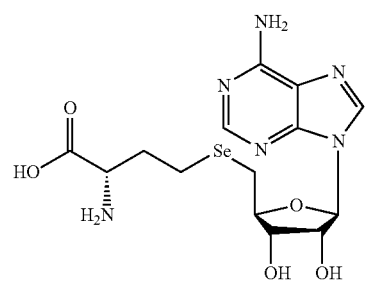

Compound D

Compound E: The term "Compound E", as used herein, refers to gamma-glutamyl-methylseleno-cysteine or γ-L-glutamyl-Se-methyl-L-cysteine; also known as N5-(1-carboxy-2-(methylselanyl)ethyl)-L-glutamine, or any pharmaceutically acceptable salt thereof.

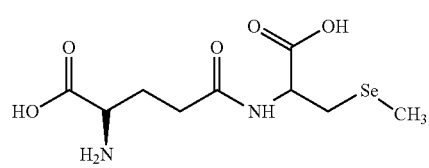

Compound E

Compound CDE: The term "Compound CDE", as used herein, refers to a mixture of Compound C, Compound D, and Compound E, or pharmaceutically acceptable salts thereof.

Compounds

The present disclosure provides a number of exemplary compounds capable of lowering glucose level, improving glucose tolerance, restoring or activating insulin receptor function and its downstream signaling, enhancing AS160 phosphorylation for translocation of glucose transporter proteins (GLUTs) from cytosolic vesicles to plasma membrane for glucose uptake, stimulating glucose uptake, and attenuating hyperinsulinemia without impaired kidney function and/or liver damage in diabetic mice, cultured liver and/or skeletal muscle cells after treatment of single compound. For example, Example 2 shows that each of Compounds 43, 50, 53, 69, and 70 lowered glucose production in HepG2 cells. Particularly, Compound 43 exhibited higher potency than Compound CDE. When compared to antidiabetic drug metformin in HepG2 and rat H4IIE cells, Compound 43 showed greater potency and lower cell toxicity. It was also shown that Compound #43 is more potent than Compound 50 in the inhibition of the expression of G6pc (a key enzyme gene for liver glucose production) in the liver of diabetic mice, and than Compound CDE, Compound C, Compound D and Compound 50 in mouse liver AML-12 cells (Example 4). Further, the present disclosure demonstrates that compound 43 is more potent than compound C, compound 50, compound 69 and compound 70 against hyperglycermia in diabetic mice (Example 3); that Compound 43 significantly improves glucose tolerance (Example 3) and enhances/restores insulin receptor function and its downstream signaling in the livers and skeletal muscles of insulin-resistant diabetic Lepr$^{db/db}$ mice (Examples 5 and 7-8); and that Compound 43 elicits a response to the glucose challenge in diabetic mice which was similar to the response in wild-type mice (Example 3). In addition, the present disclosure demonstrates that Compound #43 treatment can enhance the phosophorylation of AS160 (to promote the translocation of GLUTs from cellular vesicles to plasma membrane) for glucose uptake in both liver and skeletal muscle cells (Example 8), stimulate GLUT4 expression in the liver of diabetic mice and cultured mouse liver cells (Example 6), enhance and/or potentiate insulin action to stimulate glucose uptake in the liver and skeletal muscle cells (Example 6-7), and attenuate the hyperinsulinemia without impaired kidney function and/or liver damage in the insulin-resistant diabetic mice (Example 9).

The present disclosure also provides features of selenium compounds which may contribute to its activity. For example, it was shown that while selenium Compound #43 had a great potency in inhibiting glucose production, its sulfur analog Compound 68 had a low potency (Example 2); and that Compound #43 is more potent than Compound #68 in lowering blood glucose and HbA1c levels and improving glucose tolerance in insulin-resistant diabetic mice (Example 3). It was also shown that inhibition of glucose production was observed after treatment of selenium compounds comprising, at 2' and 3' position, diacetyl ester (#43), cyclic carbonate (Compound #50), morpholino carboxylate (#53), dipropanoyl ester (#69), or dibutanoyl ester (#70), with the greatest potency observed after treatment of Compound 43 (Example 2). Further, it was shown that compounds comprising a 5' methyl seleno group and a 5' seleno homocysteine group had similar potency in inhibiting glucose production in HepG2 cells (compound C vs. compound D in Example 2). In vivo studies also revealed that Compound #43 is more potent than Compound #69 and #70 in lowering blood glucose levels and improving glucose tolerance in insulin-resistant diabetic mice (Example 3).

In some embodiments, the present disclosure relates to a compound of formula (1):

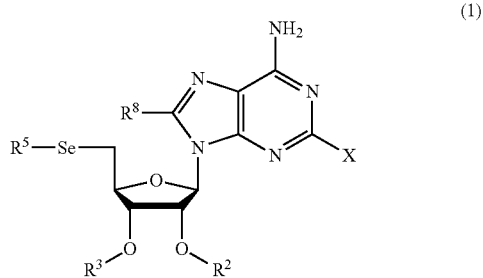

or a pharmaceutically acceptable salt, prodrug, or isomer thereof, wherein each of $R^2$ and $R^3$ is independently H or —C(O)—R, wherein each R is independently $C_{1-6}$alkyl or 3-8 membered carbocyclic or heterocyclic, wherein $R^2$ and $R^3$ cannot be both H;

or $R^2$ together with $R^3$ form —(CH$_2$)$_n$—C(O)—(CH$_2$)$_m$—, wherein each of n and m is independently 0-3, and n+m≤3;

$R^5$ is —$C_{1-6}$alkyl or —$C_{1-6}$alkyl-CH(NH$_2$)COOH;

$R^8$ is H or halogen; and

X is H or halogen;

wherein each of the carbocyclic, heterocyclic, —(CH$_2$)$_n$—, and —(CH$_2$)$_m$— moieties, independently, may optionally be substituted 1-3 times by —OH, halogen, NH$_2$, CN, or $C_{1-6}$alkyl; and each $C_{1-6}$alkyl moiety, independently, may optionally be substituted 1-3 times by —OH, halogen, NH$_2$, or CN.

In some embodiments of formula (1), $R^8$ is H. In some embodiments of formula (1), $R^8$ of formula (1) is halogen. In some embodiments of formula (1), $R^8$ of formula (1) is F.

In some embodiments of formula (1), X is H. In some embodiments of formula (1), X is halogen. In some embodiments of formula (1), X is F.

In some embodiments of formula (1), $R^5$ is —$C_{1-6}$alkyl, which may optionally be substituted 1-3 times by —OH, halogen, NH$_2$, or CN. In some embodiments of formula (1), $R^5$ is —$C_{1-6}$alkyl, which may optionally be substituted 1-3 times by halogen. In some embodiments of formula (1), $R^5$ is unsubstituted —$C_{1-6}$alkyl. In some embodiments of formula (1), $R^5$ is unsubstituted linear —$C_{1-6}$alkyl. In some embodiments of formula (1), $R^5$ is methyl. In some embodiments of formula (1), $R^5$ is ethyl. In some embodiments of formula (1), $R^5$ is propyl.

In some embodiments of formula (1), $R^5$ is —$C_{1-6}$ alkyl-CH(NH$_2$)COOH, wherein $C_{1-6}$alkyl may optionally be substituted 1-3 times by —OH, halogen, NH$_2$, or CN. In some embodiments of formula (1), $R^5$ is —$C_{1-6}$ alkyl-CH(NH$_2$)COOH, wherein $C_{1-6}$ alkyl may optionally be substituted 1-3 times by halogen. In some embodiments of formula (1), $R^5$ is —$C_{1-6}$alkyl-CH(NH$_2$)COOH, wherein $C_{1-6}$alkyl is unsubstituted. In some embodiments of formula (1), $R^5$ is —CH$_2$CH$_2$—CH(NH$_2$)COOH. In some embodiments of formula (1), $R^5$ is —CH$_2$—CH(NH$_2$)COOH. In some embodiments of formula (1), $R^5$ is —CH$_2$CH$_2$CH$_2$—CH(NH$_2$)COOH.

In some embodiments of formula (1), $R^2$ is H, and $R^3$ is —C(O)—R, wherein R is $C_{1-6}$alkyl or 3-8 membered carbocyclic or heterocyclic, wherein each of the carbocyclic and heterocyclic moieties, independently, may optionally be substituted 1-3 times by —OH, halogen, NH$_2$, CN, or $C_{1-6}$alkyl; and each $C_{1-6}$alkyl, independently, may optionally be substituted 1-3 times by —OH, halogen, NH$_2$, or CN.

In some embodiments of formula (1), $R^3$ is H, and $R^2$ of formula (1) is —C(O)—R, wherein R is $C_{1-6}$alkyl or 3-8 membered carbocyclic or heterocyclic, wherein each of the carbocyclic and heterocyclic moieties, independently, may optionally be substituted 1-3 times by —OH, halogen, NH$_2$, CN, or $C_{1-6}$alkyl; and each $C_{1-6}$alkyl, independently, may optionally be substituted 1-3 times by —OH, halogen, NH$_2$, or CN.

In some embodiments of formula (1), each of $R^2$ and $R^3$ is independently —C(O)—R, wherein each R is independently $C_{1-6}$alkyl or 3-8 membered carbocyclic or heterocyclic, wherein each of the carbocyclic and heterocyclic moieties, independently, may optionally be substituted 1-3 times by —OH, halogen, NH$_2$, CN, or $C_{1-6}$alkyl; and each $C_{1-6}$alkyl, independently, may optionally be substituted 1-3 times by —OH, halogen, NH$_2$, or CN.

In some embodiments of formula (1), each R is independently 3-8 membered carbocyclic or heterocyclic, wherein each of the carbocyclic and heterocyclic moieties, independently, may optionally be substituted 1-3 times by —OH, halogen, NH$_2$, CN, or $C_{1-6}$alkyl; and each $C_{1-6}$alkyl, independently, may optionally be substituted 1-3 times by —OH, halogen, NH$_2$, or CN. In some embodiments of formula (1), each R is independently 3-8 membered carbocyclic or heterocyclic, wherein each of the carbocyclic and heterocyclic moieties, independently, may optionally be substituted 1-3 times by halogen. In some embodiments of formula (1), each R is independently 3-8 membered carbocyclic or heterocyclic, wherein each of the carbocyclic and heterocyclic moieties, independently, may optionally be substituted 1-3 times by halogen. In some embodiments of formula (1), each R is independently 3-8 membered unsubstituted carbocyclic or unsubstituted heterocyclic. In some embodiments of formula (1), each R is independently 6 membered unsubstituted carbocyclic or unsubstituted heterocyclic. In some embodiments of formula (1), each R is independently unsubstituted heterocyclic. In some embodiments of formula (1), R is

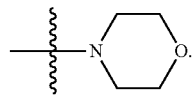 [SMILES: *N1CCOCC1]

In some embodiments of formula (1), each R is independently $C_{1-6}$alkyl, and each $C_{1-6}$alkyl, independently, may optionally be substituted 1-3 times by —OH, halogen, $NH_2$, or CN. In some embodiments of formula (1), each R is independently $C_{1-6}$alkyl, and each $C_{1-6}$alkyl, independently, may optionally be substituted 1-3 times by halogen. In some embodiments of formula (1), each R is independently unsubstituted $C_{1-6}$alkyl. In some embodiments of formula (1), each R is independently unsubstituted linear $C_{1-6}$alkyl. In some embodiments of formula (1), each R is independently methyl, ethyl, or propyl. In some embodiments of formula (1), R is $CH_3$.

In some embodiments of formula (1), $R^2$ together with $R^3$ form —$(CH_2)_n$—C(O)—$(CH_2)_m$—, wherein each of n and m is independently 0-3, and n+m≤3, wherein each of the —$(CH_2)_n$— and —$(CH_2)_m$— moieties, independently, may optionally be substituted 1-3 times by —OH, halogen, $NH_2$, CN, or $C_{1-6}$alkyl; and each $C_{1-6}$alkyl, independently, may optionally be substituted 1-3 times by —OH, halogen, $NH_2$, or CN. In some embodiments of formula (1), each of the —$(CH_2)_n$— and —$(CH_2)_m$— moieties, independently, may optionally be substituted 1-3 times by halogen. In some embodiments of formula (1), the —$(CH_2)_n$— and —$(CH_2)_m$— moieties are unsubstituted. In some embodiments, n=m=0.

In some embodiments, the present disclosure relates to a compound of formula (2):

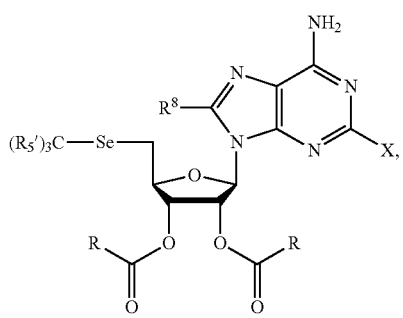

or a pharmaceutically acceptable salt, prodrug, or isomer thereof,
wherein $R^8$ is H or halogen;
X is H or halogen;
each $R_5'$ is independently H or halogen; and
each R is independently $C_{1-6}$alkyl, each of which, independently, may optionally be substituted 1-3 times by halogen.

In some embodiments of formula (2), $C(R_5')_3$ is $CF_3$, $CHF_2$, $CH_2F$, or $CH_3$.

In some embodiments of formula (2), the compound is of formula (2'):

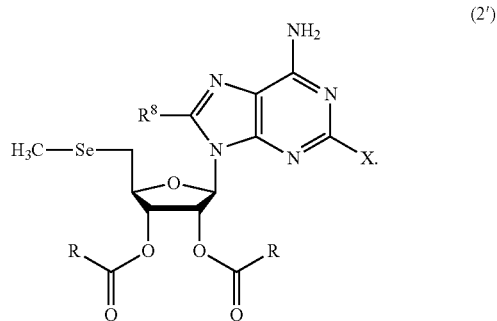

In some embodiments of formula (2) or (2'), $R^8$ is H. In some embodiments of formula (2) or (2'), $R^8$ is halogen. In some embodiments of formula (2) or (2'), $R^8$ is F.

In some embodiments of formula (2) or (2'), X is H. In some embodiments of formula (2) or (2'), X is halogen. In some embodiments of formula (2) or (2'), X is F.

In some embodiments of formula (2) or (2'), R is each independently unsubstituted $C_{1-6}$alkyl. In some embodiments of formula (2) or (2'), R is each independently $C_{1-3}$alkyl, each of which, independently, may optionally be substituted 1-3 times by halogen. In some embodiments of formula (2) or (2'), R is each independently unsubstituted $C_{1-3}$alkyl. In some embodiments of formula (2) or (2'), R is each independently —$CH_3$, —$CH_2CH_3$, or —$CH_2CH_2CH_3$.

In some embodiments, the present disclosure relates to a compound of formula (3):

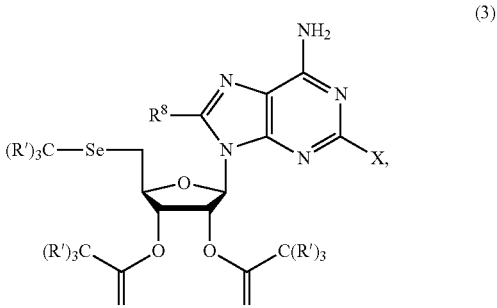

or a pharmaceutically acceptable salt, prodrug, or isomer thereof,
wherein $R^8$ is H or halogen;
X is H or halogen; and
each R' is independently H or halogen.

In some embodiments of formula (3), —Se—$C(R')_3$ is —Se—$CH_3$, —Se—$CHF_2$, —Se—$CH_2F$, or —Se—$CF_3$.

In some embodiments of formula (3), the compound is of formula (3'):

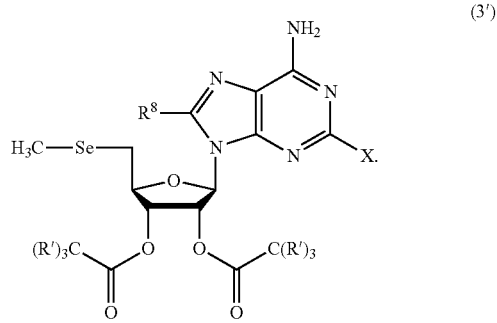

In some embodiments of formula (3) or (3'), $R^8$ is H. In some embodiments of formula (3) or (3'), $R^8$ is halogen. In some embodiments of formula (3) or (3'), $R^8$ is F.

In some embodiments of formula (3) or (3'), X is H. In some embodiments of formula (3) or (3'), X is halogen. In some embodiments of formula (3) or (3'), X is F.

In some embodiments of formula (3) or (3'), each $C(R')_3$ is independently $CF_3$, $CHF_2$, or $CH_2F$, or $CH_3$. In some embodiments of formula (3) or (3'), each $C(R')_3$ is independently $CH_2F$ or $CH_3$. In some embodiments of formula (3) or (3'), each $C(R')_3$ is $CH_3$.

In some embodiments, the present disclosure relates to a compound of formula:

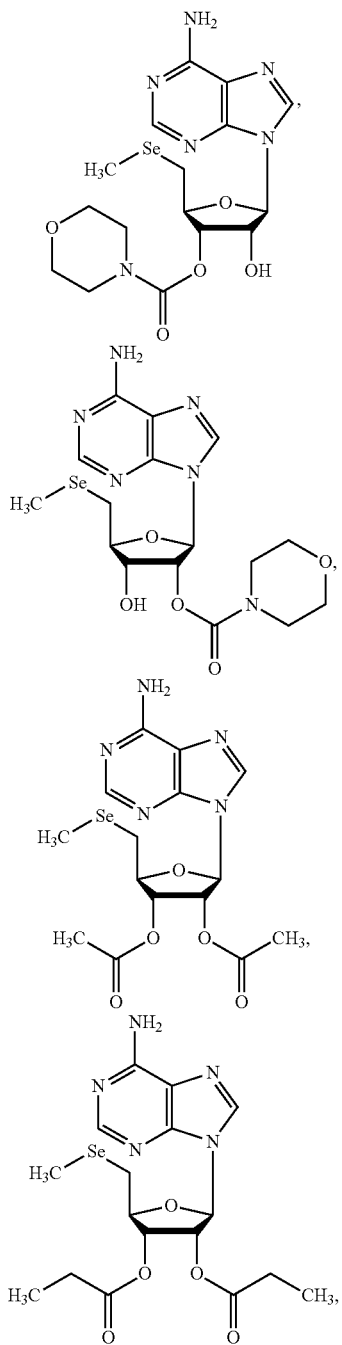

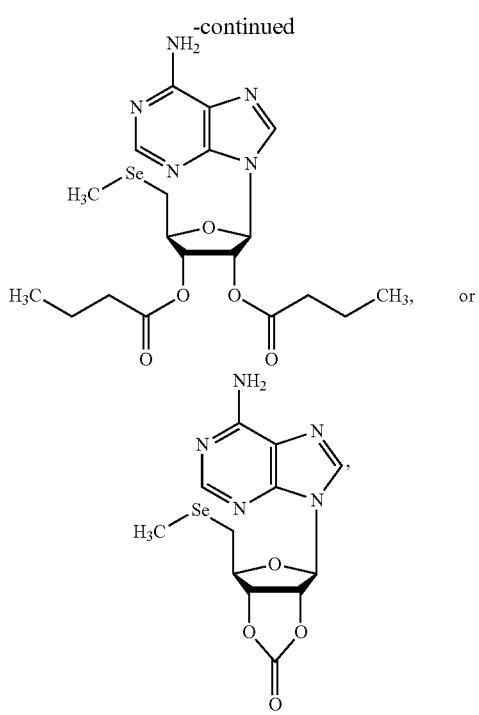

or a pharmaceutically acceptable salt, prodrug, or isomer thereof.

Formulations

In some embodiments, the present disclosure provides compositions that comprise and/or deliver (i.e., upon administration to a system or subject) a compound of any one of formulas (1)-(3), or a pharmaceutically acceptable salt, prodrug, or isomer thereof. In some embodiments, the present disclosure provides compositions comprising only a single compound of any one of formulas (1)-(3), or a pharmaceutically acceptable salt, prodrug, or isomer thereof. In some embodiments, the present disclosure provides compositions comprising one or more compounds of any one of formulas (1)-(3), or a pharmaceutically acceptable salt, prodrug, or isomer thereof, and one or more carriers or excipients appropriate for administration to human or animal subjects in accordance with the present disclosure.

In some embodiments, the present disclosure provides compositions that deliver an active moiety of a compound of any one of formulas (1)-(3). In some embodiments, the composition comprises an active metabolite of a compound of any one of formulas (1)-(3). In some embodiments, the composition comprises a compound which forms a metabolite of a compound of any one of formulas (1)-(3) upon administration of said composition, which metabolite maintains relevant biological activity.

In some embodiments, the present disclosure provides compositions that are pharmaceutical compositions in that they contain an active pharmaceutical ingredient (API) and one or more pharmaceutically acceptable carriers or excipients. In some embodiments, the API is or comprises the compound of any one of formulas (1)-(3). In some embodiments, the API consists of the compound of any one of formulas (1)-(3). In some embodiments, the API consists of a single compound of any one of formulas (1)-(3).

In some embodiments, the present disclosure provides methods of manufacturing a provided composition, for example by combining one or more appropriate (i.e., pharmaceutically acceptable) carriers or excipients with a compound of any one of formulas (1)-(3), or a pharmaceutically acceptable salt, prodrug, or isomer thereof. In some embodiments, the one or more pharmaceutically acceptable carriers or excipients are suitable for oral administration and the mixture is formulated into an oral formulation. In some embodiments, the pharmaceutical composition is a solid dosage form. In some embodiments, the solid dosage form is a tablet, capsule, or lozenge. In some embodiments, the pharmaceutical composition is a liquid dosage form (e.g., a drink).

Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. In some embodiments, the present disclosure provides pharmaceutical compositions comprising a pharmaceutically acceptable amount of a compound as described herein. In some embodiments, amount of active ingredient which can be combined with a carrier material to produce a single dosage form may vary depending upon the host being treated, and/or the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

In some embodiments, wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

In some embodiments, formulations of the present invention include those suitable for oral, nasal, topical (including buccal and sublingual), rectal, vaginal and/or parenteral administration. In some embodiments, the formulations may conveniently be presented in unit dosage form and may be prepared by any methods well known in the art of pharmacy. In some embodiments, formulations as described herein comprise an excipient selected from the group consisting of cyclodextrins, liposomes, micelle forming agents, e.g., bile acids, and polymeric carriers, e.g., polyesters and polyanhydrides; and a compound as described herein. In some embodiments, formulations as described herein render orally bioavailable a compound as described herein.

In some embodiments, methods of preparing such formulations may comprise a step of bringing into association a compound as described herein with one or more pharmaceutically acceptable carriers or excipients, and optionally one or more accessory ingredients. In some embodiments, the formulations are prepared by uniformly and intimately bringing into association a compound as described herein with liquid carriers, or finely divided solid carriers, or both, and then, if necessary, shaping the product.

In some embodiments, formulations as described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes, drinks, and the like, each containing a predetermined amount of a compound as described herein as an active ingredient. In some embodiments, a compound as described herein may alternatively or additionally be administered as a bolus, electuary or paste.

In some embodiments, in solid dosage forms as described herein for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In some embodiments, in the case of capsules, tablets and pills, the pharmaceutical compositions may also comprise buffering agents. In some embodiments, solid compositions of a similar type may also be employed as fillers in soft and hard-shelled gelatin capsules using such carriers as lactose or milk sugars, as well as high molecular weight polyethylene glycols and the like.

In some embodiments, a tablet may be made by compression or molding, optionally with one or more accessory ingredients. In some embodiments, compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets may be made in a suitable machine in which a mixture of the powdered compound is moistened with an inert liquid diluent.

In some embodiments, the tablets, and other solid dosage forms of the pharmaceutical compositions as described herein, such as dragees, capsules, pills and granules, may optionally be scored or prepared with coatings and shells, such as enteric coatings and other coatings well known in the pharmaceutical-formulating art. In some embodiments, they may be formulated so as to provide slow or controlled release of the active ingredient therein using, for example, hydroxypropylmethyl cellulose in varying proportions to provide the desired release profile, other polymer matrices, liposomes and/or microspheres. In some embodiments, they may be formulated for rapid release, e.g., freeze-dried. In some embodiments, they may be sterilized by, for example, filtration through a bacteria-retaining filter, or by incorporating sterilizing agents in the form of sterile solid compositions that can be dissolved in sterile water, or some other sterile injectable medium immediately before use. In some embodiments, these compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. In some embodiments, the active ingredient can be in microencapsulated form, if appropriate, with one or more of the above-described excipients.

In some embodiments, liquid dosage forms for oral administration of the compounds as described herein include pharmaceutically acceptable emulsions, microemulsions, solutions, suspensions, syrups and elixirs. In some embodiments, in addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

In some embodiments, besides inert diluents, the oral compositions can include adjuvants such as wetting agents, emulsifying and suspending agents, sweetening, flavoring, coloring, perfuming and preservative agents.

In some embodiments, suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations as described herein for rectal or vaginal administration may be presented as a suppository, which may be prepared by mixing one or more compounds as described herein with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In some embodiments, formulations as described herein which are suitable for vaginal administration include pessaries, tampons, creams, gels, pastes, foams or spray formulations containing such carriers as are known in the art to be appropriate.

In some embodiments, dosage forms for the topical or transdermal administration of a compound as described herein include powders, sprays, ointments, pastes, creams, lotions, gels, solutions, patches and inhalants. In some embodiments, the active compound may be mixed under sterile conditions with a pharmaceutically-acceptable carrier, and with any preservatives, buffers, or propellants which may be required.

In some embodiments, the ointments, pastes, creams and gels may contain, in addition to a compound as described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays can contain, in addition to a compound as described herein, excipients such as lactose, talc, silicic acid, aluminum hydroxide, calcium silicates and polyamide powder, or mixtures of these substances. In some embodiments, sprays can additionally contain customary propellants, such as chlorofluorohydrocarbons and volatile unsubstituted hydrocarbons, such as butane and propane.

In some embodiments, transdermal patches have the added advantage of providing controlled delivery of a compound as described herein to the body. In some embodiments, dissolving or dispersing the compound in the proper medium can make such dosage forms. In some embodiments, absorption enhancers can be used to increase the flux of the compound across the skin. In some embodiments, either providing a rate controlling membrane or dispersing the compound in a polymer matrix or gel can control the rate of such flux.

In some embodiments, the present disclosure provides ophthalmic formulations, eye ointments, powders, solutions and the like.

In some embodiments, pharmaceutical compositions as described herein suitable for parenteral administration comprise one or more compounds as described herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions as described herein include water, ethanol, polyols (such as glycerol, propylene glycol, polyethylene glycol, and the like), and suitable mixtures thereof, vegetable oils, such as olive oil, and injectable organic esters, such as ethyl oleate. In some embodiments, proper fluidity can be maintained, for example, by the use of coating materials, such as lecithin, by the maintenance of the required particle size in the case of dispersions, and by the use of surfactants.

In some embodiments, the compositions as described herein may contain adjuvants such as preservatives, wetting agents, emulsifying agents and dispersing agents. In some embodiments, prevention of the action of microorganisms upon the subject compounds may be ensured by the inclusion of various antibacterial and antifungal agents, for example, paraben, chlorobutanol, phenol sorbic acid, and the like. In some embodiments, it may be desirable to include isotonic agents, such as sugars, sodium chloride, and the like into the compositions. In some embodiments, prolonged absorption of the injectable pharmaceutical form may be brought about by the inclusion of agents which delay absorption such as aluminum monostearate and gelatin.

In some embodiments, for example in order to prolong the effect of a drug, it is desirable to slow the absorption of the drug from subcutaneous or intramuscular injection. In some embodiments, this may be accomplished by the use of a liquid suspension of crystalline or amorphous material having poor water solubility. In some embodiments, the rate of absorption of the drug then depends upon its rate of dissolution, which in turn, may depend upon crystal size and crystalline form. In some embodiments, delayed absorption of a parenterally-administered drug form is accomplished by dissolving or suspending the drug in an oil vehicle.

In some embodiments, injectable depot forms are made by forming microencapsule matrices of the subject compounds in biodegradable polymers such as polylactide-polyglycolide. In some embodiments, depending on the ratio of drug to polymer, and the nature of the particular polymer employed, the rate of drug release can be controlled. Examples of other biodegradable polymers include poly (orthoesters) and poly(anhydrides). In some embodiments, depot injectable formulations are prepared by entrapping the drug in liposomes or microemulsions, which are compatible with body tissue.

In some embodiments, drug-eluting forms include coated or medicated stents and implantable devices. In some embodiments, drug-eluting stents and other devices may be coated with a compound or pharmaceutical preparation and may further comprise a polymer designed for time-release.

In some embodiments, a compound or pharmaceutical preparation is administered orally. In some embodiments, the compound or pharmaceutical preparation is administered intravenously. In some embodiments, a compound is attached via a cleavable linker to a solid support that is administered with a catheter. In some embodiments, routes of administration include sublingual, intramuscular, and transdermal administrations.

In some embodiments, the compounds as described herein are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

In some embodiments, the compounds as described herein may be given orally, parenterally, topically, or rectally. In some embodiments, they are of course given in forms suitable for each administration route. In some embodiments, they are administered in tablets or capsule form, by injection, inhalation, eye lotion, ointment, suppository, etc. administration by injection, infusion or inhalation; topical by lotion or ointment; and rectal by suppositories.

In some embodiments, the compounds as described herein may be administered to humans and other animals for therapy by any suitable route of administration, including orally, nasally, as by, for example, an aerosol, a spray, rectally, intravaginally, parenterally, intracisternally and topically, as by powders, ointments or drops, including buccally and sublingually.

In some embodiments, the compounds as described herein, which may be used in a suitable hydrated form, and/or the pharmaceutical compositions as described herein, are formulated into pharmaceutically-acceptable dosage forms by conventional methods known to those of skill in the art.

In some embodiments, actual dosage levels of the active ingredients in the pharmaceutical compositions as described herein may be varied so as to obtain an amount of the active ingredient that is effective to achieve the desired therapeutic response for a particular patient, composition, and mode of administration, without being toxic to the patient.

In some embodiments, a selected dosage level will depend upon a variety of factors including the activity of the particular compound as described herein, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can determine and prescribe the effective amount of the pharmaceutical composition required. In some embodiments, the physician or veterinarian could start doses of the compounds as described herein in the pharmaceutical composition at levels lower than that required to achieve the desired therapeutic effect and then gradually increasing the dosage until the desired effect is achieved.

In some embodiments, compounds or pharmaceutical compositions as described herein are provided to a subject chronically. In some embodiments, chronic treatments include any form of repeated administration for an extended period of time, such as repeated administrations for one or more months, between a month and a year, one or more years, or longer. In some embodiments, a chronic treatment involves administering a compound or pharmaceutical composition as described herein repeatedly over the life of the subject. In some embodiments, chronic treatments involve regular administrations, for example one or more times a day, one or more times a week, or one or more times a month. In some embodiments, a suitable dose such as a daily dose of a compound as described herein will be that amount of the compound that is the lowest dose effective to produce a therapeutic effect. Such an effective dose will generally depend upon the factors described herein. In some embodiments, doses of the compounds as described herein for a patient, when used for the indicated effects, will range from about 0.0001 to about 100 mg per kg of body weight per day. In some embodiments, the daily dosage will range from 0.001 to 50 mg of compound per kg of body weight. In some embodiments, the daily dosage will range from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, the effective daily dose of the active compound may be administered as two, three, four, five, six, or more sub-doses administered separately at appropriate intervals throughout the day, optionally, in unit dosage forms.

In some embodiments, a compound as described herein is administered alone. In some embodiments, a compound as described herein is administered as a pharmaceutical formulation (composition) as described herein.

In some embodiments, the compounds as described herein may be formulated for administration in any convenient way for use in human or veterinary medicine, by analogy with other pharmaceuticals.

Preparation of Compounds and/or Compositions

In some embodiments, a compound of any one of formulas (1)-(3), or a pharmaceutically acceptable salt, prodrug, or isomer thereof, may be prepared in whole or in part by chemical synthesis; in some embodiments, a compound of any one of formulas (1)-(3), or a pharmaceutically acceptable salt, prodrug, or isomer thereof, prepared in part by chemical synthesis is prepared using semi-synthetic methodologies. In some embodiments, a compound of any one of formulas (1)-(3), or a pharmaceutically acceptable salt, prodrug, or isomer thereof, may be prepared by isolation.

In some embodiments, the present disclosure provides methods for preparing a Compound and/or Composition as described herein, comprising assaying one or more samples, for example to detect bioactivity therein. In some embodiments, one or more of the samples comprise a compound of any one of formulas (1)-(3), or a pharmaceutically acceptable salt, prodrug, or isomer thereof. In some embodiments, methods provided herein comprise a step of detecting and/or confirming presence of detectable bioactivity in one or more samples. In some embodiments, methods provided herein comprise a step of confirming absence of detectable bioactivity in one or more samples.

In some embodiments, the bioactivity is inhibition of glucose production. In some embodiments, the bioactivity is tested in HepG2 cells. In some embodiments, the bioactivity is tested in H4IIE cells.

In some embodiments, the bioactivity is reduction of serum HbA1c level. In some embodiments, the bioactivity is tested in insulin-resistant and diabetic mice.

In some embodiments, the bioactivity is enhanced glucose tolerance. In some embodiments, the bioactivity is tested in insulin-resistant and diabetic mice.

In some embodiments, the bioactivity is inhibition of G6pc expression. In some embodiments, the bioactivity is tested in AML-12 cells. In some embodiments, the bioactivity is tested in AML-12 cells stimulated with diabetic stimuli. In some embodiments, the bioactivity is tested in human HepG2 cells. In some embodiments, the bioactivity is tested in the liver of insulin-resistant and diabetic mice.

In some embodiments, the bioactivity is enhanced phosphorylation of Pdk1, Akt, Foxo1 and AS160. In some embodiments, the bioactivity is tested in the liver. In some embodiments, the bioactivity is tested in the skeletal muscle.

In some embodiments, the bioactivity is enhanced Glut4 expression. In some embodiments, the bioactivity is tested in mouse liver AML-12 cells. In some embodiments, the bioactivity is tested in the liver of insulin-resistant and diabetic mice.

In some embodiments, the bioactivity is activation and/or restoration of insulin signaling in a subject in insulin-resistant state. In some embodiments, the subject is characterized by significant levels of circulating insulin. In some embodiments, the insulin-resistant state is characterized by reduced level and/or activity of phosphorylated insulin receptor in the subject. In some embodiments, the subject has diabetes, and/or diabetes associated disease, disorders, or conditions.

In some embodiments, the bioactivity is enhanced glucose uptake. In some embodiments, the cells are liver cells and skeletal muscle cells. In some embodiments, the bioactivity is reduction of serum insulin level. In some embodiments, the bioactivity is tested in insulin-resistant and diabetic mice.

Identification and/or Characterization of Compounds and/or Compositions

In some embodiments, the present disclosure provides methods for identifying and/or characterizing a compound and/or a composition as described herein. In some embodiments, such a method comprises steps of testing a plurality of samples, each of which comprises a compound of any one of formulas (1)-(3), or a pharmaceutically acceptable salt, prodrug, or isomer thereof, for bioactivity therein; and determining presence and/or level of said bioactivity in one or more such samples. In some embodiments, a provided method comprises detecting said bioactivity associated with presence and/or level of a compound of any one of formulas (1)-(3), or a pharmaceutically acceptable salt, prodrug, or isomer thereof. In some embodiments, a provided method comprises a step of identifying and/or characterizing a particular compound of any one of formulas (1)-(3), or a pharmaceutically acceptable salt, prodrug, or isomer thereof, by detecting said bioactivity of the compound.

In some embodiments, the bioactivity is inhibition of glucose production. In some embodiments, the bioactivity is tested in HepG2 cells. In some embodiments, the bioactivity is tested in H4IIE cells.

In some embodiments, the bioactivity is reduction of serum HbA1c level. In some embodiments, the bioactivity is tested in insulin-resistant and diabetic mice.

In some embodiments, the bioactivity is enhanced glucose tolerance. In some embodiments, the bioactivity is tested in insulin-resistant and diabetic mice.

In some embodiments, the bioactivity is inhibition of G6pc expression. In some embodiments, the bioactivity is tested in AML-12 cells. In some embodiments, the bioactivity is tested in AML-12 cells stimulated with diabetic stimuli. In some embodiments, the bioactivity is tested in human HepG2 cells. In some embodiments, the bioactivity is tested in the liver of insulin-resistant and diabetic mice.

In some embodiments, the bioactivity is enhanced phosphorylation of Pdk1, Akt, Foxo1, and AS160. In some embodiments, the bioactivity is tested in the liver. In some embodiments, the bioactivity is tested in the skeletal muscle.

In some embodiments, the bioactivity is enhanced Glut4 expression. In some embodiments, the bioactivity is tested in mouse liver AML-12 cells. In some embodiments, the bioactivity is tested in the liver of insulin-resistant and diabetic mice.

In some embodiments, the bioactivity is activation and/or restoration of insulin signaling in a subject in insulin-resistant state. In some embodiments, the subject is characterized by significant levels of circulating insulin. In some embodiments, the insulin-resistant state is characterized by reduced level and/or activity of phosphorylated insulin receptor in the subject. In some embodiments, the subject has diabetes, and/or diabetes associated disease, disorders, or conditions.

In some embodiments, the bioactivity is enhanced glucose uptake into cells in a subject. In some embodiments, the bioactivity is enhanced glucose uptake into liver cells and skeletal muscle cells. In some embodiments, the bioactivity is reduction of serum insulin level. In some embodiments, the bioactivity is tested in insulin-resistant and diabetic mice.

Uses

The present disclosure provides that the compounds as described herein, for example compound 43, can mimic insulin to inhibit glucose production (see for example, Example 2); lower blood glucose and HbA1c levels, attenuate the development of hyperglycemia and improve glucose tolerance in insulin-resistant diabetic subjects (see for example, Example 3); inhibit G6pc expression in the liver of insulin-resistant diabetic subjects, and mimic but bypass insulin to inhibit G6pc expression in cultured mouse and human liver cells and potentiate insulin action (see for example, Example 4); mimic but bypass insulin to activate Pdk1 and Akt and enhance Foxo1 phosphorylation in the liver (see for example, Example 5); enhance Glut4 expression in the liver of insulin-resistant diabetic subjects, and mimic but bypass insulin to enhance Glut4 expression in mouse liver cells (see for example, Example 6), the phosphorylation of AS160 (a key event for GLUT4 transportation from cytosolic vesicles to plasma membrane to facilitate glucose uptake) in human liver cells (see for example, Example 8), and glucose uptake in mouse liver cells (see for example, Example 6); enhance and/or restore insulin signaling Pdk1/Akt/Foxo1 in the skeletal muscles of insulin-resistant diabetic subjects (see for example, Example 7), mimic by bypass insulin to activate Akt and enhance the phosphorylation of AS160 (a key event for GLUT4 transportation from cytosolic vesicles to plasma membrane) in skeletal muscle cells (see for example, Example 8), and potentiate insulin action to stimulate glucose uptake in skeletal muscle cells (see for example, Example 7); activate and/or restore insulin receptor (Insr) function in the skeletal muscle and liver of insulin-resistant diabetic subjects and in cultured mouse skeletal muscle and human liver cells (see for example, Example 8); and attenuate hyperinsulinemia without impairing kidney function and/or resulting in liver damage (Example 9). Accordingly, the present disclosure clearly demonstrates that the compounds as described herein are useful for modulating glucose metabolism and treating an insulin-related disorder as described herein.

In some embodiments, the present disclosure provides methods for modulating glucose metabolism and/or treating glucose metabolism disorders, comprising administering a therapeutically effective amount of a compound of any one of formulas (1)-(3), or a pharmaceutically acceptable salt, prodrug, or isomer thereof. In some embodiments, glucose metabolism disorders involve a blood glucose level which is not within the normal range. In some embodiments, glucose metabolism disorders relate to defective glucose uptake and/or transport. In some embodiments, glucose metabolism disorders are Diabetes Mellitus, glyceraldehyde-3-phosphate dehydrogenase deficiency, glycosuria, hyperglycemia, hyperinsulinism, or hypoglycemia.

In some embodiments, the present disclosure provides methods for treating disorders of glucose transport, comprising administering a therapeutically effective amount of a compound of any one of formulas (1)-(3), or a pharmaceutically acceptable salt, prodrug, or isomer thereof. In some embodiments, disorders of glucose transport are glucose-galactose malabsorption, Fanconi-Bickel syndrome, or De Vivo disease (GLUT1 deficiency syndrome (GLUT1DS)).

In some embodiments, the present disclosure provides methods for enhancing AS160 phosphorylation for translocation of glucose transporter proteins (GLUTs) from cytosolic vesicles to plasma membrane for glucose uptake, comprising administering a therapeutically effective amount of a compound of any one of formulas (1)-(3), or a pharmaceutically acceptable salt, prodrug, or isomer thereof.

In some embodiments, the present disclosure provides methods for enhancing glucose uptake in both liver and skeletal muscles, comprising administering a therapeutically effective amount of a compound of any one of formulas (1)-(3), or a pharmaceutically acceptable salt, prodrug, or isomer thereof.

In some embodiments, the present disclosure provides methods for treating an insulin-related disorder, comprising administering a therapeutically effective amount of a compound of any one of formulas (1)-(3), or a pharmaceutically acceptable salt, prodrug, or isomer thereof. In some embodiments, the insulin-related disorders are selected from the group consisting of pre-diabetes, type I diabetes, type II diabetes, hypoglycemia, hyperglycemia, insulin resistance, secretory dysfunction, loss of pancreatic β-cell function, and loss of pancreatic β-cells. In some embodiments, the patients of insulin-related disorders are non-insulin dependent patients having insulin-related disorders.

In some embodiments, the present disclosure provides methods for treating insulin resistance disorder comprising administering a therapeutically effective amount of a compound of any one of formulas (1)-(3), or a pharmaceutically acceptable salt, prodrug, or isomer thereof. Certain examples of insulin resistance disorders are described above. In some embodiments, provided methods are for treating Type II diabetes, hyperinsulinemia, hyperproinsulinemia, retinopathy, neuropathy, or nephropathy. In some embodiments, provided methods attenuate hyperinsulinemia without impairing kidney function and/or resulting in liver damage.

In some embodiments, the present disclosure provides methods for treating obesity comprising administering a therapeutically effective amount of a compound of any one of formulas (1)-(3), or a pharmaceutically acceptable salt, prodrug, or isomer thereof.

In some embodiments, the present disclosure provides methods for treating diabetes, comprising administering a therapeutically effective amount of a compound of any one of formulas (1)-(3), or a pharmaceutically acceptable salt, prodrug, or isomer thereof. In some embodiments, the diabetes is type I diabetes. In some embodiments, the diabetes is type II diabetes.

In some embodiments, the present disclosure provides methods for treating hyperglycemia comprising administering a therapeutically effective amount of a compound of any one of formulas (1)-(3), or a pharmaceutically acceptable salt, prodrug, or isomer thereof.

In some embodiments, the present disclosure provides methods for inhibiting glucose production, comprising administering a compound of any one of formulas (1)-(3), or a pharmaceutically acceptable salt, prodrug, or isomer thereof.

In some embodiments, the present disclosure provides methods for reducing serum HbA1c level, comprising administering a compound of any one of formulas (1)-(3), or a pharmaceutically acceptable salt, prodrug, or isomer thereof.

In some embodiments, the present disclosure provides methods for increasing glucose tolerance, comprising administering a compound of any one of formulas (1)-(3), or a pharmaceutically acceptable salt, prodrug, or isomer thereof.

In some embodiments, the present disclosure provides methods for inhibiting G6pc expression, comprising administering a compound of any one of formulas (1)-(3), or a pharmaceutically acceptable salt, prodrug, or isomer thereof.

In some embodiments, the present disclosure provides methods for enhancing phosphorylation of Pdk1, Akt, and Foxo1 in the liver and/or in the skeletal muscle, comprising administering a compound of any one of formulas (1)-(3), or a pharmaceutically acceptable salt, prodrug, or isomer thereof.

In some embodiments, the present disclosure provides methods for increasing Glut4 expression, comprising administering a compound of any one of formulas (1)-(3), or a pharmaceutically acceptable salt, prodrug, or isomer thereof.

In some embodiments, the present disclosure provides methods for activating and/or restoring insulin signaling in a subject in insulin-resistant state, comprising administering a compound of any one of formulas (1)-(3), or a pharmaceutically acceptable salt, prodrug, or isomer thereof. In some embodiments, the subject is characterized by significant levels of circulating insulin. In some embodiments, the insulin-resistant state is characterized by reduced level and/or activity of phosphorylated insulin receptor in the subject. In some embodiments, the subject has diabetes, and/or diabetes associated disease, disorders or conditions. In some embodiments, the subject has type II diabetes.

In some embodiments, the present disclosure provides methods for enhancing glucose uptake into cells in a subject, comprising administering a compound of any one of formulas (1)-(3), or a pharmaceutically acceptable salt, prodrug, or isomer thereof. In some embodiments, the cells are skeletal muscle cells.

It has been shown that Compound #43 can mimic but bypass insulin to activate insulin receptor signaling in the liver and skeletal muscle, and can restore insulin receptor function, even in insulin-resistant diabetic subjects. These observations suggests that compound #43 can be used for the treatment of diseases or syndromes characterized by defective insulin signaling, such as polycystic ovary syndrome (PCOS), Alzheimer's disease (AD) and sarcopenia.

In some embodiments, the present disclosure provides methods for treating polycystic ovary syndrome (PCOS) comprising administering a therapeutically effective amount of a compound of any one of formulas (1)-(3), or a pharmaceutically acceptable salt, prodrug, or isomer thereof. PCOS is a hormone imbalance that can cause irregular periods, unwanted hair growth, and acne. Young women with PCOS often have elevated insulin levels which can cause the ovaries to make more androgen hormones, resulting in increased body hair, acne, and irregular or few periods. Having PCOS can cause insulin resistance and the development of type 2 diabetes. Metformin is a medication often prescribed for women with PCOS to improve insulin sensitivity and prevent the development of type 2 diabetes. The results demonstrate that compound #43 is more potent than metformin in the inhibition of glucose production in cultured liver cells, and can restore insulin receptor function in insulin-resistant diabetic mice. Thus, Compound #43 can be potentially useful for the treatment of PCOS.

In some embodiments, the present disclosure provides methods for treating Alzheimer's disease (AD) comprising administering a therapeutically effective amount of a compound of any one of formulas (1)-(3), or a pharmaceutically acceptable salt, prodrug, or isomer thereof. Brain insulin signaling is important for learning and memory, and insulin resistance in the brain is a major risk factor for AD. The restoration of insulin signaling has emerged as a potential therapy for AD (White M F, Science 2003; 302:1710-1; De Felice D G et al, Alzheimer's & Dementia 2014; 10: S26-S32). In view of the results above showing that Compound #43 exhibited insulin-like activity and was able to restore insulin receptor function in insulin-resistant subjects, it can be potentially useful for the treatment of AD.

In some embodiments, the present disclosure provides methods for treating sarcopenia comprising administering a therapeutically effective amount of a compound of any one of formulas (1)-(3), or a pharmaceutically acceptable salt, prodrug, or isomer thereof. Sarcopenia is characterized by the progressive loss of skeletal muscle mass with increasing age, leading to decreased muscle strength, decreased mobility and function, increased fatigue, an elevated risk of fall-related injury, and, often, frailty (Candow and Chilibeck, 2005; Sakuma and Yamaguchi, 2012). Recent advances in muscle biology have revealed that insulin signaling (Insr/PI3K/Akt) is critical for the synthesis of muscle protein, and the inhibition of muscle protein degradation (through Akt/Foxo1-mediated inhibition of the expression of two atrophy genes Fbxo32 and Trim63). Optimal insulin signaling attenuates muscle wasting processes, including sarcopenia (Glass and Roubenoff, 2010; Ryall et al., 2008; Sakuma and Yamaguchi, 2012). As such, stimulators of insulin signaling, amino acid supplements (to improve protein synthesis) and inhibitors of proteasome protein degradation are emerging as new strategies for the treatments of sarcopenia. The insulin-like activity of Compound #43 in the activation of Insr/Pdk1/Akt/Foxo1 signaling in skeletal muscle even in insulin-resistant diabetic mice, as described herein, suggests the potential use of this compound for treating atrophic conditions in muscles.

The present disclosure also teaches that provided compounds likely enhance mitochrodrial function, and are therefore useful for treating mitochrodrial diseases and/or dysfunction. In some embodiments, the present disclosure provides methods for treating mitochondria-associated diseases (e.g., caused by dysfunctional mitochondria), comprising administering a therapeutically effective amount of a compound of any one of formulas (1)-(3), or a pharmaceutically acceptable salt, prodrug, or isomer thereof. In some embodiments, mitochondria-associated diseases can be degenerative diseases (e.g., cancer, cardiovascular disease and cardiac failure, type 2 diabetes, Alzheimer's and Parkinson's diseases, fatty liver disease, cataracts, osteoporosis, muscle wasting, sleep disorders and inflammatory diseases such as psoriasis, arthritis and colitis). In some embodiments, the present disclosure provides methods for enhancing mitochondrial function, comprising administering a therapeutically effective amount of a compound of any one of formulas (1)-(3), or a pharmaceutically acceptable salt, prodrug, or isomer thereof.

In some embodiments, the present disclosure provides methods for enhancing gluconeogenesis in the brain, comprising administering a therapeutically effective amount of a compound of any one of formulas (1)-(3), or a pharmaceutically acceptable salt, prodrug, or isomer thereof. In some embodiments, provided methods increase glucose uptake in the brain. In some embodiments, provided methods are for maintaining or restoring brain functions including memory and learning.

Combination Therapy

In some embodiments, the present disclosure provides use of the compounds and/or compositions as described herein for combination therapy of a disease, disorder, or condition as described herein. In some embodiments, the present disclosure provides methods for treating patients with a disease, disorder, or condition, who have received, are receiving, or will receive one or more different therapies for said disease, disorder, or condition, wherein the methods comprise administering a therapeutically effective amount of a compound of any one of formulas (1)-(3), or a pharmaceutically acceptable salt, prodrug, or isomer thereof.

In some embodiments, one or more therapies for patients with insulin-related disorders are selected from the group consisting of insulin therapy, for example, for type I diabetes; diet and exercise, for example, for incipient type II diabetes; oral antidiabetic agents, for example, for early stage type II diabetes; metformin; insulin secretagogues, for example, sulfonylureas; glitazones; long-acting basal insulin; intermediate acting insulin; and short (rapid) acting insulin. In some embodiments, insulin therapy involves administration subcutaneously (SC), intravenously, and/or by inhalation. In some embodiments, one or more therapies for patients with insulin-related disorders may be therapies currently under development, for example, insulin-fumaryl diketopiperazine (FDKP).

EXAMPLES

Example 1: Synthesis of Compounds #43, #50, #53, #69, #70, and #68

1a. Synthesis of Adenosine, 5'-Se-methyl-5'-selino-, 2',3'-diacetate (Compound #43)

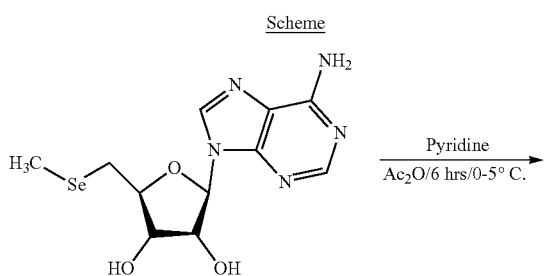

-continued

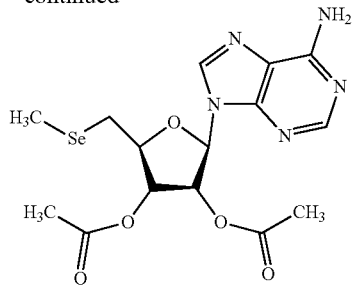

Synthetic procedure: 5'-Se-methyl-5'-seleno-Adenosine (1.0 gr, 0.0029 mole, 1.0 mole eq.) and anhydrous pyridine (10 ml) were placed in an oven dried, 50 ml three neck flask, equipped with a dropping funnel, inert gas inlet/outlet and a thermometer. The reaction set was placed in an ice/salt bath and agitation was initiated. When the temperature of the solution dropped to 0° C., acetic anhydride (10 ml, 0.105 mole, 36.47 mole eq.) was added drop-wise for 15 minutes and the temperature of the reaction mixture was maintained below 5° C. during acetic anhydride addition. The reaction mixture was stirred for 6 hours at 5-10° C. Quenched the excess acetic anhydride by adding ice-cold water (100 ml), and then pH adjusted to by adding 10 wt % NaHCO$_3$ aqueous solution. The aqueous mixture was extracted with ethyl acetate (2×100 ml). The combined ethyl acetate extracts are dried over anhydrous Na$_2$SO$_4$ (1 gr), filtered into a 250 ml round-bottomed flask. Concentrated the filtrate to dryness under reduced pressure at 35-40° C. to give the crude product as a pale yellow syrupy liquid, then pure product was obtained as off-white crystals (1.12 gr, Yield: 90.3%, Purity by HPLC: >99%) by passing through a silica gel column with a mixture of ethyl acetate and hexanes (1:3 v/v).

1b. Synthesis of Adenosine, 5'-S-methyl-5'-thio-, 2',3'-diacetate (Compound #68)

Scheme

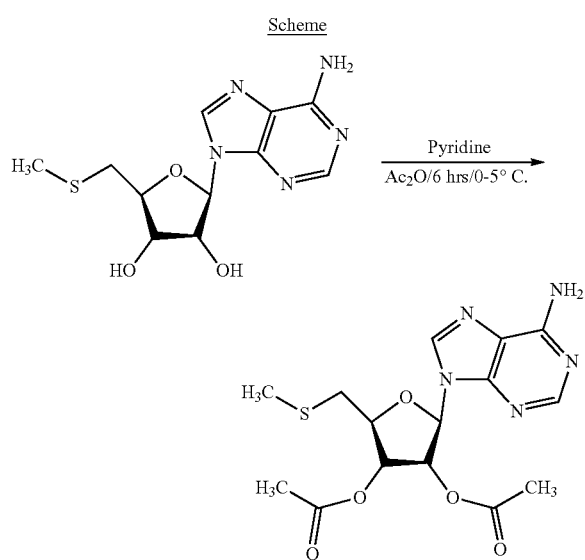

Synthetic procedure: 5'-S-methyl-5'-thio-Adenosine (1.0 gr, 0.0033 mole, 1.0 mole eq.) and anhydrous pyridine (10 ml) were placed in an oven dried, 50 ml three neck flask, equipped with a dropping funnel, inert gas inlet/outlet and a thermometer. The reaction set was placed in an ice/salt bath and agitation was initiated. When the temperature of the solution dropped to 0° C., acetic anhydride (10 ml, 0.105 mole, 31.8 mole eq.) was added drop-wise for 15 minutes and the temperature of the reaction mixture was maintained below 5° C. during acetic anhydride addition. The reaction mixture was stirred for 6 hours at 5-10° C. Quenched the excess acetic anhydride by adding ice-cold water (100 ml), and then pH adjusted to 7 by adding 10 wt % NaHCO$_3$ aqueous solution. The aqueous mixture was extracted with ethyl acetate (2×100 ml), The combined ethyl acetate extracts are dried over anhydrous Na$_2$SO$_4$ (1 gr), filtered into a 250 ml round-bottomed flask. Concentrated the filtrate to dryness under reduced pressure at 35-40° C. to give the crude product as a pale yellow syrupy liquid, then pure product was obtained as off-white crystals (1.08 gr, Yield: 87%, Purity by HPLC: >99%) by passing through a silica gel column with a mixture of ethyl acetate and hexanes (1:3 v/v).

1c. Synthesis of Adenosine, 5'-Se-methyl-5'-selino-, 2',3'-dipropionate (Compound #69)

Scheme

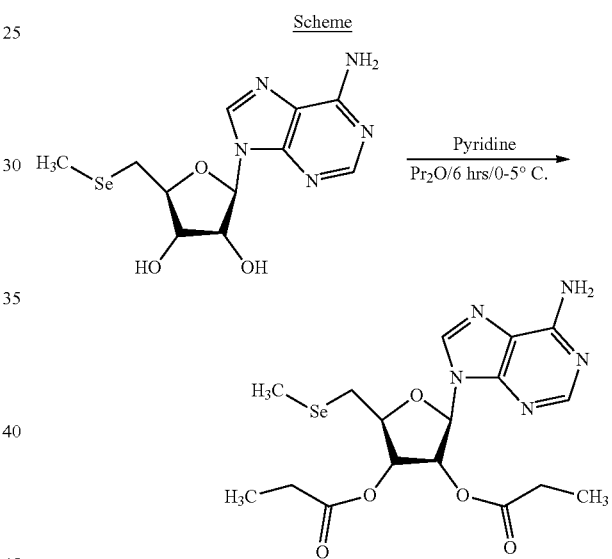

Synthetic procedure: 5'-Se-methyl-5'-seleno-Adenosine (1.0 gr, 0.0029 mole, 1.0 mole eq.) and anhydrous pyridine (10 ml) were placed in an oven dried, 50 ml three neck flask, equipped with a dropping funnel, inert gas inlet/outlet and a thermometer. The reaction set was placed in an ice/salt bath and agitation was initiated. When the temperature of the solution dropped to 0° C., propionic anhydride (10 ml, 0.078 mole, 27.0 mole eq.) was added drop-wise for 15 minutes and the temperature of the reaction mixture was maintained below 5° C. during propionic anhydride addition. The reaction mixture was stirred for 6 hours at 5-10° C. Quenched the excess propionic anhydride by adding ice-cold water (100 ml), and then pH adjusted to 7 by adding 10 wt % NaHCO$_3$ aqueous solution. The aqueous mixture was extracted with ethyl acetate (2×100 ml). The combined ethyl acetate extracts are dried over anhydrous Na$_2$SO$_4$ (1 gr), filtered into a 250 ml round-bottomed flask. Concentrated the filtrate to dryness under reduced pressure at 35-40° C. to give the crude product as a pale yellow syrupy liquid, then pure product was obtained as off-white crystals (1.18 gr, Yield: 89.3%, Purity by HPLC: >99%) by passing through a silica gel column with a mixture of ethyl acetate and hexanes (1:3 v/v).

1d. Synthesis of Adenosine, 5'-Se-methyl-5'-selino-, 2',3'-dibutanoate (Compound #70)

Scheme:

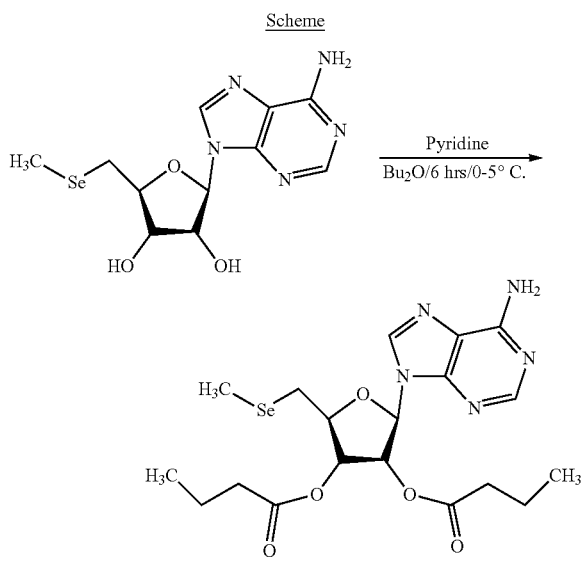

Synthetic procedure: 5'-Se-methyl-5'-seleno-Adenosine (1.0 gr, 0.0029 mole, 1.0 mole eq.) and anhydrous pyridine (10 ml) were placed in an oven dried, 50 ml three neck flask, equipped with a dropping funnel, inert gas inlet/outlet and a thermometer. The reaction set was placed in an ice/salt bath and agitation was initiated. When the temperature of the solution dropped to 0° C.; butyric anhydride (0.10 ml, 0.078 mole, 27.0 mole eq.) was added drop-wise for 15 minutes and the temperature of the reaction mixture was maintained below 5° C. during butyric anhydride addition. The reaction mixture was stirred for 6 hours at 5-10° C. Quenched the excess butyric anhydride by adding ice-cold water (100 ml), and then pH adjusted to 7 by adding 10 wt % $NaHCO_3$ aqueous solution. The aqueous mixture was extracted with ethyl acetate (2×100 ml). The combined ethyl acetate extracts are dried over anhydrous $Na_2SO_4$ (1 gr), filtered into a 250 ml round-bottomed flask. Concentrated the filtrate to dryness under reduced. pressure at 35-40° C. to give the crude product as a pale yellow syrupy liquid, then pure product was obtained as off-white crystals (1.20 gr, Yield: 85.7%, Purity by HPLC: >99%) by passing through a silica gel column with a mixture of ethyl acetate and hexanes (1:3 v/v).

1e. Synthesis of Adenosine, 5'-Se-methyl-5'-selino-, cyclic 2',3'-carbonate (Compound #50)

Scheme

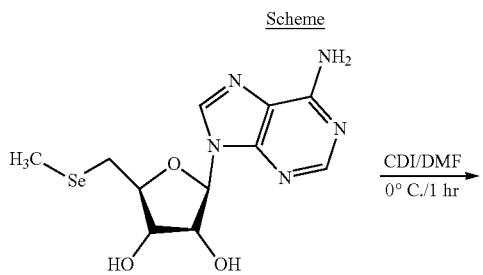

-continued

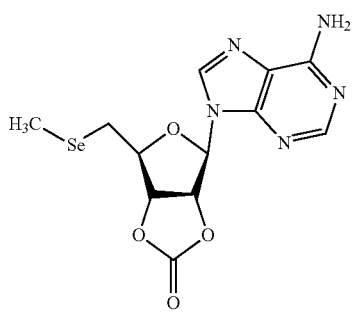

Synthetic procedure: 5'-Se-methyl-5'-seleno-Adenosine (1.0 gr, 0.0029 mole, 1.0 mole eq.) and anhydrous dimethylformamide (20 ml) were placed in an oven dried, 50 ml three neck flask, equipped with a dropping funnel, inert gas inlet/outlet and a thermometer. The reaction set was placed in an ice/salt bath and agitation was initiated. When the temperature of the solution dropped to 0° C., carbonyldiimidazole (CDI, 0.57 gr, 0.0035 mole, 1.21 mole eq.) was added at below 5° C. The reaction mixture was slowed warmed to the room temperature, and then stirred the reaction mixture for 4 hours at the same temperature under argon gas atmosphere. The solvent was removed under reduced pressure to give the residue, it was dissolved in a mixture of chloroform (5 ml) and ethanol (few drops) to get clear solution, washed the organic layer with 1% aq. acetic acid solution (2×1 ml), dried over anhydrous $Na_2SO_4$ (1 gr), filtered into a 250 ml round-bottomed flask. Concentrated the filtrate to dryness under reduced pressure at 25-30° C. to give the crude product as a pale yellow syrupy liquid. Dissolved the crude product in a mixture of ethanol/water mixture (1:1 v/v), and then concentrated to dryness under reduced pressure at 45-50° C. to give a residue, hexanes (25 ml) were added and stirred for 10 minutes, and then concentrated to dryness under reduced pressure at 30-35° C. to yield the desired product as a off-white crystals (1.02 gr, Yield: 95.3%, Purity by HPLC: >99%).

1f. Synthesis of a region-isomeric mixture of Adenosine, F—Se-methyl-F-seleno-, 2'-morpholinocarbamate and Adenosine, 5'-Se-methyl-F-seleno-, 3'-morpholinocarbamate (Compound #53)

Scheme

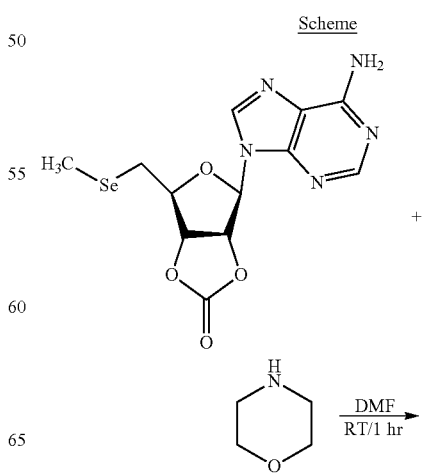

-continued

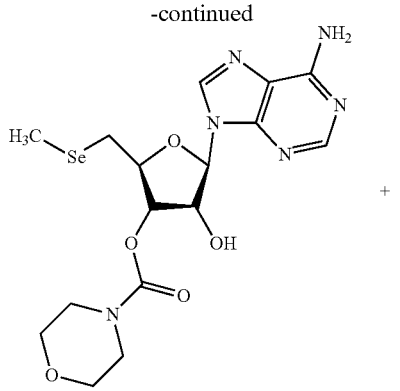

+

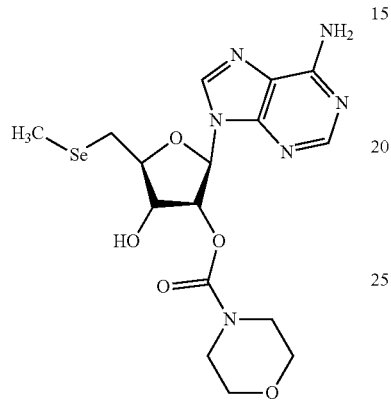

Synthetic procedure: Adenosine, 5'-Se-methyl-5'-seleno-, cyclic 2',3'-carbonate (1.0 gr, 0.0027 mole, 1.0 mole eq.) and anhydrous dimethylformamide (10 ml) were placed in an oven dried, 50 ml three neck flask, equipped with a dropping funnel, inert gas inlet/outlet and a thermometer. Morpholine (0.26 gr, 0.0029 mole, 1.1 mole eq.) was added at 20-25° C. Stirred the reaction mixture for 1 hour at room temperature, and then concentrated to dryness under reduced pressure at 45-50° C. to give a residue, hexanes (25 ml) were added and stirred for 10 minutes to precipitate the desired region-isomeric mixture product as a off-white solid (1.12 gr, Yield: 91%, Purity by HPLC: >99%).

Example 2

Synthetic compounds listed in Table 1 were tested in cell culture (in vitro) for effects on glucose production and cell viability in the examples described herein. In particular, the cells tested were human hepatoma HepG2 and rat liver H4IIE liver cells.

TABLE 1

| Abbreviated compound name | Compound name | Compound structure | Mol. Wt. | Solvent |
|---|---|---|---|---|
| Compound-C | 5'-Methylselenoadenosine | 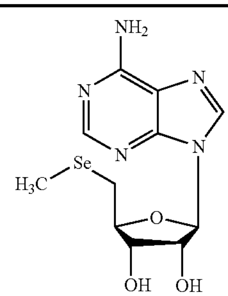 | 344.22 | DMSO |
| Compound-D | 5'-Selenoadenosyl-homocysteine | 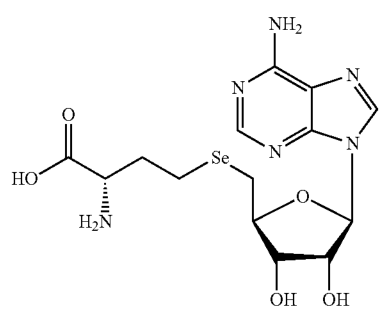 | 431.30 | DMSO |
| Compound-E | γ-L-glutamyl-Se-methyl-L-selenocysteine | 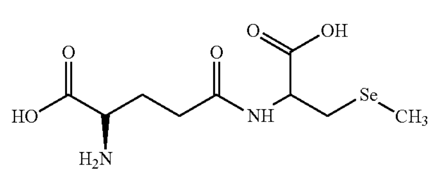 | 311.19 | Water |

TABLE 1-continued

| Abbreviated compound name | Compound name | Compound structure | Mol. Wt. | Solvent |
|---|---|---|---|---|
| Compound #43 (Diacetyl ester of Compound-C) | Diacetyl ester of methylselenoadenosine | 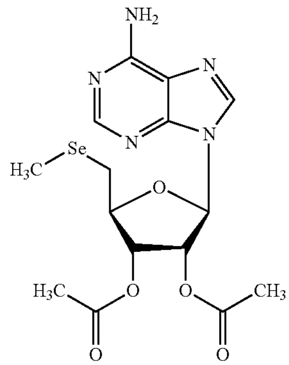 | 428.30 | DMSO |
| Compound #50 | Cyclic carbonate of methylselenoadenosine | 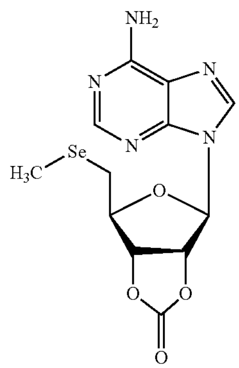 | 370.22 | DMSO |
| Compound #53 | Carbamate analog of methylselenoadenosine with morpholine | | 457.34 | DMSO |
| Compound #57 | Adenosine | 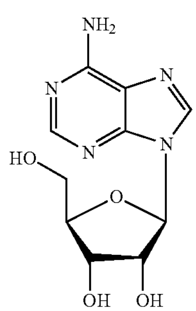 | 267.24 | DMSO |

TABLE 1-continued

| Abbreviated compound name | Compound name | Compound structure | Mol. Wt. | Solvent |
|---|---|---|---|---|
| Compound #59 (a cell-permeable adenylyl cyclase inhibitor) | 2',5'-Dideoxyadenosine | 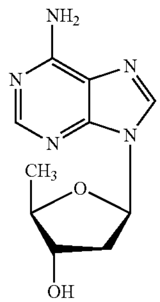 | 235.24 | DMSO |
| Compound #60 | 5'-Deoxyadenosine | 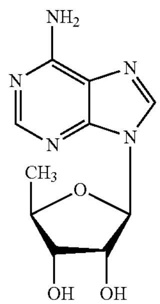 | 251.24 | Water |
| Compound #61 (an adenylyl cyclase inhibitor) | 9-(tetrahydrofuran-2-yl)-9h-purin-6-amine (SQ 22,536) | 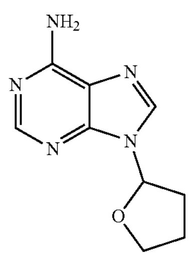 [SMILES: Nc1ncnc2c1ncn2C1CCCO1] | 205.21 | DMSO |
| Compound #62 | Adenine | 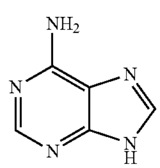 | 135.12 | DMSO |
| Compound #63 | Nicotinamide adenine dinucleotide (NAD) | 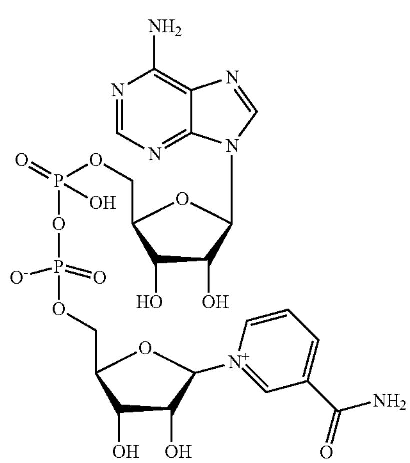 | 664.43 | Water |

TABLE 1-continued

| Abbreviated compound name | Compound name | Compound structure | Mol. Wt. | Solvent |
|---|---|---|---|---|
| Compound #64 | S-(5'-Adenosyl)-L-methionine iodide (SAM) | 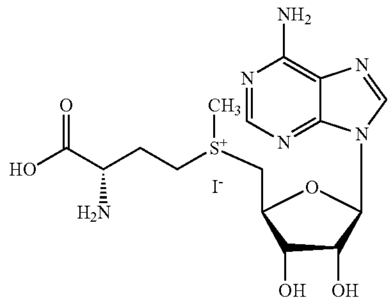 | 526.35 | Water |
| Compound #68 (Sulfur analog of Compound #43) | Diacetyl ester of methylthiooadenosine | 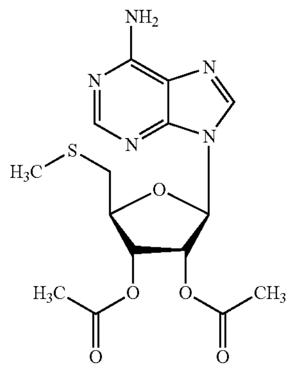 | 381.40 | DMSO |
| Compound #69 (Dipropanoyl ester of Compound-C) | Dipropanoyl ester of methylselenoadenosine | 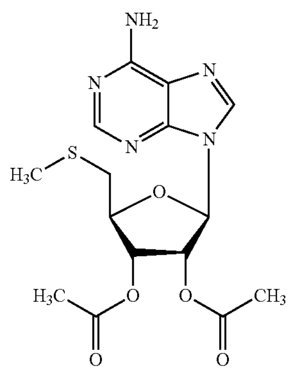 | 456.35 | DMSO |
| Compound #70 (Dibutanoyl ester of Compound-C) | Dibutanoyl ester of methylselenoadenosine | 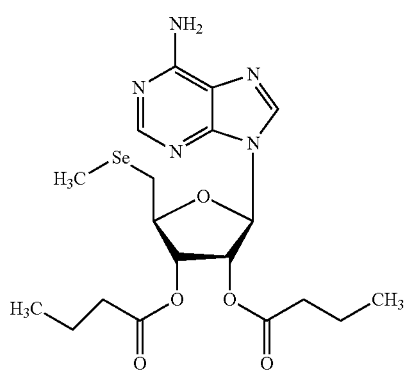 | 484.40 | DMSO |

Materials and Methods

Cell Lines and Compounds

The human hepatoma HepG2 and rat hepatoma H4IIE cells were purchased from the American Type Culture Collection (ATCC, Manassas, Va.). HepG2 cells and H4IIE cells were cultured in Eagle's Minimum Essential Medium (EMEM) supplemented with 10% FBS.

Compound #43 and other compounds listed in Table 1 were either synthesized or obtained from commercial sources (where available). The purities of all tested compounds were verified to be ≥99%, as determined by HPLC. All these compounds were either dissolved in DMSO or in water to obtain a 126.7 or 12.67 mM stock solution for experiments. Metformin and insulin were purchased from Sigma.

Glucose Production Assay

Equal numbers of Human HepG2 or rat H4IIE cells ($1$-$1.5 \times 10^5$ cells/well) were seeded on 96 well plates in 10% FBS-containing media for 24 hr. Cells were then washed twice with PBS, and treated with various concentrations of compounds, metformin or insulin in 100 µl of glucose production media (glucose-free, phenol red-free DMEM media supplemented with 20 mM sodium lactate, 2 mM sodium pyruvate and 5 mM HEPES) at 37° C. for 24 hr (H4IIE cells only) or 48 hr (HepG2 cell only). Cells were also incubated with 0.24% DMSO (the maximal volume of DMSO solvent used in the experiments).

After the above treatments, 50 µl of culture media were collected, and subjected to glucose analysis using Molecular Probes Amplex Red glucose assay kit (Cat #A22189) according to the manufacturer's protocol. Cell numbers or viability in the culture plate after the above compound treatments were determined using Promega's CellTiter96® AQueous One Solution Cell Proliferation Assay kits, according to the manufacturer's protocol and instructions. In brief, after removing 50 µl of culture media for glucose assay, cells were incubated with AQueous One solution (25 µl stock solution and 50 µl prewarmed PBS/per well) at 37° C. for 1 hour, and the absorbance of OD490 nm in each sample was determined by the Bio-Tek microplate reader. Cell viability in culture wells were determined by the subtraction of OD490 nm in cultured cells with the OD490 nm in plain culture media (without seeding of cells). Glucose production in the culture cells were obtained by normalizing the glucose concentration in culture media by cell viability in each well. At least 3 samples per each treatment were examined for the above analysis. Data are presented as Mean±SEM of those samples. Experiments were repeated at least twice.

The half maximal inhibitory concentration (IC50 values) of Compound #43 or metformin for the inhibition of glucose production were determined using the ED50 Plus v1.0 online software.

Results and Discussion

1. Effect of Insulin and Compound Solvent DMSO on Glucose Production in HepG2 Cells As shown in the left panel of FIG. 1, treatment with 10 nM and 100 nM insulin, respectively, resulted in a 20% and 30% reduction in glucose production in HepG2 cells while the compound solvent DMSO at the maximal volume used did not affect glucose levels in cultured HepG2 cells. These results suggest that HepG2 cells are responsive to insulin in the inhibition of glucose production, and the observed effects of the tested compounds on glucose production are not due to potential effects of DMSO. These results establish that HepG2 cells constitute an appropriate cell system for the screening of compounds having insulin-like activity and which can inhibit glucose production in liver cells.

2. Compound #43 can Mimic Insulin to Inhibit Glucose Production in HepG2 Cells

As shown in FIG. 1, incubation of HepG2 cells with Compound #43 at the tested doses under serum-free conditions resulted in a decrease in glucose levels in the culture media. The observed reduction in glucose production by HepG2 cells after treatment with compound #43 (3.8 µM) was comparable to that achieved when insulin (100 nM) was used, while higher doses of Compound #43 (7.6, 15.2 and 30.4 µM) were much more potent than 100 nM insulin. Furthermore, no significant decrease of cell viability was observed in the HepG2 cells after the treatment of Compound #43 at all tested doses (data not shown). These results suggest that Compound #43 is an insulin-mimetic that can inhibit glucose production in HepG2 cells.

3. Compound #43 on its Own Showed Higher Endpoint Potency than the Three Compound Combination, CDE, in the Inhibition of Glucose Production in HepG2 Cells Treatment of HepG2 cells with Compound CDE, at all tested doses, (1:1:1 ratio of C/D/E) also inhibited glucose production with a potency comparable to 100 nM insulin. Compound #43 at a dose of 3.8 µM was as potent as the CDE combination product (which contained 3.8 µM of each individual compound) in inhibiting glucose production in HepG2 cells. However, Compound #43 at a dose of 7.6 µM or higher was more potent than CDE in inhibiting glucose production in HepG2 cells. These results demonstrated that Compound #43 on its own showed higher endpoint potency than the three compound combination, CDE, in inhibiting glucose production in HepG2 cells. Noting that the selenium concentration in Compound CDE is three times higher than in Compound #43 at each dose point, these results might suggest that one or more structural features of Compound #43 in addition to its selenium molecule may be able, at least in certain circumstances, contribute to its activity.

4. Inhibition of Glucose Production in HepG2 is Abrogated when Sulfur is Substituted for Selenium Molecule in Compound #43

As shown in the right-hand panel of FIG. 1, treatment of cells with sulfur-bearing compounds, Compound #68 (the sulfur analog of Compound #43) or Compound #64 (SAM), as well as other listed non-selenium compounds had minimal effects in lowering glucose production in HepG2 cells. The striking difference in the inhibition of glucose production between Compound #43 and #68 demonstrates that the selenium molecule in Compound #43 contributes to its function in the inhibition of glucose production in HepG2 cells.

5. Differential Effect of Selenium Compounds on the Inhibition of Glucose Production in HepG2 Cells As described above, an equimolar mixture of the selenium-containing compounds C, D, and E (CDE) inhibited glucose production in human HepG2 cells at the indicated doses. Noting that the compound concentration indicated on the X-axis of FIG. 1 refers to the Se-concentration of each Se-containing compound in the mixture, the total Se-concentration is actually three-times higher than that is indicated on the X-axis. This was done to facilitate direct comparison of the mixture components with each of the single molecule candidates tested in those experiments.

If the inhibition of glucose production was solely due to selenium, then it might be expected that CDE, because it contains three-times more selenium than Compound #43, would produce a more robust response than the latter. That is clearly not the case.

FIG. 1 (the left-hand panel) shows that each of compounds C, D, 43, 50, 53, 69 and 70 inhibited glucose production, among which compound 43 was the most potent. Further, compound E was found to stimulate glucose production in HepG2 cells.

Taken together, these results suggests:
  (i) The selenium molecule in the compound is required for effective inhibition of glucose production (compare Compound #43 in the left-hand panel of FIG. 1 to its exact sulfur analog, Compound #68 in the right-hand panel).

(ii) However, the selenium molecule alone may not be sufficient for inhibiting glucose production (in some cases, selenium-containing, structurally similar compounds exhibited lower or opposite effect);

(iii) Increasing the concentration of selenium molecule alone may not enhance potency (selenium concentration of CDE is three-fold higher than that of Compound #43, yet is not as potent);

(iv) Among the compounds tested, Compound #43 exhibited the highest potency in inhibiting glucose production in liver cells.

6. Analysis of Structural Features of the Listed Selenium Compounds to Determine Chemical Groups which May Contribute to their Activity Comparison of Compounds C and D indicates that 5' methyl seleno group and 5' seleno homocysteine may provide similar inhibition of glucose production. Comparison of Compounds 43, 50, 53, 69, and 70 indicates that diacetyl ester at 2' and 3' position (#43) provides higher inhibition of glucose production than cyclic carbonate (Compound #50), morpholino carboxylate (#53), dipropanoyl ester (#69), and dibutanoyl ester (#70). Adenine, adenosine and several chemical variants of adenosine did not inhibit glucose production in HepG2 cells. Furthermore, two adenylyl cyclase inhibitors (#59 and 61) also did not inhibit glucose production, indicating that the action of Compound #43 in the inhibition of glucose production is unlikely due to a decrease in cellular AMP levels (Hardie D G. Cell Metabolism 2013: 17(3): 313-314). Together, the results suggest that one or more features, in addition to adenine and selenium molecule, may be able, at least in certain circumstances, to contribute to the activity.

7. Comparative Studies of Compound #43 and Metformin (a Well-Known Antidiabetic Drug) in the Inhibition of Glucose Production in HepG2 and Rat H4IIE Cells As described above, the robust inhibition of glucose production in HepG2 cells was observed after Compound #43 treatment. The effects of this compound were compared to the well-known anti-diabetic drug metformin. As described above and shown in the top panel of FIG. 2, a dose-dependent decrease of glucose levels in HepG2 cells following Compound #43 treatment was observed and the IC50 (the half maximal inhibitory concentration) value was 15.5 µM. As can be seen, metformin at a dose of 500 µM did not inhibit glucose production in HepG2 cells but instead showed some stimulatory effects. Higher doses of metformin (0.5-4 mM) showed cell toxicity on these cells (data not shown). These results demonstrate that Compound #43, similar to insulin, can inhibit glucose production in HepG2 cells.

Figure 2:
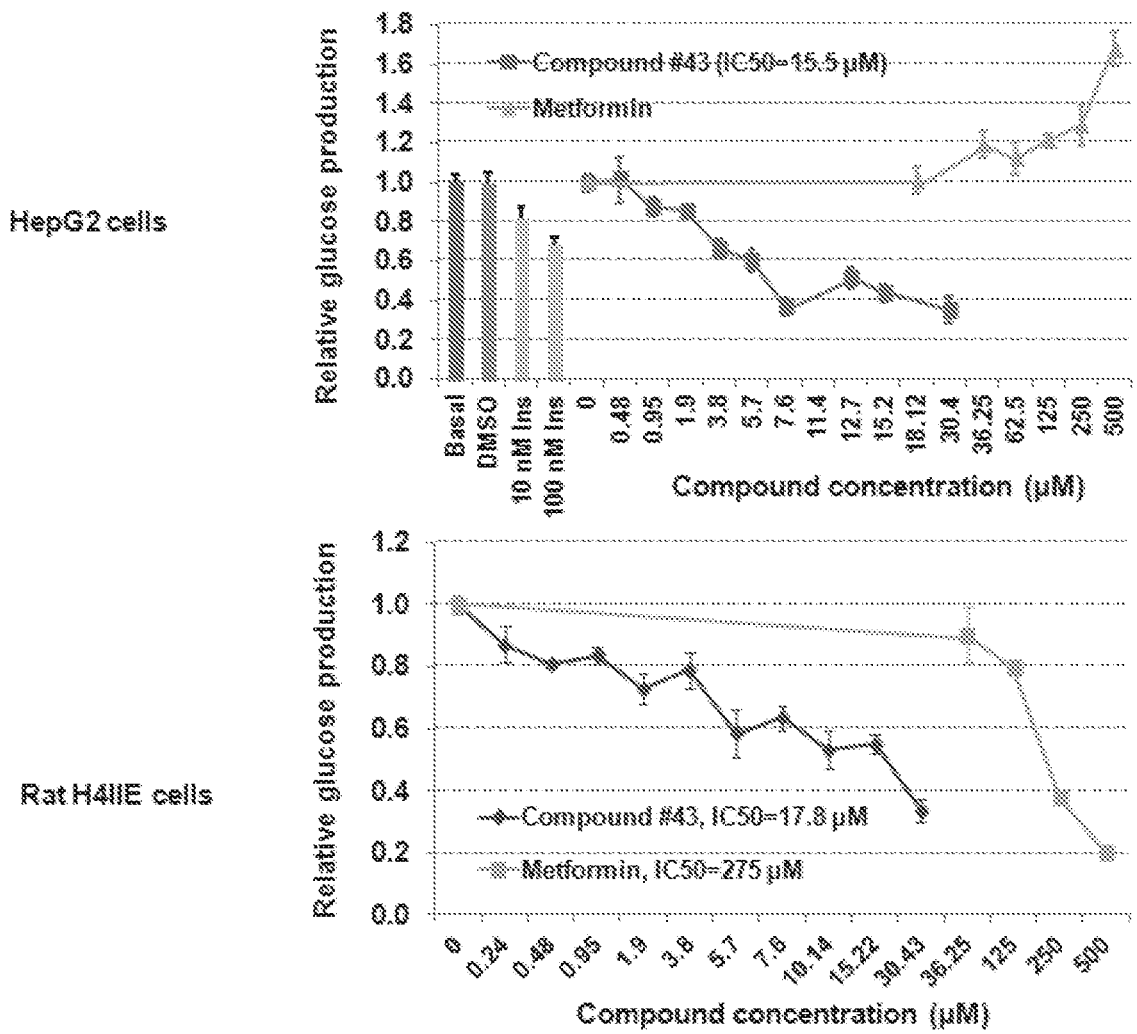
FIG. 2. Comparison of the potency of Compound #43 and metformin in both HepG2 and H4IIE cells. HepG2 cells were treated with 0.24% DMSO (the maximal volume of Compound #43 solvent), insulin, Compound #43 and metformin in serum-free glucose production media for 48 hr, while rat liver cells were treated for 24 hr. Glucose levels in culture media were normalized by cell number in each sample. Data are presented as mean±SEM of between 3 and 8 samples per group.

It has been reported that rat H4IIE liver cells can respond to metformin leading to lowered glucose production. Thus, this rat liver cell line was used to further confirm the inhibitory activity of Compound #43 on glucose production, and to compare the potency of Compound #43 with metformin. As shown in FIG. 2, treatment with Compound #43 and metformin, respectively, resulted in a dose-dependent decrease in glucose production in H4IIE cells under serum-free conditions. No toxic effect of these compounds was observed at the tested doses on cell viability (data not shown). The IC50 of Compound #43 was 17.8 µM, which is nearly identical to its IC50 in HepG2 cells. In contrast, metformin at a dose of 36.25 µM showed little or no inhibitory activity, and the IC50 of metformin in this experiment was 275 µM. These results suggest that Compound #43 is more potent (at least 15 times more potent) than metformin in the inhibition of glucose production in cultured rat liver cells.

In summary, Compounds #43, 50, 53, 69 and 70 all displayed activity in the inhibition of glucose production in cultured liver cells. However, Compound #43 was by far the most potent single compound tested with an inhibitor activity against glucose production which exceeded that of a high insulin dose (100 nM) in HepG2 cells.

Moreover, Compound #43 was demonstrated to be much more potent than the biguanide drug, metformin, in both liver cell lines tested. Metformin currently is the first-line drug used in the treatment of type 2 diabetes.

Example 3: Studies with Compound #43 and the Closely Related Seleno-Organic Compounds (#C, #50, #69 and #70), Together with the Sulfur Analog of Compound #43 (Compound #68) in the Regulation of Glucose and/or HbA1c Levels in the Bloodstream and in the Improvement of Glucose Tolerance in Insulin-Resistant and Diabetic Leptin Receptor (Lepr) Spontaneous Null Mutant Mice Materials and Methods
Compounds Compound #43, #C, #50, #68, #69 and #70 were synthesized in the Chemistry Laboratory of Alltech, Inc. The purities of all tested compounds were verified to be ≥99%, as determined by HPLC.

Animals 5-10 week-old male diabetic spontaneous mutation (leptin receptor mutation) $Lepr^{db/db}$ mice (C57BL/6J strain) were purchased from The Jackson Laboratory (Bar Harbor, Me.), and housed in a pathogen-free vivarium with free access to chow and water.

Chronic Treatments with Compound #43 and Other Compounds

Male $Lepr^{db/db}$ mice at 38 days of age were intraperitoneally (ip) injected daily with physiological saline (0.09% NaCl) containing 0.2% DMSO, Compound #C, Compound #50, Compound #68, and/or Compound #43 (25 µg selenium or sulfur equivalents of each compound per kilogram body weight, diluted in sterile physiological saline) for periods ranging from 43-90 days. Body weights of the above treated mice were recorded daily using a balance and any visible abnormal animal gross morphology and walking behavior were monitored daily. After the treatments, animals were fasted overnight and then subjected to blood glucose or HbA1c assays, glucose tolerance tests or tissue collections.

For comparative studies of any potential anti-diabetic effects of Compounds #43, #69 and #70, male $Lepr^{db/db}$ mice at 41 days of age were intraperitoneally (ip) injected daily with physiological saline (0.09% NaCl) containing 0.2% DMSO, Compound #43, Compound #69, or Compound #70 (25 µg selenium of each compound per kilogram body weight, diluted in sterile physiological saline). After the treatments for 43 days, animals were fasted overnight and then subjected to blood glucose and glucose tolerance tests. After daily treatments of these compounds for 90 days, sera from these animals were collected and then subjected to blood HbA1c assays.

Acute Treatment of Compound #43

After overnight fasting, 8-10-week-old $Lepr^{db/db}$ mice were intraperitoneally injected with physiological saline (0.09% NaCl) containing 0.2% DMSO, or Compound #43 (0.0054, 0.054, 0.54, or 5.4 mg Compound #43 (the compound stock was diluted in sterile physiological saline) per kilogram of body weight. Following the injection of saline or compound, mice were returned to their cages with free access to water but not chow for 1, 2, 3, 5 and 8 hr. At each time point after injection, a small drop of blood was collected from the tail of each mouse for glucose assay.

Additional 6-week old Lepr$^{db/db}$ mice under non-fasting conditions were intraperitoneally injected with physiological saline (0.09% NaCl) containing 0.2% DMSO, or a single dose of Compound #43 (5.4 mg compound/kg body weight). After injection, animals were returned back to their cages with free access to water and chow. After 24 hr, a small drop of blood from the mouse tail was collected for glucose assay.

Blood Glucose Assay

After treatment with physiological saline or compounds or after the injection of a bolus of glucose, a small drop of blood from each mouse was collected by snipping the mouse tail tip. Blood glucose levels were determined using a Glucometer with a maximum capability for glucose measurement of 600 mg/dL.

Glucose Tolerance Test

Glucose tolerance tests were performed as described previously (Li et al, *Int J Biol Sci* 2008; 4:29-36). Briefly, overnight-fasted Lepr$^{db/db}$ mice after saline or compound treatments were injected intraperitoneally with 2 grams/kg body weight of 20% D-glucose. Blood glucose levels at time 0 (immediately before the injection of glucose), 0.25, 0.5, 1 and 2 hours after injection of glucose were determined using a glucometer with a maximum glucose measurement capacity of 600 mg/dL. Because of this, blood glucose levels over 600 mg/dL were counted as 600 mg/dL in the data analysis.

Blood and Serum HbA1c Assays

After saline or compound treatments, a small drop of blood from the mouse tail was collected in an EDTA-coated eppendorf tube (to prevent blood coagulation) (Fisher Scientific), and then subjected to a HbA1c assay using the Crystal Chem's or Kamiya's mouse glycated hemoglobin A1c ELISA kit, according to the manufacturer's protocol. Also after the final treatments, mouse serum was collected and subjected to HbA1c assay using the Kamiya Biomeidcal Company's mouse HbA1c kit, according to the manufacturer's protocol.

Statistical Analysis

Where applicable, a Student's t-test was used to determine the statistical significance of difference between saline- and compound-treated groups, with a P value less than 0.05 being deemed significant. Data are presented as mean±SEM of the indicated numbers of mice in the figures.

Results and Discussion

Lepr$^{db/db}$ mice lack all known isoforms of the leptin receptor gene (Lepr). This homozygous mouse model is an aggressive Type II diabetic mouse model with impaired glucose tolerance, reduced insulin sensitivity, hyperglycemia and hyperinsulinemia. These mice display gross obesity at around 3 to 4 weeks of age, elevation of plasma insulin beginning at 10 to 14 days and hyperglycemia (i.e., high blood sugar levels) developed at about 4-8 weeks of age (Coleman D L. 1978 Diabetologia 14:141-8).

In vitro studies showed that Compound #43 can mimic but bypass insulin to inhibit glucose production with a much greater potency than closely related compounds such as Compound #C or #50. Furthermore, the sulfur-containing analog of Compound #43 (Compound #68) had little or no inhibitory effect on glucose production in HepG2 cells (FIGS. 1-2). Therefore, the insulin-resistant Lepr mouse is an ideal in-vivo model system to investigate the use of experimental compounds in potentially lowering glucose in the bloodstream and improving insulin sensitivity and glucose tolerance against a severe diabetic background.

1. Compound #43, the Most Potent Compound Among Three Tested Seleno-Organic Compounds (#C, #50, #43) Against Hyperglycemia in Lepr$^{db/db}$ Mice after Chronic Treatments The administration regimes of compounds were adopted to investigate the potential role of test compounds in the treatment of hyperglycemia, as displayed in Lepr$^{db/db}$ mice. Mice were administered treatments daily by intraperitoneal injection of Compounds around the onset of hyperglycemia (developed at about 4-8 week after birth). The three compounds (i.e., Compound #43, Compound #C and Compound #50, delivering identical concentrations of selenium) was injected daily for 43-52 days to investigate if these seleno-organic compounds have measureable effects against hyperglycemia in the insulin-resistant mice.

It was found that treatment with all tested compounds did not affect body weight gains in these mutant mice (data not shown), indicating that the tested compounds likely has little or no inhibitory effects on the abnormally increased appetite for consumption of food displayed in Lepr$^{db/db}$ mice. Also, there was no visible difference in animal gross morphology and walking behavior between saline-treated (control) and compound-treated Lepr$^{db/db}$ mice during the treatment period (data not shown). These results indicate that these compounds at the tested doses had no toxic effects on animal behavior or activity.

Among compounds #C, #50, and #43, treatment with Compounds #43 resulted in the most significant decrease, about 45% reduction compared to controls, of glucose levels in the bloodstream of Lepr$^{db/db}$ mice (see FIG. 3 left panel), even though the blood glucose levels in Compound #43-treated Lepr$^{db/db}$ mice were still higher than normal wild-type mice of the same age (about 100 mg/dL, data not shown). Furthermore, these results clearly demonstrate that Compound #43 can significantly reduce glucose levels in the bloodstream in this severe type II diabetes mouse model, indicating the potential of this compound for the prevention of hyperglycemia. In addition, these results provide good evidence for differential effects of selenoorganic compounds against hyperglycemia and show that Compound #43 is the most potent compound (among these three tested compounds) for the treatment of hyperglycemia.

Figure 3:
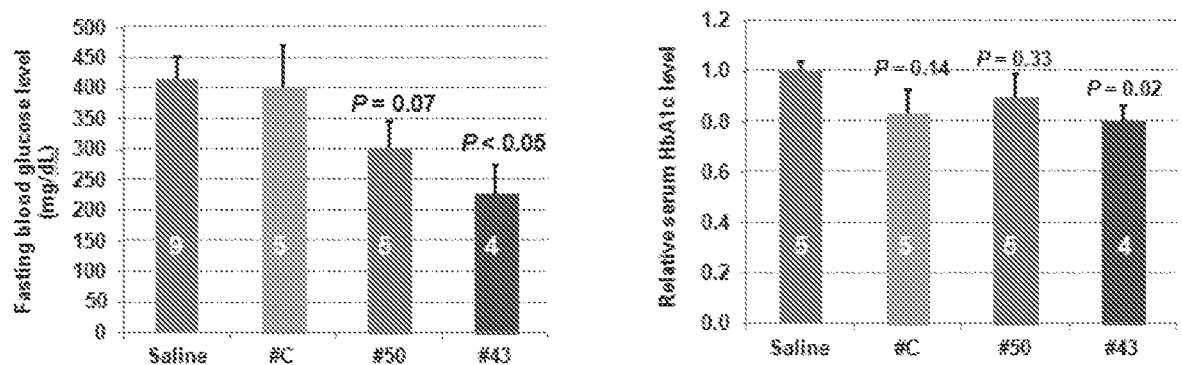
FIG. 3. Differential effects of Compound #C, #50 and #43 on blood glucose levels and serum HbA1c levels in $Lepr^{db/db}$ mice after chronic treatment. $Lepr^{db/db}$ mice were intraperitoneally injected with saline (containing 0.2% the compound solvent DMSO), Compound #C, #50 and #43 at the dose of 25 μg selenium of each compound per kilogram body weight daily starting 38 days of age. At the mouse age of day 81, the blood glucose level of overnight-fasting mice were determined using a glucometer. Serum HbA1c levels were determined on mice at 90 days of birth. The relative HbA1c levels were obtained after the HbA1c levels in Compound #C-, #50- and #43-treated mice were divided by the average HbA1c levels in saline-treated mice. Data are presented as mean±SEM of indicated number of animals. P values were derived by comparing treatments to the control/saline group.

In addition, sera were collected from Compound #C—, #50- and #43-treated Lepr$^{db/db}$ mice and subjected to an HbA1c test. HbA1c levels represent a longer-term index of blood glucose concentrations over the past 2 to 3 months, and the test is widely used in clinical medicine to monitor blood glucose level history in diabetic patients. As shown in FIG. 3, among compounds #C, #50 and #43, Compound #43 treatments resulted in the only significant decrease (about a 20% reduction) in serum HbA1c levels when compared to the saline-treated group. These results are consistent with the above observed differential effects of these three compounds on the fasting glucose levels in mice (the left panel in FIG. 3) and on the glucose production in vitro (HepG2 cells, FIG. 1).

Therefore, the results provide in vivo evidence that there exists a differential effect of seleno-organic compounds against hyperglycemia and that Compound #43 is the most potent compound among these three selenium-containing compounds (#C, #50, and #43) with a clear potential for the treatment of hyperglycemia in insulin-resistant subjects.

2. Replacement of the Selenium Molecule in Compound #43 by a Sulfur Molecule at the Tested Dose has No Significant Effect Against Hyperglycemia in Lepr$^{db/db}$ Mice after Chronic Treatments.

The in vitro studies showed that Compound #43, but not Compound #68, robustly inhibits glucose production in HepG2 cells (FIG. 1). The studies above show that Compound #43 can lower glucose output and HbA1c levels in Lepr$^{db/db}$ mice (FIG. 3). To further confirm the anti-diabetic effects of Compound #43 in Lepr$^{db/db}$ mice, and to investigate whether the selenium molecule in Compound #43 is required for this anti-hyperglycemia effect, 38-day-old male Lepr$^{db/db}$ mice were administered treatments daily by intraperitoneal injection of equal amount of selenium or sulfur in compound #43 and its direct sulfur-containing analog, Compound #68, for 3 months.

Figure 4:
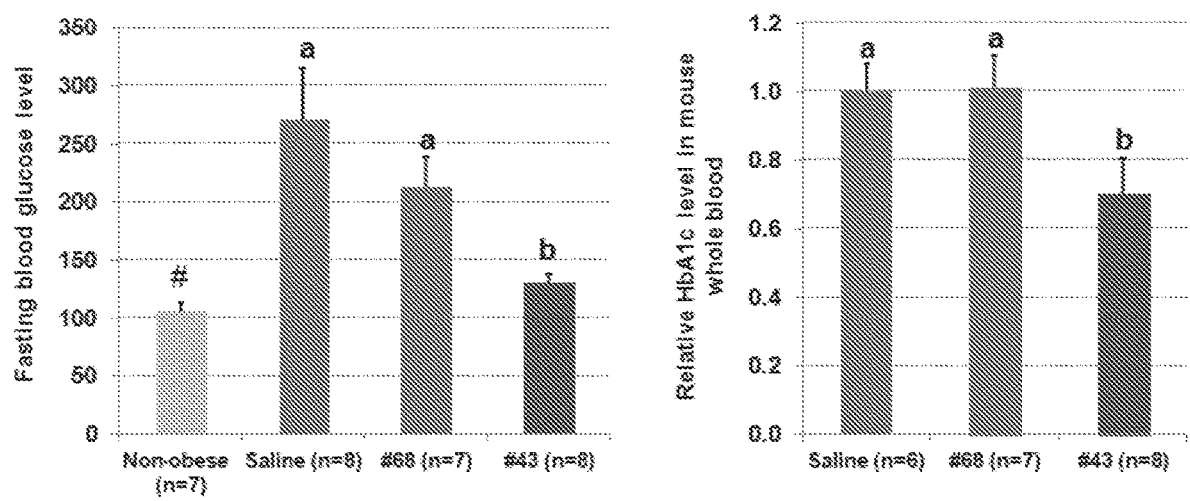
FIG. 4. Effects of Compound #43 and its sulfur analog #68 on blood glucose levels and HbA1c levels in $Lepr^{db/db}$ mice after chronic treatment. $Lepr^{db/db}$ mice were intraperitoneally injected with saline (containing 0.2% the compound solvent DMSO), Compound #43, and #68 at a dose of 25 μg selenium or sulfur as Compound #43 (0.136 mg) or Compound #68 (0.298 mg), respectively, per kilogram body weight daily starting at 38 days of age. At the mouse age of day 128, blood glucose and HbA1c levels of overnight-fasting mice were determined. HbA1c levels in Compound #43 and #68-treated mice were divided by the average HbA1c levels in saline-treated mice to obtain the relative HbA1c levels. Data are presented as mean±SEM of the indicated number of animals. Fasting blood glucose levels in non-diabetic/obese mice (indicated by the symbol # in the bar graph) were obtained from 4-month-old wild-type C57 male mice in the laboratory. Different letters in the bar graph indicate a P value less than 0.05.

Once again, there were no visible morphological, walking behavior abnormalities or body weight changes in Lepr$^{db/db}$ mice after treatment with compounds for the 3-month period, indicating that Compound #43 or #68 at the tested dose had no overt toxic effects on these mice. However, injection of Compound #43 for a period of 3 months resulted in a statistically significant decrease in fasting blood glucose levels, while Compound #68 did not significantly lower blood glucose levels (FIG. 4, left panel). More dramatically, the fasting glucose levels after Compound #43 treatments for 3 months were decreased to about 135 mg/dL, which approaches blood glucose levels reported for normal non-diabetic/obese mice (about 100 mg/dL). In agreement with these reduced blood glucose levels, HbA1c levels in the blood samples from Lepr$^{db/db}$ mice after Compound #43 treatment for 3 months were also significantly decreased (by about 30%), compared to the control (saline-treated) group. However, Compound #68 treatments did not affect blood HbA1c levels in Lepr$^{db/db}$ mice. The extent of decreased HbA1c levels in Lepr$^{db/db}$ mice after this 90-day-treatment with Compound #43 (FIG. 4) appears to be more pronounced than in Lepr$^{db/db}$ mice following 42 days of Compound #43 treatment (FIG. 3).

Together, these in vivo results further validate the finding that Compound #43 can significantly lower blood glucose and HbA1c levels in a mouse model of aggressive Type II diabetes, indicating the potential of Compound #43 in the treatment of hyperglycemia in diabetic patients. In addition, the results also confirmed that the anti-diabetic potential of Compound #43 is lost after the replacement of the selenium atom in Compound #43 with a sulfur atom.

3. Compound #43 Exhibited Higher Anti-Hyperglycemia Potential in Lepr$^{db/db}$ Mice after Chronic Treatments than Compounds #69 and #70

The in vitro studies showed that the replacement of diacetyl groups at 2',3'positions of Compound #43 with dipropanoyl groups (Compound #69) or butanoyl groups (Compound #70) attenuate the activity of Compound #43 in the inhibition of glucose production in HepG2 cells (FIG. 2). The studies above show that Compound #43 can significantly lower glucose output and HbA1c levels in Lepr$^{db/db}$ mice (FIG. 3-4). To further confirm the anti-diabetic effects of Compound #43 in Lepr$^{db/db}$ mice, and to investigate the contribution of the diacetyl groups in Compound #43 for this anti-hyperglycemia effect, 41-day-old male Lepr$^{db/db}$ mice were administered daily treatments, by intraperitoneal injection, of equal amount in selenium of Compounds #43, #69 and #70 for 43 and 90 days.

Figure 5:
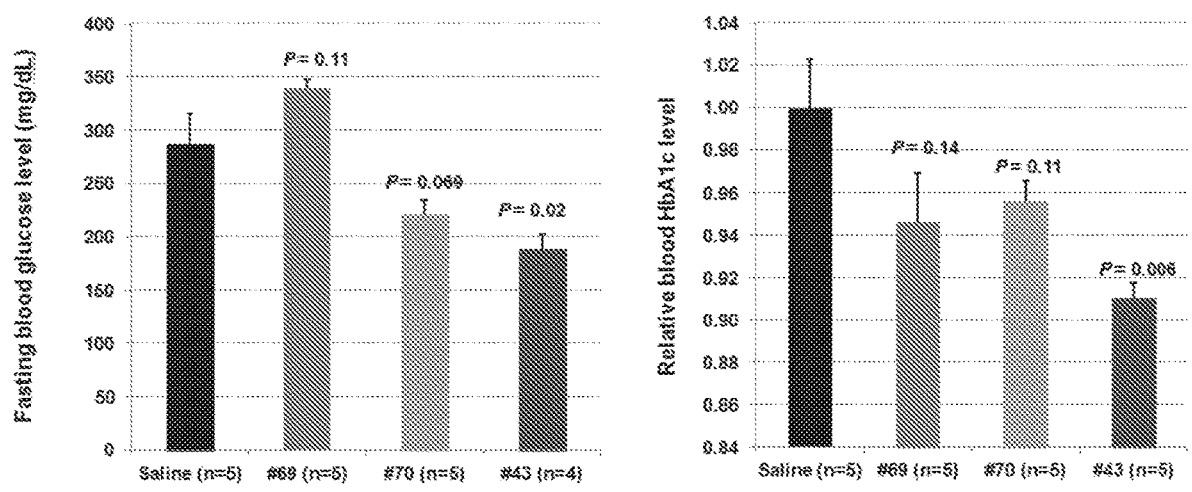
FIG. 5. Differential effects of Compound #43, #69 and #70 on fasting blood glucose and HbA1c levels in $Lepr^{db/db}$ mice after chronic treatment. Male 41-day-old $Lepr^{db/db}$ mice were intraperitoneally injected with saline (containing 0.2% the compound solvent DMSO), Compound #43 (0.136 mg), #69 (0.145 mg) and #70 (0.153 mg) at the dose of 25 μg selenium of each compound per kilogram body weight daily for 43 days (for blood glucose assay) and 90 days (for HbA1c assay), fasted overnight, and then subjected to blood glucose analysis (using a glucometer) or blood HbA1c assay. Data are presented as mean±SEM of indicated number of animals. P values were derived by comparing treatments to the control/saline group.

Once again, there were no visible morphological, walking behavior abnormalities or body weight changes in Lepr$^{db/db}$ mice after treatment with these three compounds for the 90 days, indicating that Compound #43, #69 or #70, at the tested dose, had no overt toxic effects on these mice. It was found that injection of Compound #43 for 43 days resulted in a statistically significant decrease in fasting blood glucose levels (about a 35% decrease from about 290 mg/dL in the saline group to 188 mg/dL) (FIG. 5 left-hand panel). Replacement of the diacetyl groups in Compound #43 with dibutanoyl groups (Compound #70) also resulted in a decrease of fasting blood glucose levels in Lepr$^{db/db}$ mice but less significant than Compound #43 (FIG. 5 left-hand panel). Replacement of diacetyl groups in Compound #43 with dipropanoyl groups (Compound #69) resulted in a slight increase in fasting blood glucose levels in Lepr$^{db/db}$ mice (FIG. 5 left-hand panel). To further validate the above observations, these Lepr$^{db/db}$ mice were continued to be administered daily treatments, by intraperitoneal injection, of equal amount in selenium of Compounds #43, #69 and #70 for another 47 days (a total of 90 days of daily compound treatment), and sera were collected and subjected to blood HbA1c assays. As shown in the right-hand panel of FIG. 5, Compound #43 treatment resulted in a significant decrease of HbA1c levels (FIG. 5, right-hand panel). Initial assessments indicated that Compound #70 treatments also resulted in about 50% decrease of HbA1c levels (FIG. 5, right-hand panel), whereas Compound #69 treatments did not result in a significant decrease of HbA1c levels (FIG. 5, right-hand panel); further review of these data established that neither Compound #69 nor Compound #70 had any significant effect (FIG. 5, right-hand panel). Together, these results suggest that Compound #43 has a great potential for the treatment of hyperglycemia in insulin-resistant subjects. In addition, the results demonstrate that diacetyl groups at the 2',3' position in Compound #43 contribute to its anti-hyperglycemia function in vivo and that extending the diacetyl groups by one or two carbon atoms might, in certain circumstances, have a negative effect on glucose homeostasis.

4. Acute Treatment of Compound #43 Resulted in a Dose-Dependent Decrease of Blood Glucose Levels in Lepr$^{db/db}$ Mice The above studies demonstrated that chronic treatment with Compound #43 can significantly lower blood glucose and HbA1c levels. To determine an effective dose range and establish the duration of response to Compound #43, 8-10-week-old Lepr$^{db/db}$ male mice were fasted overnight and then injected intraperitoneally with saline (containing 0.2% DMSO, the maximal injected volume of Compound #43 stock solvent), 0.0054, 0.054, 0.54 and 5.4 mg Compound #43 (made by diluting the stock compound with saline)/kg body weight. Blood glucose levels in Lepr$^{db/db}$ mice, immediately before and after the injection at 1, 2, 3, 5 and 8 hours (under fasting conditions but having free access to water), were examined and the resulting blood glucose levels were plotted for each individual animal at each time point.

Figure 6:
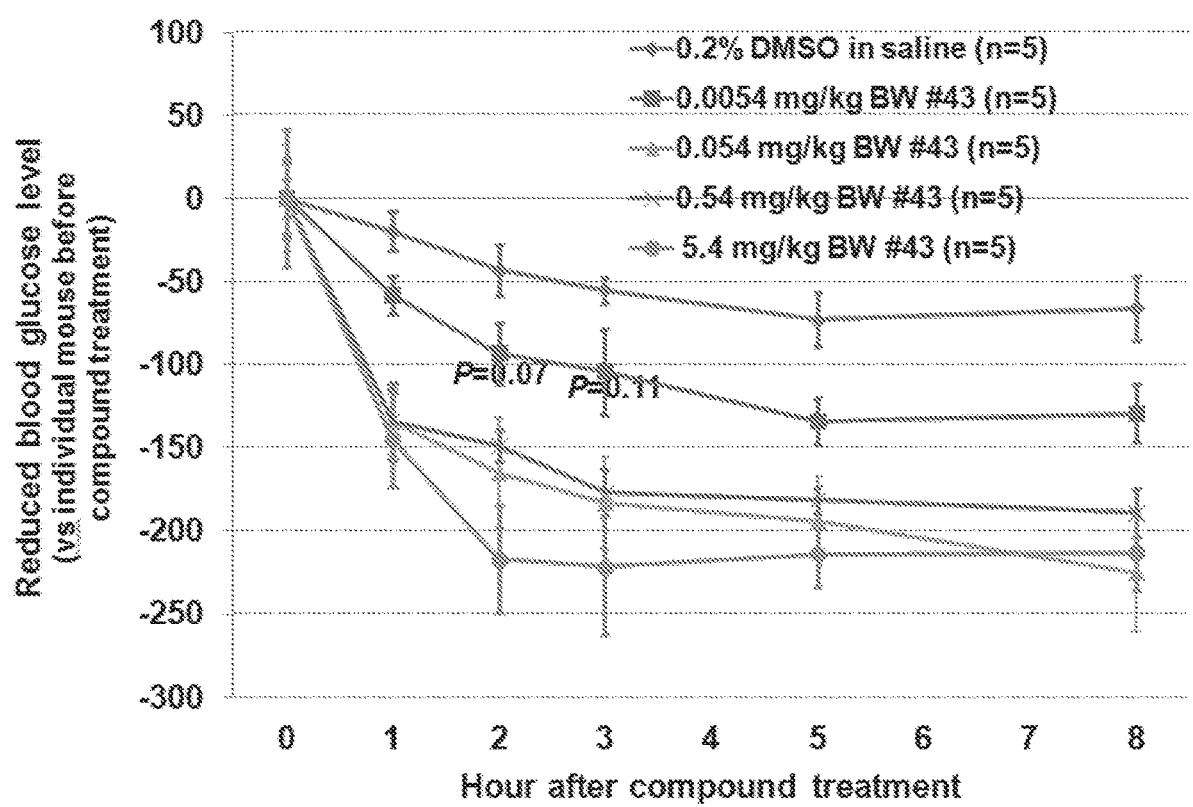
FIG. 6. Acute treatment of Compound #43 resulted in a decrease in blood glucose level in $Lepr^{db/db}$ male mice. 8-10-week-old $Lepr^{db/db}$ male mice were fasted overnight, and then injected intraperitoneally with saline (containing 0.2% DMSO, the maximal injected volume of Compound #43 stock solvent), 0.0054, 0.054, 0.54 and 5.4 mg Compound #43/kg body weight. Blood glucose levels in $Lepr^{db/db}$ mice right before and after injection at 1, 2, 3, 5 and 8 hours (under fasting conditions but having free access to water) were examined. The reduced glucose levels in individual mice were obtained by subtracting the glucose level right before the injection from the blood glucose level at each time period after injection. Data are presented as mean±SEM of the indicated number of animals. With the exception of the P values shown, which relate to the early time points of the 0.0054 mg/kg BW treatment, all other reductions were significant (P<0.05) when compared with the corresponding time points for DMSO/saline injection.

Acute single injection of the above doses of Compound #43 did not cause any visible toxic effects on gross morphological and walking behavior. In saline-treated Lepr$^{db/db}$ mice, there was only a slight decrease (about 50-70 mg/dL) in blood glucose levels during the 8 hr time period of the test (FIG. 6), which is consistent with the fact that these Lepr$^{db/db}$ mice display defective glucose clearance ability. However, treatment with Compound #43 at all tested doses resulted in a significant decrease of blood glucose levels (when compared to its saline group at each time period) except the lowest dose of Compound #43 treatment at 2 or 3 hr post-injection (in which the decreased glucose levels were close to being statistically significant) (FIG. 6). The results showed that Compound #43 at all tested doses was effective in reducing blood glucose levels at 1 hr after the single injection. This indicates that Compound #43 can reach the relevant target tissues in vivo within a short time period (i.e., 1 hr) to elicit its glucose-lowering effect. The activity of Compound #43 in reducing blood glucose levels under fasting conditions peaked at 2 to 5 hr post-administration, and this effect was maintained for at least another 3 hr. Since the tested animals (which had been fasted overnight and continued to be fasted for the tested 8 hr time period) were unable to be further fasted, the maximal effective duration of Compound #43 action was not determined from these experiments.

The results demonstrate that acute treatment with Compound #43 over a 1000-fold concentration range significantly reduces blood glucose levels in a widely used animal model of insulin resistance and type 2 diabetes. Compound #43 is fast-acting (≤1 hr post-treatment) and remains active for at least 8 hours.

5. Acute Treatment of Compound #43 Attenuates Progression to Hyperglycemia in Younger $Lepr^{db/db}$ Mice As discussed above, $Lepr^{db/db}$ mice display elevated plasma insulin beginning at 10 to 14 days-of-age and hyperglycemia (i.e., high blood sugar levels) at approximately 4-8 weeks of age (Coleman D L. 1978 Diabetologia 14:141-8). To test whether Compound #43 has the potential to attenuate the development of hyperglycemia, a single dose of Compound #43 was administered via an acute injection in younger mice. In brief, 6-week-old $Lepr^{db/db}$ male mice under normal feeding conditions were intraperitoneally injected once with saline containing 0.2% DMSO or Compound #43 at a dose of 5.4 mg/kg body weight. 24 hr after the treatment, blood glucose levels were determined on these mice while they had ad-libitum access to food and water.

Figure 7:
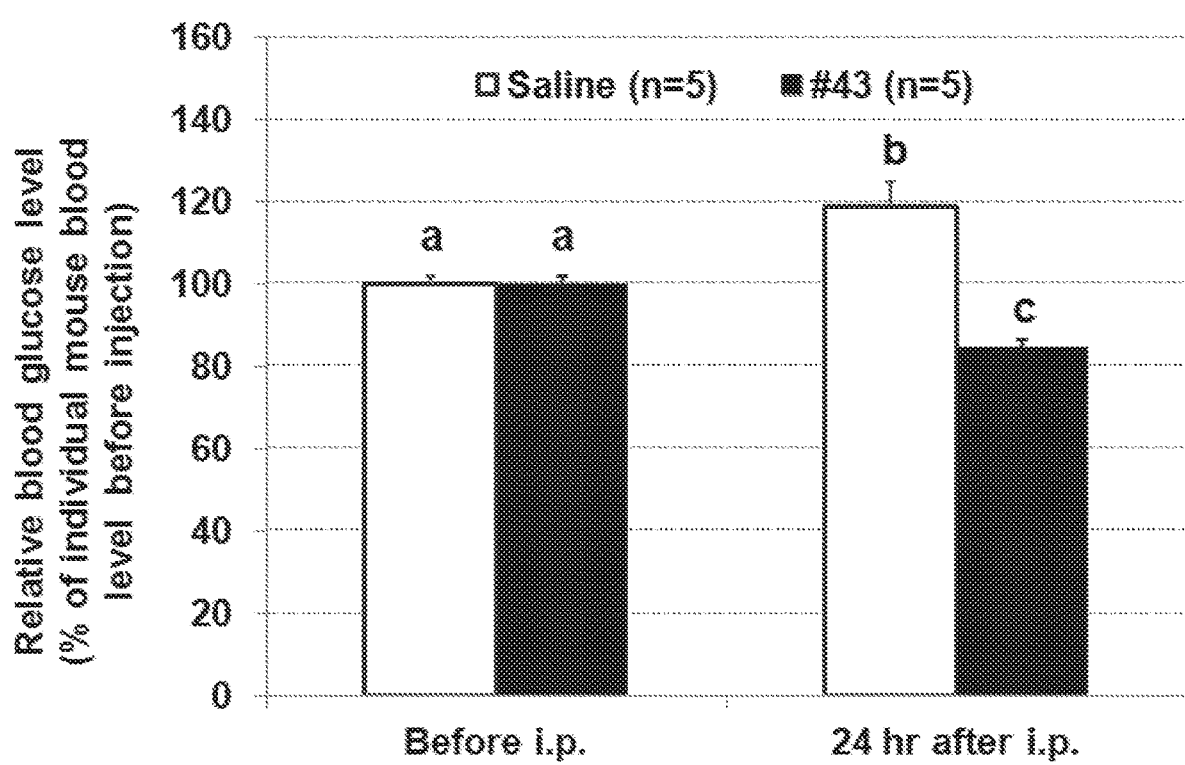
FIG. 7. Acute treatment of Compound #43 reduced the blood glucose levels in $Lepr^{db/db}$ male mice under ad-libitum feeding conditions. Blood glucose levels of 6-week-old $Lepr^{db/db\ male}$ mice with free access to food and water were determined before and at 24 hr after an intraperitoneal injection of saline (containing 0.2% the compound solvent DMSO) or Compound #43 at a dose of 5.4 mg/kg body weight. The relative blood glucose levels before i. p. injection was normalized by the average glucose level of all five mice within the group, and referred to as 100%. After 24 hr injection, the relative blood glucose level in each mouse was normalized by its glucose level before injection. Different letters represents a statistically significant difference (P<0.05) between groups.

As shown in FIG. 7, blood glucose levels in these young $Lepr^{db/db}$ mice at 24 hr after saline treatment were significantly increased (about 20% increase), indicating that these mice are still in the process of developing hyperglycemia. In contrast, treatment of Compound #43 resulted in a significant decrease (about 20%) of blood glucose levels in $Lepr^{db/db}$ mice (FIG. 7).

These results suggest that Compound #43 has the potential to attenuate the development of hyperglycemia. In addition, these studies also indicate that the effectiveness of Compound #43 in lowering glucose output likely will last at least 24 hr in these diabetic mice under feeding conditions.

6. Enhanced Glucose Tolerance in Diabetic $Lepr^{db/db}$ Mice after Administration of Compound #43

The glucose tolerance test identifies abnormalities in the way the body handles glucose after a high and rapid rise of blood sugar (e.g., usually after a meal). Insulin plays a critical role not only in the inhibition of glucose production in the liver, but also in glucose uptake, storage and metabolism in muscle, liver, and fat cells, causing lower glucose levels in the bloodstream.

Diabetic patients have a very low glucose tolerance either due to their inability to produce insulin or to respond to insulin efficiently to maintain glucose homeostasis. The in vitro studies described herein indicate that Compound #43 not only can mimic insulin but also can bypass insulin to inhibit glucose production (FIG. 1-2). $Lepr^{db/db}$ mice are the ideal mouse Type II diabetic model to investigate the role of Compound #43 in maintaining glucose homeostasis, considering the fact that impaired glucose tolerance and insulin-resistance are displayed in these mutant mice. Therefore, the effect of Compound #43 and other structurally similar related selenium and sulfur compounds on improved glucose tolerance in $Lepr^{db/db}$ mice after intraperitoneal injection of the respective compounds into mice was investigated.

These male mice, at the age of 38 days, were injected intraperitoneally with physiological saline (containing 0.2% DMSO), Compound #C, #43, or #50 (25 µg selenium of each compound per kilogram body weight) for 43 days. At the end of treatment, these mice were fasted overnight, injected with glucose (2 g/kg body weight) and blood glucose levels were measured at 0.25 hours (15 minutes), 0.5 hours (30 minutes), 1 hour (60 minutes) and 2 hours (120 minutes) post-glucose injection. The blood glucose levels immediately before the glucose injection (referred to as the zero time point) were also recorded.

Figure 8:
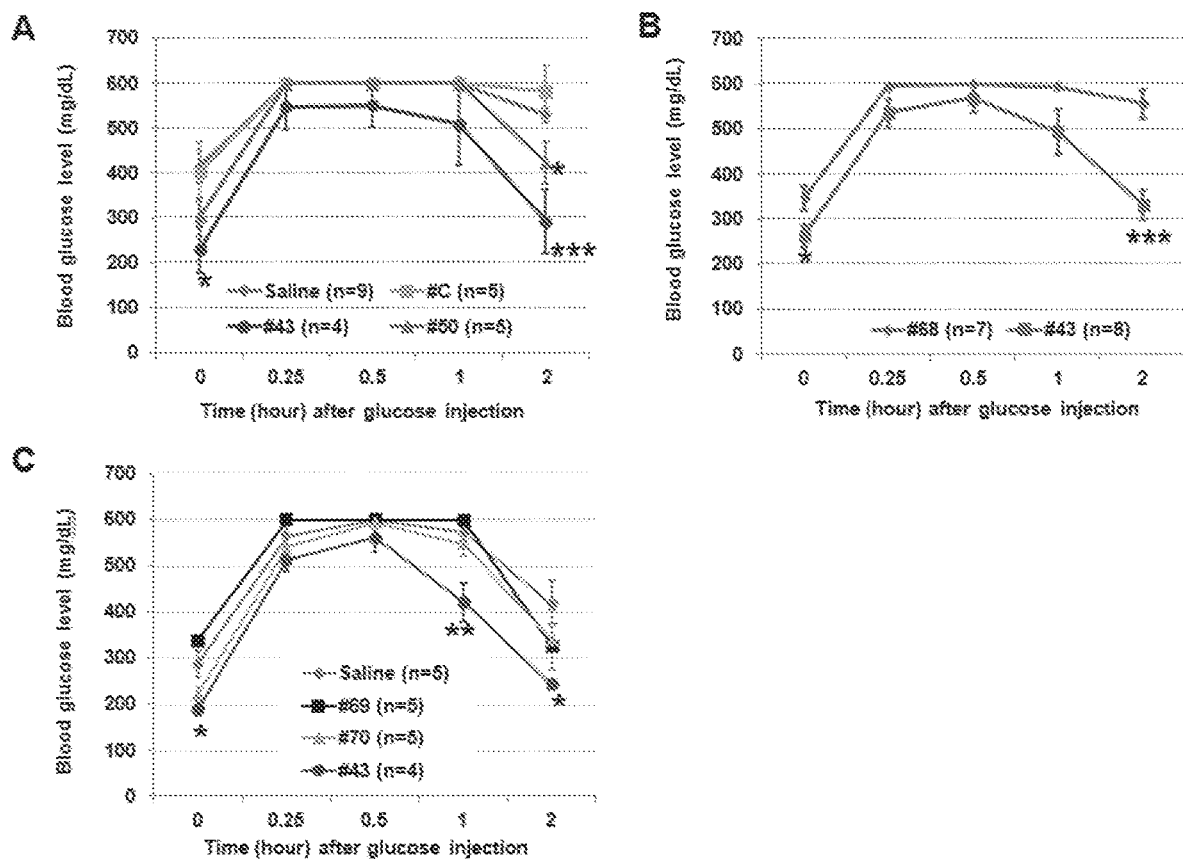
FIG. 8. Chronic treatment of Compound #43 improves glucose tolerance in $Lepr^{db/db}$ mice. A-B. Male 38-day-old $Lepr^{db/db}$ mice were intraperitoneally injected with (A) saline (containing 0.2% the compound solvent DMSO), Compound #43, Compound #C and Compound #50 daily for 43 days, or with (B) Compound #68 or Compound #43 for 60 days. C. Male 41-day-old $Lepr^{db/db}$ mice were intraperitoneally injected with saline (containing 0.2% the compound solvent DMSO), Compound #43, Compound #69 and Compound #70 daily for 43 days. The daily injected dose of all listed compounds was 25 μg selenium or sulfur per tested compound per kilogram body weight. At the end of treatment, these mice were fasted overnight, injected with glucose (2 g/kg body weight) and blood glucose levels immediately before glucose injection (referred to as zero time point) and at 0.25 hours, 0.5 hours, 1 hour and 2 hours post-glucose injection were measured using a glucometer with the maximal reading of 600 mg/dL. A glucose level in excess of this limit was recorded as 600 mg/dL. Data are presented as Mean±SEM of indicated number of animals. * P<0.05,  P<0.01, * P<0.001 when compared to (A, C) saline-treated or (B) Compound #68-treated mice at the same time point.

As shown in FIG. 8A, a significant increase in blood glucose levels beginning at 0.25 hours and at all the following tested time points was observed in saline-treated $Lepr^{db/db}$ mice after injection of glucose. As described herein, the glucose measurement limit of the glucometer employed for these analyses was 600 mg/dL. Thus, glucose levels in excess of this limit were recorded as 600 mg/dL. Accordingly, certain measurements at the tested time point after glucose injection, particularly for the saline-treated animals, may well represent underestimations of the true blood glucose concentrations.

In Compound #C-treated mice, blood glucose levels at all tested time points after glucose injection remained very high, similar to the saline-treated group (FIG. 8A). These results suggest that Compound #C at the tested dose did not improve glucose tolerance in these insulin-resistant diabetic mice.

Compound #50 treatment resulted in a significant decrease of glucose level at the 2 hr time point after glucose injection when compared to saline-treated group, even though there was no obvious decrease at 0.25, 0.5 or 1 hr after glucose injection in FIG. 8A. These results suggest that Compound #50 likely has some effect in improving glucose tolerance in these diabetic mice.

In Compound #43-treated $Lepr^{db/db}$ mice, in contrast, blood glucose levels at 0.25, 0.5 and 1 hr after glucose injection were visibly lower than saline-, Compound #C- or #50-treated mice (FIG. 8A). Due to the measurement limit of the glucometer, the extent of the decrease of glucose levels in Compound #43-treated mice relative to the other treatments at these time points after glucose injection was likely much more dramatic than that shown in FIG. 8A. At 2 hours after glucose injection, blood glucose levels in Compound #43-treated $Lepr^{db/db}$ mice were much lower than saline-, Compound #C- or Compound #50-treated littermates (see FIG. 8A), and were almost completely back to pre-injection glucose levels. The decrease of glucose levels in Compound #43-treated $Lepr^{db/db}$ mice at 2 hours after glucose injection was significantly different when compared to Saline- or Compound #C-treated mice ($P<0.001$). These results suggest that Compound #43, but not Compound #C, at the tested dose can almost completely restore insulin action in these insulin-resistant diabetic mice as assessed by improved glucose tolerance, while Compound #50 may also have some beneficial effects in the improvement of glucose clearance.

To further confirm the great potential of Compound #43 to improve glucose clearance in $Lepr^{db/db}$ mice and to investigate whether the selenium atom in Compound #43 is required for this effect, 38-day-old male $Lepr^{db/db}$ mice were administered treatments daily by intraperitoneal injection of an equal amount of selenium or sulfur in Compound #43 or #68, respectively, for 2 months. At the end of treatment, these mice were fasted overnight and subjected to a glucose tolerance test as described above.

As shown in FIG. 8B, a significant increase in blood glucose levels was observed in Compound #68-treated Lepr$^{db/db}$ mice after injection of glucose beginning at 0.25 hours and at all the following tested time points. There was no obvious decrease of blood glucose levels at the 2 hr time point after glucose injection (when compared to levels at 0.25, 0.5 and 1 hr time periods), indicating that Compound #68 at the tested dose has little or no effects to improve glucose tolerance in these insulin-resistant diabetic mice.

In Compound #43-treated Lepr$^{db/db}$ mice, blood glucose levels before the glucose challenge injection were significantly lower than Compound #68-treated mice (P<0.05). These results were consistent with the above observation that Compound #43 is more potent than Compound #68 in reducing fasting blood glucose levels in this diabetic mouse model (FIG. 4). Blood glucose levels in Compound #43-treated Lepr$^{db/db}$ mice at 0.25, 0.5 and 1 hr after glucose injection were lower than Compound #68-treated mice. At 2 hours after glucose injection, blood glucose levels in Compound #43-treated Lepr$^{db/db}$ mice were significantly lower than Compound #68-treated littermates (see FIG. 8B, P<0.001). The glucose clearance curve of Compound #43-treated Lepr$^{db/db}$ mice in this experiment (FIG. 8B) was almost identical to the curve observed in the first glucose tolerance test described above (FIG. 8A). Once again, due to the measurement limit of the glucometer, the decrease of glucose levels in Compound #43-treated mice relative to Compound #68-treated mice at these time points after glucose injection was likely much more dramatic than that shown in FIG. 8B. Regardless, the above results further confirm that Compound #43 at the tested doses dramatically improves glucose tolerance, and the replacement of the selenium atom in Compound #43 with sulfur almost completely destroys its ability to facilitate glucose clearance in these insulin-resistant diabetic Lepr$^{db/db}$ mice.

Finally, it was investigated whether the replacement of the acetyl groups at both 2' and 3' positions of the ribose group of Compound #43 with propanoyl or butanoyl groups could improve glucose clearance in Lepr$^{db/db}$ mice. Male 41-day-old male Lepr$^{db/db}$ mice were administered treatments daily by intraperitoneal injection of an equal amount of selenium in Compound #43, #69 or #70, respectively, for 43 days. At the end of treatment, these mice were fasted overnight and subjected to a glucose tolerance test as described above.

As shown in FIG. 8C, a significant increase in blood glucose levels beginning at 0.25 hours and at all the following tested time points was observed in saline-treated Lepr$^{db/db}$ mice after injection of glucose. There was no obvious decrease of blood glucose levels before the 1 hr time point after glucose injection (when compared to glucose levels at 0.25 and 0.5 hr time periods), while glucose levels were slightly decreased at 2 hr after glucose injection in these insulin-resistant diabetic mice.

Compound #69 treatment resulted in a slight but non-significant decrease in glucose levels at the 2 hr time point after glucose injection, when compared to the saline-treated group, even though there was no obvious decrease of blood glucose levels at 0.25, 0.5 or 1 hr after glucose injection in FIG. 8C. These results suggest that Compound #69 may has some effect in improving glucose tolerance in these diabetic mice.

In Compound #70-treated mice, fasting blood glucose levels before glucose injection were lower than the saline-treated group (FIG. 8C). After glucose injection, especially at 2 hr time point, there was a slight but non-significant decrease in blood glucose levels in Compound #70-treated mice when compared to saline-treated mice. These results suggest that Compound #70, at the tested dose, like Compound #69, also likely has some effect in improving glucose tolerance in these insulin-resistant diabetic mice.

In contrast, blood glucose levels at 0.25 and 0.5 hr after glucose injection in Compound #43-treated Lepr$^{db/db}$ mice were visibly lower than saline-, Compound #69- or #70-treated mice (FIG. 8C). At 1 hour after glucose injection, blood glucose levels in Compound #43-treated Lepr$^{db/db}$ mice were significantly lower than saline-, Compound #69- or Compound #70-treated littermates (FIG. 8C). At 2 hours after glucose injection, blood glucose levels in Compound #43-treated Lepr$^{db/db}$ mice were also much lower than Saline-, Compound #69- or Compound #70-treated mice. The decrease in glucose levels in Compound #43-treated Lepr$^{db/db}$ mice at 2 hours after glucose injection was significantly different when compared to saline-treated mice (P<0.05). Once again, due to the measurement limit of the glucometer, the extent of the decrease of glucose levels in Compound #43-treated mice relative to the other treatments at each time point after glucose injection was likely much more dramatic than that shown in FIG. 8C. Regardless, the results further demonstrate that Compound #43 at the tested dose can dramatically improve glucose tolerance in these insulin-resistant diabetic mice. Also these results suggest that Compound #69 and #70 may have some beneficial effects in the improvement of glucose clearance. In comparing the chemical structures of Compound #43 with Compound #69 and #70, it is evident that the acetyl groups at both 2' and 3' positions of the ribose group of Compound #43 are essential for optimum glucose clearance activity, and that replacement of these diacetyl groups in Compound #43 with dipropanoyl or dibutanoyl groups significantly attenuate its ability to facilitate glucose clearance in these insulin-resistant diabetic Lepr$^{db/db}$ mice.

In summary, the above studies demonstrate that Compound #43 at the tested dose can significantly improve glucose tolerance in Lepr$^{db/db}$ mice. The action of Compound #43 in this process is likely mediated through the improvement of insulin sensitivity in the clearance of glucose in the skeletal muscle, liver and the adipose tissues. Furthermore, while selenium is essential for the action of Compound #43 its presence is not sufficient on its own to confer glucose clearance ability on a diabetic subject. The selenium atom must be presented in a very specific chemical form. This is evidenced by the lower activity of Compound #50 and the lack of activity of Compound C; both of which are structurally very similar to Compound #43. In addition, the acetyl groups at both 2' and 3' positions of the ribose group of Compound #43 are also required for maintaining its activity in glucose clearance.

Example 4: Inhibition of the Expression of the Gluconeogenic Enzyme Gene G6pc in the Liver of Diabetic Leptin Receptor (Lepr) Spontaneous Null Mutant Mice and in Cultured Liver Cells after Compound #43 Treatment, Together with the Potentiation of Insulin Action in the Inhibition of G6pc Expression in Cultured Liver Cells Liver is the main organ for producing glucose to maintain normal glucose levels in the blood stream. Glucose-6-Phosphatase Catalytic subunit (G6pc) is an essential enzyme for gluconeogenesis in the liver. The effect of Compound #43 on the regulation of G6pc expression was studied both in vivo and in vitro.

Materials and Methods
Compounds

Compound #43, #C, #D, #E, and #50 were synthesized in the Chemistry Laboratory of Alltech, Inc. The purities of all tested compounds were verified to be ≥99%, as determined by HPLC.

In Vivo Treatment with Compound #43, and #50 in $Lepr^{db/db}$ Mice

Male $Lepr^{db/db}$ mice (C57BL/6J strain, purchased from The Jackson Laboratory) at 38-days of age were intraperitoneally injected daily with physiological saline (0.09% NaCl) containing 0.2% DMSO, Compound #50, or Compound #43 (25 µg selenium equivalent of each compound per kilogram body weight, diluted in the sterile physiological saline) for 52 days. After the treatment, livers were collected and subjected RNA analysis.

Cell Lines and Cell Amplification

Human hepatoma HepG2 and mouse liver AML-12 cells were purchased from the American Type Culture Collection (ATCC, Manassas, Va.). HepG2 cells were amplified in Eagle's Minimum Essential Medium (EMEM) supplemented with 10% FBS. AML-12 cells were amplified in Dulbecco's modified Eagle's medium and Ham's F12 (DMEM/F12) media supplemented with 10% fetal bovine serum (FBS), 40 ng/ml dexamethasone (Dex, Sigma) and 1×ITS (containing 0.01 mg/ml bovine insulin, 0.0055 mg/ml human transferrin, 5 ng/ml sodium selenite) solution (Sigma).

Cell Treatments for RNA Analysis

For RNA analysis of basal G6pc expression (without the presence of diabetic stimuli: 8-CPT/Dex), amplified AML-12 and HepG2 cells were cultured on 24-well plates (0.5-2×$10^5$ cells/well) overnight in 10% FBS ITS- and Dex-free DMEM/F12 media and 10% FBS EMEM media, respectively. These cells were rinsed twice with PBS to remove residual sera. Then, the PBS-washed HepG2 cells were treated without or with insulin or Compound #43 in serum-free EMEM media for 40 hr. In some experiments, the PBS-washed AML-12 cells were incubated without or with Compound #43 or other selenium compounds in serum-free DMEM/F12 media for 24 hours. In other experiments, amplified AML-12 cells were pretreated without or with Compound #43 (150 or 300 ppb) in 10% FBS but ITS/Dex-free DMEM/F12 media for 24 hr. After 24 hr treatment, AML-12 cells were washed twice with PBS (to remove any residual serum in the culture) and then treated with insulin, Compound #43 or both, in the serum-free DMEM/Dex media for 6 hr.

For RNA analysis of the diabetic stimuli-induced G6pc expression, the AML-12 cells were pretreated without or with Compound #43 (150 or 300 ppb) in 10% FBS but ITS/Dex-free DMEM/F12 media for 24 hr. Then these cells were washed twice with PBS remove any residual sera, and incubated with Compound #43 (150 or 300 ppb) in the presence or absence of insulin (10 or 100 nM), or 0.1 mM 8-CPT (Sigma) and 0.5 µM Dex in serum-free plain DMEM/F12 media for another 6 hours.

RNA Isolation and Real-Time PCR Analysis

Total RNA from saline- or selenium compound-treated $Lepr^{db/db}$ mice was isolated using a Qiagen RNAeasy RNA isolation kit according to the Manufacturer's protocol. Total RNA from cultured cells was isolated using Trizol (Invitrogen) according to the manufacturer's protocol, and then incubated with DNase I to remove any potential contaminating genomic DNA. RNA samples were subjected to real-time PCR (QRT-PCR) analysis using Applied-Bioscience's RT kit and predesigned Taqman probes (Invitrogen), as described previously (Lan et al EMBO J 2003). Data were normalized by Actin B (Actb) mRNA levels in each sample, and are presented as mean±SEM of 3-5 samples.

Statistical Analysis

Where applicable, a Student's t-test was used to determine the statistical significance of differences between treatment groups with a P value less than 0.05 deemed to be statistically significant.

Results:

1. Analysis of G6pc mRNA Expression in the Livers of $Lepr^{db/db}$ Mice

Previous experiments showed different effects of Compound #43 and #50 in the inhibition of blood glucose levels and HbA1c levels in $Lepr^{db/db}$ mice (FIG. 3). Without wishing to be bound to any particular hypothesis, such different effects might be due, at least in part, to potential differential action of these compounds on expression of the gluconeogenic G6pc gene in vivo. Therefore, the G6pc mRNA expression in $Lepr^{db/db}$ mice was measured after chronic treatment of these two compounds.

Figure 9:
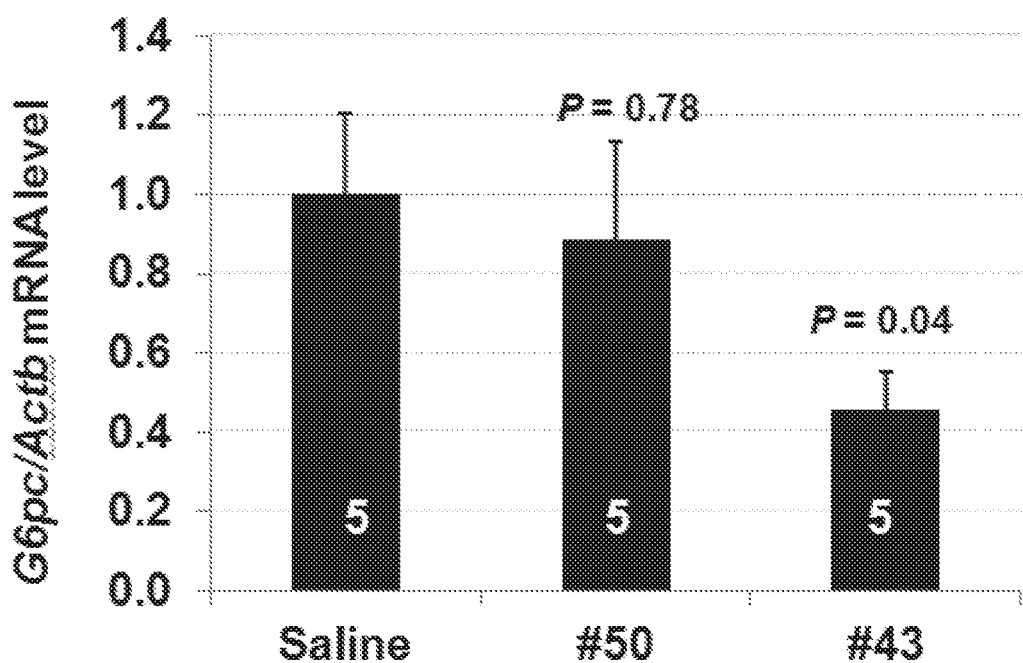
FIG. 9. Attenuated G6pc mRNA in the livers of $Lepr^{db/db}$ mice after chronic treatment with Compound #43. $Lepr^{db/db}$ mice at postnatal day 38 were intraperitoneally injected with saline (containing 0.2% the compound solvent DMSO), Compound #50 and #43 at the dose of 25 μg selenium of each compound per kilogram body weight daily for 52 days. QRT-PCR was performed on liver RNA isolated from these compound-treated mice. G6pc mRNA level in each sample was normalized by Actb mRNA level and data are presented as mean±SEM of five mice per group. P value is relative to the saline group.

As shown in FIG. 9, G6pc mRNA levels in the liver was slightly, but not significantly, decreased in $Lepr^{db/db}$ mice after the treatment of Compound #50. However, treatment of Compound #43 resulted in a dramatic decrease (about 56% reduction) of G6pc mRNA levels in the livers of $Lepr^{db/db}$ mice, when compared to saline-treated controls (FIG. 9).

Together, the results provide in vivo evidence that there may be a differential effect of these selenium compounds in the inhibition of G6pc expression, and that Compound #43 is a potent inhibitor of G6pc expression in the liver of these severe Type II diabetic mice. These results suggest that reduced blood glucose and HbA1c levels in $Lepr^{db/db}$ mice after Compound #43 treatment (FIG. 3) are, at least in part, due to attenuated G6pc mRNA expression. Furthermore, because G6pc expression is modulated in response to insulin signaling and given that $Lepr^{db/db}$ mice are insulin-resistant, the results suggest that Compound #43 can bypass insulin or restore insulin action to regulate G6pc expression in these diabetic mice.

2. Inhibition of G6pc mRNA Expression and Potentiation of Insulin Action in the Inhibition of G6pc Expression in Mouse and Human Liver Cells after Compound #43 Treatment The above studies revealed that Compound #43 can significantly inhibit G6pc expression in diabetic mice under insulin-resistant conditions. Cultured liver cells were used to investigate (a) whether there is differential effect of selenium compounds on G6pc expression, (b) whether Compound #43 has direct effects on the G6pc expression in the liver and (c) whether Compound #43 can improve insulin action in the regulation of G6pc expression. Two treatment regimes (direct compound treatment of liver cells under serum-free condition, and the pretreatment of liver cells with compounds in the serum-containing media followed by retreatment of compounds under the serum-free conditions) were performed to examine the effect of Compound #43 on G6pc expression in these liver cells.

Figure 10:
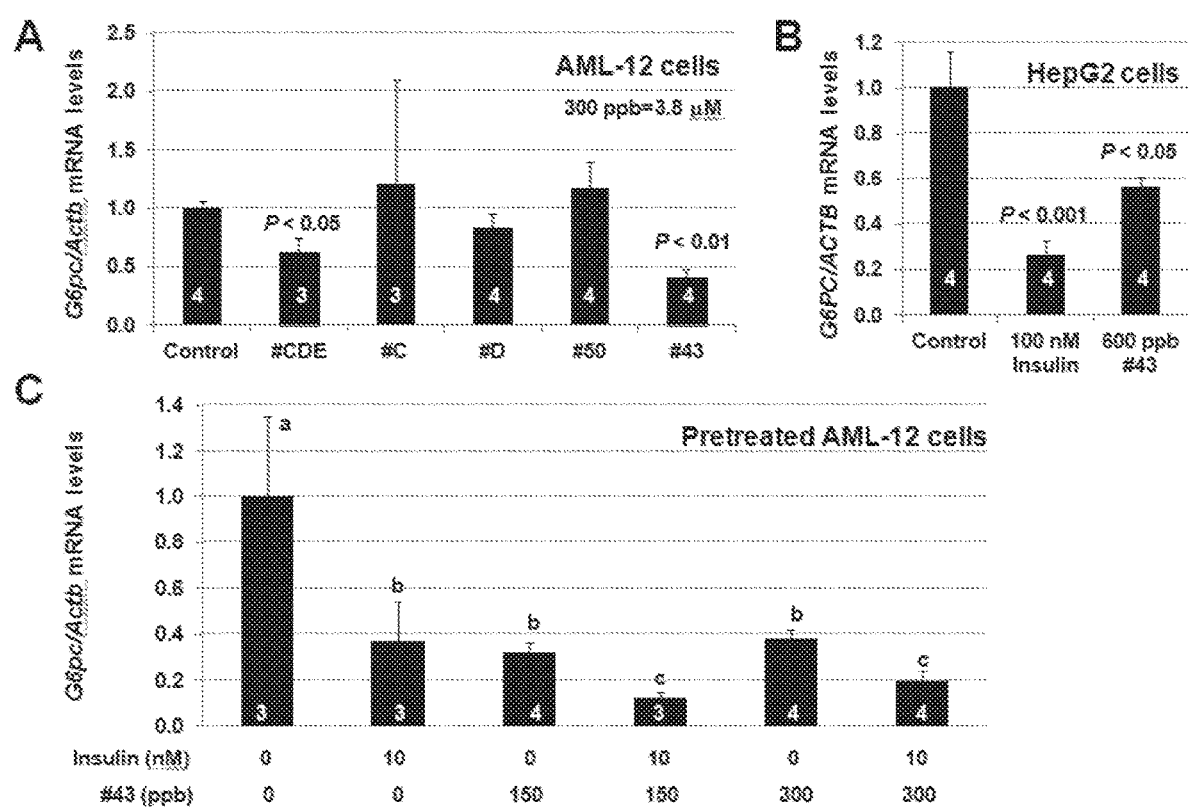
FIG. 10. Inhibition of basal G6pc/G6PC expression by Compound #43 in AML-12 and human HepG2 cells, and the cooperative action of both Compound #43 and insulin in the inhibition of G6pc expression in AML-12 cells. (A) Effects of selenium compounds on G6pc expression in AML-12 cells under serum-free conditions. AML-12 cells were treated without (Control), or with compound CDE combination, Compound #C, Compound #D, Compound #50 and Compound #43 at a dose of 300 parts per billion (ppb) of selenium (equivalent to 3.8 uM of each compound) in serum-free, Insulin-Transferrin-Sodium selenite supplement (ITS) and Dexamethasone (Dex)-free media for 24 hr. (B) Inhibition of G6PC expression by Compound #43 in human HepG2 cells. HepG2 cells were incubated with 100 nM of insulin or 600 ppb of Compound #43 in serum-free media for 40 hr. (C) Inhibition of G6pc expression by Compound #43, and the cooperative action of both Compound #43 and insulin in the inhibition of G6pc expression in AML-12 cells that were pretreated with Compound #43. AML-12 cells were pretreated with Compound #43 in FBS-containing but ITS/Dex-free media for 24 hours followed by retreatment of Compound #43 in the presence or absence of 10 nM insulin in serum/ITS/Dex-free media for 6 hours. G6pc mRNA level in each sample was normalized by Actb mRNA level and data are presented as mean±SEM of indicated number of sample in each group. P value in panel A-B was compared to the Control group. Different letters in panel C represents a statistical significance (P<0.05) between those two groups.

First, mouse liver AML-12 cells were treated without (Control), with compound CDE combination, Compound #C, Compound #D, Compound #50 and Compound #43 at a dose of 300 parts per billion (ppb) of selenium (equivalent to 3.8 µM of each compound) in serum-free, Insulin-Transferrin-Sodium selenite supplement (ITS) and Dexamethasone (Dex)-free media for 24 hr to investigate whether there is a differential effect of these selenium compounds on G6pc expression. As shown in FIG. 10A, compound CDE (300 ppb of each compound) resulted in a significant decrease in G6pc mRNA expression. However, Compound #C, #D, or #50 at the tested dose did not significantly inhibit G6pc expression in AML-12 cells. In contrast, treatment with Compound #43 at the same dose of selenium resulted in a robust decrease (about a 60% decrease, when compared to the Control group) of G6pc expression in AML-12 cells (FIG. 10A). The extent of decreased G6pc expression (60%) after Compound #43 treatment was more pronounced than with the Compound CDE combination treatment (about a 40% decrease). These results suggest that there may be a differential effect of these seleno-organic compounds on the inhibition of G6pc expression in vitro and Compound #43 is the most potent compound among all tested compounds in the process. This is consistent with the above in vivo mouse studies (FIG. 9). Since this experiment was performed in AML-12 cells under totally serum-free conditions, (i.e. the absence of insulin or any other growth factors) the results suggest that the Compound #43 can mimic but bypass insulin to directly inhibit G6pc expression in AML-12 cells with a potency higher than the Compound CDE combination.

Next, another liver cell line, human HepG2 cells, was incubated with 100 nM of insulin or 600 ppb of Compound #43 in serum-free media for 40 hr to further validate the direct inhibitory effect of Compound #43 on G6PC expression, As shown in FIG. 10B, insulin treatment resulted in a significant decrease of G6PC expression, indicating that the insulin signaling is functioning in HepG2 cells. Further, G6PC mRNA levels in HepG2 cells, after the treatment of Compound #43 under totally serum-free conditions, were significantly attenuated when compared to the Control group (FIG. 10B). The decreased G6PC expression in HepG2 cells after Compound #43 treatment is consistent with the reduced glucose production observed in FIG. 1. Thus, the results further suggest that Compound #43 can mimic but bypass insulin to directly downregulate G6PC expression and thereby inhibit glucose production in HepG2 cells.

Finally, AML-12 cells were pretreated with Compound #43 in serum-containing but ITS/Dex-free media for 24 hr followed by retreatment of this compound in FBS/ITS/Dex-free media in the presence or absence of insulin for 6 hr to further investigate whether Compound #43 can inhibit G6pc expression and whether there is additive or synergistic effect between insulin and Compound #43 in the downregulation of G6pc expression. As shown in FIG. 10C, treatment of 10 nM of insulin resulted in a significant decrease (about 65%) of G6pc mRNA levels when compared to Control group ($1^{st}$ bar in FIG. 10C). Like insulin, treatment of Compound #43 (at both 150 and 300 ppb) also resulted in a significant decrease of G6pc expression with the decrease levels comparable to 10 nM insulin. Furthermore, the decrease in G6pc mRNA levels was more pronounced in AML-12 after the pretreatment with Compound #43 followed by co-treatment of both Compound #43 and insulin than with treatment using Compound #43 or insulin alone. These results further support the above observations that Compound #43 can mimic but bypass insulin to inhibit G6pc expression in AML-12 cells. The results also suggest that Compound #43 can potentiate insulin action in downregulating G6pc expression in AML-12 cells.

3. Inhibition of G6pc Expression and Improvement of Insulin Action in the Regulation of G6pc Expression after Compound #43 Treatment in AML-12 Cells Cultured Under Simulated Diabetic Conditions (Stimulated by Both 8-CPT and Dex)

Cyclic AMP (8-CPT) and Dex are well known stimuli of G6pc expression and glucose production in the liver, which mimics diabetic conditions in vivo. To further investigate the effects of Compound #43 on G6pc expression, G6pc mRNA expression in AML-12 cells co-treated with cell-permeable 8-(4-chlorophenylthio) cAMP (8-CPT) and Dexamethasone (Dex) were examined. In brief, AML-12 liver cells were pretreated without or with 150 ppb or 300 ppb of Compound #43 in 10% FBS but ITS/Dex-free DMEM/F12 media for 24 hours. After washed with PBS twice, these cells were retreated with these selenium compounds in the presence or absence of 10 nM or 100 nM insulin, 0.1 mM 8-CPT, and 0.5 µM Dex in serum-free media for 6 hours. After these treatments, cells were collected and subjected to QRT-PCR analysis.

Figure 11:
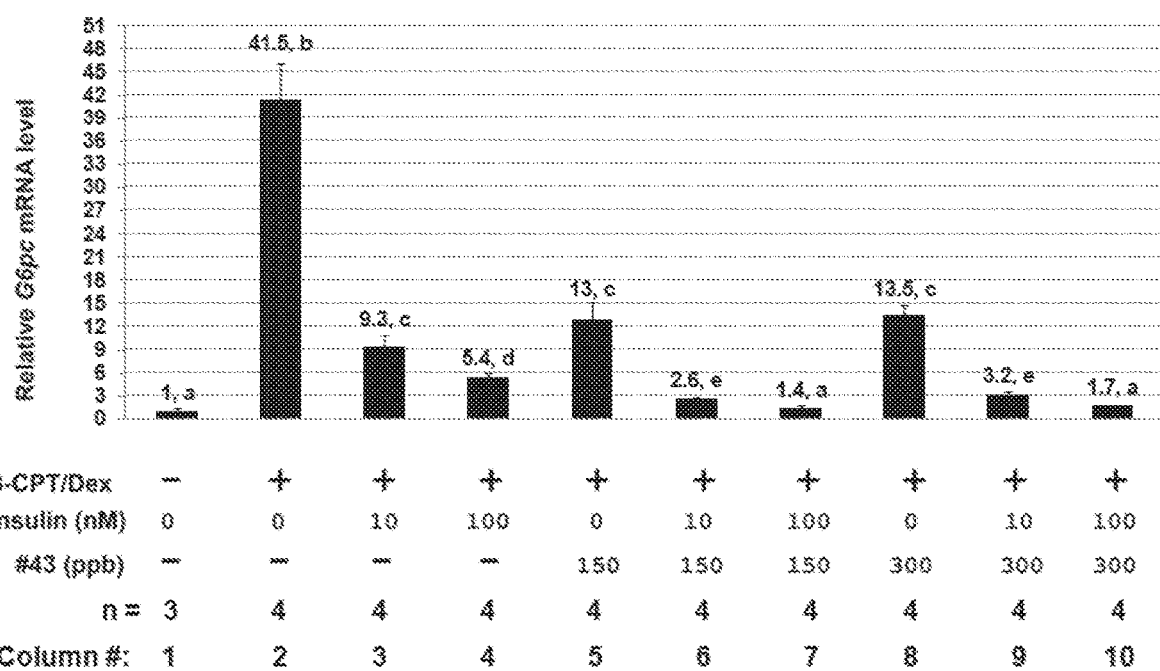
FIG. 11. Inhibition of G6pc expression by Compound #43, and the cooperative action of both Compound #43 and insulin in the inhibition of G6pc expression in AML-12 cells stimulated with diabetic stimuli. AML-12 cells were pretreated with Compound #43 in 10% FBS-containing but ITS/Dex-free media for 24 hours followed by retreatment of Compound #43 in the presence or absence of insulin along with 8-CPT/Dex (diabetic stimuli) in serum-free and ITS-free media for 6 hours. G6pc mRNA level in each sample was normalized by Actb mRNA level and data are presented as mean±SEM of indicated number of sample in each group. Numbers on the top of each column are the mean values of G6pc mRNA levels normalized by the level in non-8-CPT/Dex-treated group (Column #1). Different letters in the bars represents a statistical significance (P<0.05) between those two groups.

As shown in FIG. 11, AML-12 liver cells treated with 8-CPT/Dex resulted in a 41.5-fold increase in the expression of G6pc mRNA (Column #1 vs #2). Treatment with both doses of insulin significantly decreased 8-CPT/Dex-induced G6pc expression in AML-12 cells, when compared to the 8-CPT/Dex group (Column #3-4 vs Column #2 in FIG. 11). Further, Compound #43 at the doses of 150 and 300 ppb also significantly attenuated 8-CPT/Dex-induced G6pc expression (decreased from 41.5 in Column #2 to 13 in Column #5 and 13.5 in Column #8, FIG. 11) with a potency comparable to 10 nM insulin (Column #3, FIG. 11). These studies demonstrated that, like insulin, Compound #43 alone at the tested doses can inhibit 8-CPT/Dex-induced G6pc expression (about a 68% reduction when compared to the 8-CPT/Dex group, Column #5 and #8 vs #2 in FIG. 11).

In addition, treatment of Compound #43 in combination with insulin (Column #6-7 and Column #9-10 in FIG. 11) further inhibited 8-CPT/Dex-induced G6pc expression in AML-12 cells when compared to no insulin/Compound #43 treatment (Column #2), insulin alone (Column #3-4) or Compound #43 alone (Column #5 and #8 in FIG. 11). More dramatically, G6pc mRNA levels in the treatment with Compound #43 at 150 ppb in combination with 100 nM of insulin along with 8-CPT/Dex (Column #7), and in the treatment with Compound #43 at 300 ppb in combination with 100 nM of insulin along with 8-CPT/Dex (Column #10) were robustly decreased from the levels of 8-CPT/Dex treatment alone (Column #2) to the levels (Column #7, #10) close to the no-8-CPT/Dex control group (Column #1 in FIG. 11). In other words, co-treatment of Compound #43 (150 or 300 ppb) with 100 nM of insulin almost completely abolished 8-CPT/Dex-induced G6pc expression in AML-12 cells.

Together, these results demonstrate that, like insulin, Compound #43 alone at the tested doses can inhibit 8-CPT/Dex-induced G6pc expression and the combination of both insulin and Compound #43 was even more effective than insulin alone or Compound #43 alone in inhibiting increased expression of G6pc due to 8-CPT/Dex treatment in AML-12 cells.

The effects of the above decreased G6pc expression in response to the selenium compounds was not due to the potential toxic effects of these selenium compounds on cell survival, since these compounds at the tested dose did not affect the viability of AML-12 or HepG2 cells under the same experimental conditions (data not shown).

In summary, these results demonstrated that there is a differential effect of Compound #43 and #50 on the inhibition of G6pc expression in the liver. At a minimum, the data demonstrate that Compound #43 is a potent compound to inhibit G6pc expression in the liver both in vivo and in vitro. The studies further revealed that Compound #43 can mimic but bypass insulin to directly inhibit G6pc expression in mouse and human liver cells cultured under both normal conditions and conditions simulating diabetes (i.e., treatment of cells with 8-CPT/Dex). In addition, Compound #43 can improve insulin action to inhibit G6pc expression in AML-12 cells cultured under both normal and simulated diabetic conditions. Together, these results provide the molecular evidence that Compound #43 can inhibit G6pc expression in the liver both in vivo and in vitro and thus may be a valuable treatment for Type I and Type II diabetics.

Example 5: Compound #43 Mimics but Bypasses Insulin to Activate Phosphoinositide-Dependent Protein Kinase 1 (PDK1) and Protein Kinase B (AKT) Signaling to Enhance the Phosphorylation of Forkhead Box Protein O1 (FOXO1) in the Liver In Vivo and In Vitro The Forkhead transcription factor FOXO1 plays a critical role in metabolism, gluconeogenesis and insulin sensitivity in the liver. Intracellular activity of FOXO1 is tightly regulated by post-translational modification. In particular, phosphorylation of FOXO1 excludes FOXO1 from the nucleus, thereby blocking its access to its target genes such as G6pc in the liver for glucose production. In insulin-resistant or diabetic individuals, there is no signal to exclude FOXO1 from the nucleus, so it remains present in the nucleus and stimulates the transcription of G6pc. Increased expression of G6pc drives gluconeogenesis, leading to hyperglycemia.

As described above, the results in vivo and in vitro demonstrated that Compound #43 can mimic but bypass insulin action to inhibit G6pc expression and can improve insulin action in the process. Since FOXO1 is the major signaling molecule for gluconeogenesis and insulin sensitivity in the liver and PDK1 and AKT are two major intermediate signaling molecules upstream of FOXO1, the question as to whether Compound #43, like insulin, will target FOXO1 and its upstream signaling molecules, PDK1 and AKT, in $Lepr^{db/db}$ mice, human liver HepG2 and mouse liver AML-12 cells was examined.

Materials and Methods
Compounds

Compound #43 was synthesized in the Chemistry Laboratory of Alltech, Inc. The purity of this tested compound was verified to be ≥99%, as determined by HPLC.

In Vivo Treatment of Compound #43 in $Lepr^{db/db}$ Mice and Liver Protein Preparation Male $Lepr^{db/db}$ mice (C57BL/6J strain, purchased from The Jackson Laboratory) at postnatal day 38 were intraperitoneally injected daily with physiological saline (0.09% NaCl) containing 0.2% DMSO, Compound #43 (25 µg selenium or sulfur equivalent of each compound per kilogram body weight, diluted in sterile physiological saline) for 52 days. After the treatment, livers were collected and stored at −80° C.

Frozen liver tissues were minced in sterile ice-old PBS containing complete proteinase and phosphatase inhibitors (Thermo-Fisher Scientific, Waltham, Mass.) and subjected to homogenization using a tissue homogenizer (Thermo-Fisher Scientific, Waltham, Mass.). These tissue homogenates were diluted in Themo-Fisher's premade RIPA buffer (1 part homogenate/2 part of RIPA buffer) containing complete proteinase/phosphatase inhibitors to extract the proteins. Proteins in the homogenates were extracted in RIPA buffer at 4° C. overnight. These overnight-extracted protein lysates were centrifuged at 12000×g for 30 min at 4° C., and the protein levels in the supernatant of these tissue lysates were determined using the Pierce Micro-BCA protein assay kit (Thermo Scientific-Piece Biotechnology, Rockford, Ill.) according to the manufacturer's protocol.

Cell Culture

Human hepatoma HepG2 and mouse liver AML-12 cell lines were purchased from the American Type Culture Collection (ATCC, Manassas, Va.). HepG2 cells were cultured in Eagle's Minimum Essential Medium (EMEM) supplemented with 10% FBS. AML-12 cells were amplified in Dulbecco's modified Eagle's medium and Ham's F12 (DMEM/F12) media supplemented with 10% fetal bovine serum (FBS), 40 ng/ml dexamethasone (Dex, Sigma) and 1×ITS (containing 0.01 mg/ml bovine insulin, 0.0055 mg/ml human transferrin, 5 ng/ml sodium selenium) solution (Sigma).

Cell Treatments for Protein Analysis

HepG2 cells were seeded on 6-well plates ($7 \times 10^5$ cells/well) and cultured in 10% FBS EMEM media for 30 hr. Then these cells were washed twice with PBS to remove residual sera, and serum-starved in plain EMEM media overnight. These serum-starved HepG2 cells were treated without or with Compound #43 (600 ppb) for 0 minute (right before the treatment), 30 minutes, 60 minutes, 90 minutes, 24 hr, 30 hr and 40 hr.

AML-12 cells were used to investigate whether Compound #43 can regulate Pdk1/Akt/Foxo1 signaling molecules in the liver cells following induction with diabetic stimuli. Amplified AML-12 cells were seeded on 6-well ($1 \times 10^6$ cells/well) plates and cultured in 10% FBS but ITS/Dex-free DMEM/F12 media for 24 hr. Then these cells were washed twice with PBS to remove residual sera, and serum-starved in plain DMEM/F12 media overnight. These serum-starved AML12 cells were treated with the diabetic stimuli 8-CPT (0.1 mM) and Dex (0.5 µM) in combination, without (Control group) or with 10 nM insulin or Compound #43 (300 ppb) in serum-free plain DMEM/F12 media for 60 minutes, 90 minutes, and 6 hr, respectively.

After the above described treatments, cultured HepG2 and AML-12 cells were rinsed twice with ice-cold PBS and lysed in ice-cold RIPA buffer containing complete proteinase and phosphatase inhibitors (Thermo-Fisher Scientific, Waltham, Mass.) on ice for 30 min. Cell lysates were collected using a cell scraper and transfer pipette, and then centrifuged at 12000×g for 30 min at 4° C. to remove the DNA pellet and obtain the protein extract. Protein levels in the supernatant of these cell lysates were determined using the Pierce Micro-BCA protein assay kit (Thermo Scientific-Piece Biotechnology, Rockford, Ill.) according to the manufacturer's protocol.

Western Blot Analysis

One hundred micrograms of liver tissue proteins or five micrograms of total proteins from control- and compound(s)-treated HepG2 or AML-12 cells were subjected to SDS-PAGE gel separation and then transferred to PVDF membranes, as described previously (Reddy et al. 2008 Science). Membranes were blocked in a phosphate-buffered saline (PBS) containing 5% (w/v) of bovine serum albumin (Sigma, St. Louis, Mo.) and incubated with specific primary antibodies followed by the incubation with HRP-conjugated anti-mouse or anti-rabbit secondary antibodies (1:5000 dilution, Cell Signaling Inc.). All primary antibodies except Gapdh (Li-COR, Lincoln, Nebr.) were purchased from Cell Signaling Inc. Positive signals on the membrane blots were detected using the Amersham's enhanced chemiluminescence Western Blotting Prime Detection reagents (GE Healthcare Lifescience, Pittsburgh, Pa.). Images of these luminescence signals on the membrane blots were captured using the LI-COR Odyssey Fc Image system (Lincoln, Nebr.). The same membrane blot was stripped and re-blotted with another antibody as described in the GE WB ECL-prime-detection protocol (GE healthcare Lifescience, Pittsburgh, Pa.). Protein band densities in the Western blots were determined using the NIH ImageJ software and then normalized by Gapdh or Actb/ACTB level in each sample. Data are presented as mean±SEM of three samples per each group.

Statistical Analysis

If applicable, a Student's t-test was performed to determine the statistical difference between two groups. A P-value less than 0.05 was considered significant.

Results:

1. Enhanced Phosphorylation of Pdk1, Akt and Foxo1 in the Livers of Insulin-Resistant Lepr$^{db/db}$ Mice after Chronic Treatment with Compound #43

The animal studies revealed that Compound #43 can reduce blood glucose and HbA1c levels and inhibit liver G6pc expression in Lepr$^{db/db}$ mice (FIG. 3-7, 9). The reduced fasting glucose levels and blood HbA1c levels are at least in part attributed to the attenuated expression of the gluconeogenic G6pc gene in the livers of Lepr$^{db/db}$ mice. G6pc expression in the liver is controlled by the insulin signaling Pdk1/Akt/Foxo1 cascade. Therefore, the application investigates whether the chronic treatment of Compound #43 can restore, at least to some extent, the insulin signaling (i.e., enhancing the phosphorylation of Pdk1/Akt/Foxo) in the livers of these insulin-resistant Lepr$^{db/db}$ mice.

Lepr$^{db/db}$ mice at postnatal day 38 were intraperitoneally injected with saline or Compound #43 at the dose of 25 µg selenium per kilogram body weight daily for 52 days. After the above treatments, liver tissues were collected and subjected to Western blot analysis using specific antibodies against the insulin signaling molecules. As shown in FIG. 12A, protein signals of phosphorylated-Pdk1, -Akt at Threonine 308, and -Foxo1 at Serine 256 in the livers of Compound #43-treated mice were visibly more abundant than those in saline-treated mice. Quantitative analysis of these Western blots showed the protein levels of pPdk1, pAkt and pFoxo1 were significantly elevated in the livers of Lepr$^{db/db}$ mice after treatment with Compound #43 (FIG. 12B). In contrast, there was no significant change in total Akt levels in Compound #43-treated mice. The increased phosphorylation of Pdk1, Akt and Foxo1 strongly suggests that the insulin downstream signaling cascade is active in the livers of Lepr$^{db/db}$ mice after chronic treatment with Compound #43, even though Lepr$^{db/db}$ mice are known to be unable to respond to insulin. In other words, the results demonstrate that Compound #43 can either restore insulin action at least partly, bypass insulin, or both, to stimulate the phosphorylation of Pdk1/Akt/Foxo1, resulting in the attenuation of G6pc expression and glucose production in the livers of these insulin-resistant diabetic mice.

2. Compound #43 Mimics but Bypasses Insulin to Transiently Activate PDK1/AKT and Subsequently Inactivate FOXO1 in Human HepG2 Cells Cultured in Serum-Free Media To investigate whether there is an insulin-independent but insulin-like effect of Compound #43 in the liver to regulate the phosphorylation of PDK1, AKT and FOXO1, serum-starved human HepG2 cells were treated with control, and 600 ppb of Compound #43 in serum-free media for various times, ranging from 30 min to 48 hours. Treated cells were subjected to Western blot analysis.

As shown in FIG. 13A, there was a visibly increased protein signal for phosphorylated PDK1 in HepG2 cells after treatment with Compound #43 for 30, 60 and 90 minutes, but not at longer treatment time points (after 24 hr treatment). Quantitative studies showed there was a significant and transient increase of pPDK1 in HepG2 cells after Compound #43 treatment, with the peak increase at about 60-90 minutes after compound treatment (FIG. 13B). Similarly, a significant and transient increase of phosphorylated AKT at T308 was also observed in HepG2 cells after Compound #43 treatment for 30, 60, 90 minutes and 24 hr, with the peak increase at 60 and 90 minutes (FIG. 13A, C). In contrast, total AKT protein levels in all tested time points were not significantly altered in HepG2 cells after Compound #43 treatment (FIG. 13A, D).

The protein levels of phosphorylated FOXO1 at T24 were significantly increased in HepG2 cells after treatment with Compound #43 for 90 minutes and longer (FIG. 13A, E). The increased FOXO1 phosphorylation was observed later than the events of increased pPDK1 and pAKT (FIG. 13A, 13E vs 13B-C). There was no significant change in total FOXO1 protein levels in HepG2 cells after treatment with Compound #43 for less than 24 hours (FIG. 13A, 13F). However prolonged treatment of Compound #43 (30 hr or 48 hr) resulted in a slight but statistically significant decrease of total FOXO1 proteins in HepG2 cells (FIG. 13A, F), which could be due to the potentially increased proteasome protein degradation of FOXO1 resulting from continual elevation of phosphorylated FOXO1 in HepG2 cells. Phosphorylated FOXO1 is excluded from the nucleus meaning less nuclear FOXO1 and less G6pc expression as a direct result. Also, significantly reduced glucose production (FIG. 1) and G6PC expression (FIG. 10B) were observed in Compound #43-treated HepG2 cells, as well as reduced hyperglycemia and attenuated G6pc expression in the Compound #43-treated Lepr$^{db/db}$ mice (FIG. 3-7, 9).

Together, the above results demonstrated that Compound #43 can mimic but bypass insulin to transiently activate PDK1 and AKT, and subsequently inactivate FOXO1 in human liver HepG2 cells.

3. Compound #43 Mimics but Bypasses Insulin to Transiently Activate Pdk1/Akt and Subsequently Inactivate Foxo1 in AML-12 Cells Cultured Under Simulated Diabetic Conditions (Stimulated by Both 8-CPT and Dex)

As described in the previous Examples, Compound #43 can mimic but bypass insulin to inhibit 8-CPT/Dex-induced G6pc expression in AML-12 cells (FIG. 11). This effect could be due to the potential insulin-like activity of Compound #43 to inactivate Foxo1 in these mouse liver cells. Thus, the application examined the protein expression of insulin signaling molecules in AML-12 cells, cultured under simulated diabetic conditions (stimulated with 8-CPT and Dex).

As shown in FIG. 14A, insulin treatments enhanced the phosphorylation of Pdk1, Akt and Foxo1 at 60 and 90 minutes, indicating that AML-12 cells cultured under simulated diabetic conditions were responsive to insulin. Like insulin, Compound #43 also significantly induced the phosphorylation of Pdk1, Akt and Foxo1 in these 8-CPT/Dex-treated AML-12 cells after 60 minutes of compound treatment (FIG. 14A-B). At 90 minutes after compound treatment, a significant increase in pFoxo1 protein levels was observed in these AML-12 cells, while the protein levels of all other tested molecules including pPdk1, pAkt, Akt, and Foxo1 were not significantly altered after Compound #43 treatment (FIG. 14A,C). At 6 hr of Compound #43 treatment, there was still a significant increase in pFoxo1 levels, and a slight but significant decrease in total Foxo1protein levels (FIG. 14A, D). The increased pFoxo1 and slightly decreased total Foxo1 protein levels at 6 hr treatment were also observed in AML-12 cells after the treatment with 10 nM of insulin (FIG. 14A, E). Once again, the slight decrease of total Foxo1 at 6 hr treatment could be due to the targeted proteasomal protein degradation of Foxo1 proteins resulting from continuous phosphorylation of Foxo1 in the cytosol of these AML-12 cells which had been subjected to diabetic stimuli. The enhanced Foxo1 phosphorylation after Compound #43 treatment may lead to decreased nuclear Foxo1 and attenuated 8-CPT/Dex-induced G6pc expression observed in FIG. 11. Together, the results suggest that Compound #43, like insulin, can transiently induce phosphorylation of Pdk1 and Akt and then induce Foxo1 phosphorylation in AML-12 cells cultured under simulated diabetic conditions.

In conclusion, the above in vitro and in vivo studies demonstrated that Compound #43 can mimic but bypass insulin to transiently activate Pdk/Akt and then inactive Foxo1 in the liver.

Example 6: Enhanced Glut4 (SLC2A4) Expression in the Livers of $Lepr^{db/db}$ Mice and Cultured Liver Cells, and Enhanced Glucose Uptake in Culture Liver Cells after Compound #43 Treatment The in vivo studies revealed that Compound #43 can lower blood glucose levels and improve the glucose clearance in insulin-resistant $Lepr^{db/db}$ mice (FIG. 3-8). This is partially due to attenuated glucose production in the liver but could also result from increased glucose uptake from the bloodstream to the peripheral tissues including the liver. Glut4 is a critical glucose transporter and an indirect Foxo1 target gene for glucose uptake in the liver, in response to systemic insulin stimuli. Therefore, $Lepr^{db/db}$ mice and cultured mouse liver AML-12 cells were treated with Compound #43 to test its potential effect on Glut4 expression and glucose uptake in the liver.
Materials and Methods
Compounds Compound #43 and Compound #50 were synthesized in the Chemistry Laboratory of Alltech, Inc. The purities of all these compounds were verified to be ≥99%, as determined by HPLC.
In Vivo Treatment of Compound #43 and #50 in $Lepr^{db/db}$ Mice Male $Lepr^{db/db}$ mice (C57BL/6J strain, purchased from The Jackson Laboratory) at postnatal day 38 were intraperitoneally injected daily with physiological saline (0.09% NaCl) containing 0.2% DMSO, Compound #43, or Compound #50 (25 µg selenium of each compound per kilogram body weight, diluted in sterile physiological saline) for 52 days. After treatment, livers were collected and subjected to RNA analysis.
Cell Culture Mouse liver AML-12 cells were purchased from the American Type Culture Collection (ATCC, Manassas, Va.). These cells were amplified in Dulbecco's modified Eagle's medium and Ham's F12 (DMEM/F12) media supplemented with 10% fetal bovine serum (FBS), 40 ng/ml dexamethasone (Dex, Sigma) and 1×ITS (containing 0.01 mg/ml bovine insulin, 0.0055 mg/ml human transferrin, 5 ng/ml sodium selenium) solution (Sigma).
Cell Treatments for RNA Analysis For RNA analysis of basal Glut4 (Slc2a4) expression (in the absence of diabetic stimuli 8-CPT/Dex), amplified AML-12 cells were cultured on 24-well ($1\times10^5$ cells/well) plates overnight in 10% FBS ITS- and Dex-free DMEM/F12 media. These cells were washed twice with PBS to remove residual sera and then were incubated with vehicle (0.024% DMSO) or with Compound #43 (300 ppb) in serum-free DMEM/F12 media for 24 hours.

For RNA analysis of Glut4 expression in AML-12 cells cultured under simulated diabetic conditions, amplified AML-12 cells were cultured on 24-well ($2\times10^5$ cells/well) plates in 10% FBS ITS- and Dex-free DMEM/F12 media overnight. Then these cells were washed twice with PBS to remove any potential residual sera and then were serum-starved in plain DMEM/F12 media overnight. These serum-starved AML-12 cells were then incubated with vehicle (0.024% DMSO) or with Compound #43 (300 ppb) in the presence of diabetic stimuli, 0.1 mM 8-CPT (Sigma) and 0.5 µM Dex, in serum-free plain DMEM/F12 media for 6 and 24 hours.
RNA Isolation and Real-Time PCR Analysis Total liver RNA from saline- or Compound #43-treated $Lepr^{db/db}$ mice was isolated using a Qiagen RNAeasy RNA isolation kit according to the Manufacturer's protocol. Total RNA from cultured cells was isolated using Trizol (Invitrogen) according to the manufacturer's protocol, and then incubated with DNase I to remove any potential contaminating genomic DNA. RNA samples were subjected to real-time PCR analysis using Applied-Bioscience's RT kit and predesigned Taqman probes (Invitrogen), as described previously (Lan et al EMBO J 2003). Data were normalized by Actin B (Actb) mRNA levels in each sample and are presented as mean±SEM of 3-5 samples.
Glucose Uptake Assay Equal numbers of amplified AML-12 cells were seeded on 96 well plates ($1.5\times10^5$/well) and cultured in 10% FBS but ITS/Dex-free DMEM/F12 media overnight. Then these cells were washed twice with PBS (to remove any potential residual sera), and serum-starved in plain DMEM/F12 media overnight. These serum-starved AML-12 cells were treated without (basal), with insulin (10 and 100 nM) or Compound #43 (150, 300 and 600 ppb) in glucose/phenol red-free DMEM media at 37° C. for 1.5 hr. After treatment, media was removed and cells were washed once with PBS and incubated with 1 mM 2-deoxyglucose (2DG) at room temperature for 30 min. The 2DG-treated cells were then subjected to glucose uptake measurement using Promega's Glucose Uptake-Glo Assay kit, according to the manufacturer's protocol. Luminescent signals were recorded using a Bio-Tek luminometer.
Statistical Analysis Where applicable, a Student's t-test was used to determine the statistical significance of differences among different treatment groups, with a P value less than 0.05 taken to represent a significant result.
Results:
1. Analysis of Glut4 mRNA expression in the livers of $Lepr^{db/db}$ mice after chronic treatment with Compounds #43 and Compound #50

Male $Lepr^{db/db}$ mice at postnatal day 38 were intraperitoneally injected daily with physiological saline (0.09% NaCl) containing 0.2% DMSO, Compound #43, or Compound #50 (25 µg selenium equivalent of each compound per kilogram body weight, diluted in sterile physiological saline) for 52 days. After these compound treatments, livers were collected and subjected to RNA analysis of Glut4 and Actb mRNA.

Figure 15:
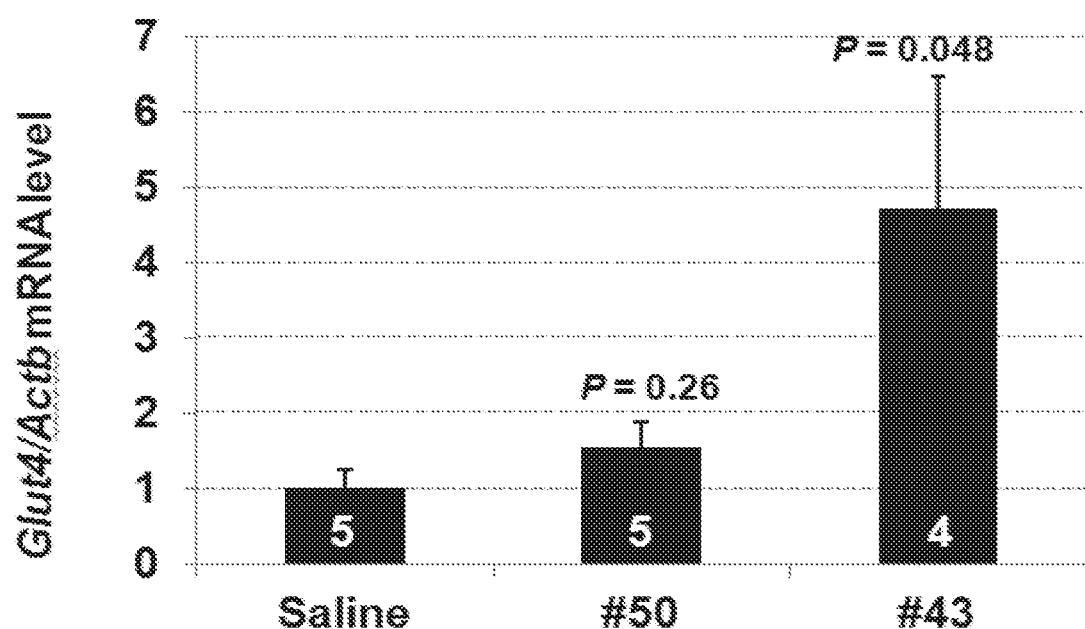
FIG. 15. Effects of Compound #43 and Compound #50 on the expression of the Glut4 gene in the livers of $Lepr^{db/db}$ mice. $Lepr^{db/db}$ mice at postnatal day 38 were intraperitoneally injected with saline (containing 0.2% the compound solvent DMSO), Compound #50 or Compound #43 at a dose of 25 μg selenium of each compound per kilogram body weight daily for 52 days. QRT-PCR analyses were performed on liver RNA samples isolated from these compound-treated $Lepr^{db/db}$ mice. Glut4 mRNA level in each sample was normalized by Actb mRNA level, and data are presented as mean±SEM of four to five mice per group. P values were calculated for treatment versus the control saline group.

As shown in FIG. 15, Compound #50 treatments numerically increased Glut4 mRNA levels in the livers of $Lepr^{db/db}$ mice (when compared to the saline-treated group). However, Compound #43 treatment elicited a large and significant increase (5-fold; P=0.048) in Glut4 mRNA expression levels in the livers of Lepr$^{db/db}$ mice (FIG. 15). These results suggest that there are distinct differences between these two selenium compounds in the stimulation of Glut4 expression in the liver and that Compound #43 is a potent enhancer of Glut4 expression in this organ. These results also suggest that reduced blood glucose levels and improved glucose tolerance observed in Compound #43-treated Lepr$^{db/db}$ mice (FIG. 3-8) could be partly due to enhanced Glut4 expression, resulting in increased glucose uptake from the bloodstream into the liver of diabetic subjects.

2. Enhanced Glut4 mRNA Expression after Compound #43 Treatment in Mouse Liver AML-12 Cells with or without the Stimulation of Diabetic Stimuli (8-CPT/Dex)

The above in vivo studies revealed that Compound #43 can significantly stimulate Glut4 expression in the liver of insulin-resistant Lepr$^{db/db}$ mice. This could be due to the potential systemic effect of Compound #43 or the potential direct effect of Compound #43 on the liver tissue. To test the latter scenario, cultured liver cells were used to examine whether Compound #43 can directly regulate Glut4 expression in the liver.

Figure 16:
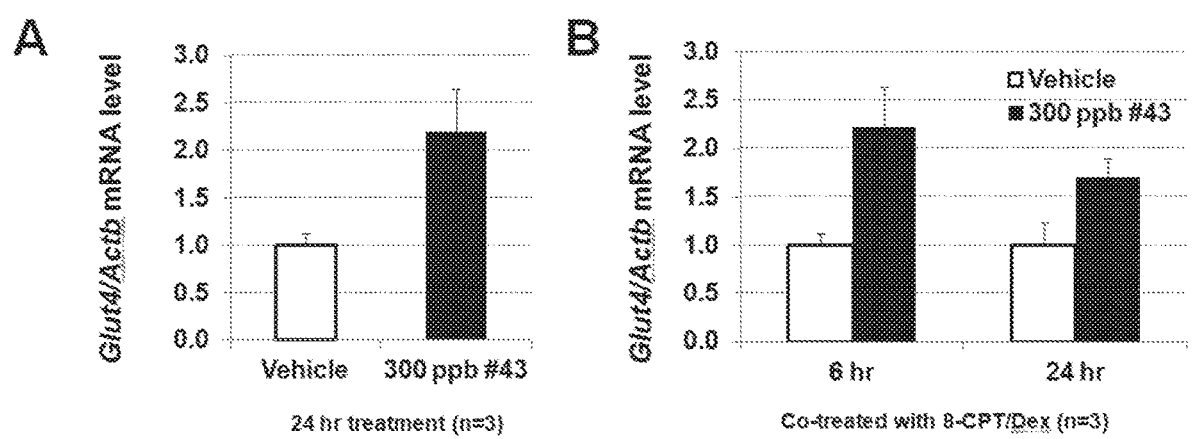
FIG. 16. Enhanced Glut4 mRNA expression in mouse liver AML-12 cells by Compound #43. (A) QRT-PCR of basal Glut4 expression in AML-12 cells. AML-12 cells were amplified, seeded on 24-well plates, and cultured in 10% FBS ITS/Dex-free DMEM/F12 media overnight. These cells were then incubated with vehicle (0.024% DMSO) or Compound #43 (300 ppb) in serum-free DMEM/F12 media for 24 hours (hr). (B) QRT-PCR of Glut4 expression in AML-12 cells cultured under simulated diabetic conditions. Amplified AML-12 cells were cultured on 24-well plates in 10% FBS but ITS/Dex-free DMEM/F12 media for 24 hr, and then serum-starved in plain DMEM/F12 media overnight. Serum-starved AML-12 cells were then incubated with vehicle (0.024% DMSO) or with Compound #43 (300 ppb) in the presence of diabetic stimuli, 0.1 mM 8-CPT and 0.5 μM Dex, in serum-free plain DMEM/F12 media for 6 and 24 hr. Glut4 mRNA level in each sample was normalized by Actb mRNA level, and data are presented as mean±SEM of 3 samples.

It was investigated whether Compound #43 could regulate basal Glut4 expression in normal AML-12 cells (without the application of diabetic stimuli). In brief, AML-12 cells were treated with vehicle (0.024% DMSO) and Compound #43 (300 ppb) in serum-free and ITS/Dex-free media for 24 hours, and subject to RNA analysis of Glut4 and Actb expression. As shown in FIG. 16A, treatment of Compound #43 (300 ppb) resulted in a significant increase (about 2.1-fold increase) of Glut4 mRNA expression in AML-12 cells. Considering that this experiment was performed on AML-12 cells cultured under totally serum-free conditions, the results suggest that enhanced Glut4 expression after Compound #43 treatment in AML-12 cells is insulin-, serum- or any growth factor-independent.

To further test whether Compound #43 can regulate Glut4 expression, AML-12 cells which had been subjected to diabetic stimuli were used. In brief, AML-12 cells were serum-starved overnight, and then incubated with vehicle (0.024% DMSO) or with Compound #43 (300 ppb) in the presence of diabetic stimuli, 0.1 mM 8-CPT (Sigma) and 0.5 µM Dex, in serum-free plain DMEM/F12 media for 6 and 24 hours. As shown in FIG. 16B, treatment of Compound #43 for both 6 and 24 hours resulted in a significant increase in Glut4 mRNA expression in these AML-12 cells co-treated with the diabetic stimuli, 8-CPT and Dex. Thus, these results demonstrate that Compound #43 can directly regulate Glut4 expression in AML-12 cells cultured under the simulated diabetic conditions.

3. Compound #43 Mimics but Bypasses Insulin to Enhance Glucose Uptake in Mouse Liver AML-12 Cells Enhanced Glut4 expression suggests that Compound #43 likely can mimic, yet bypass insulin to enhance glucose uptake in the liver. To test this, glucose uptake experiments were conducted on mouse liver AML-12 cells. In brief, equal numbers of AML-12 cells were seeded on 96 well plates, cultured in 10% FBS but ITS/Dex-free DMEM/F12 media for 24 hr, and then serum-starved in plain DMEM/F12 media overnight. These serum-starved AML-12 cells were treated with insulin (10 and 100 nM) or Compound #43 (150, 300 and 600 ppb) in glucose/phenol red/serum-free DMEM media at 37° C. for 1.5 hr. After the treatments, cells were incubated with 1 mM 2-deoxyglucose (2DG) at room temperature for 30 minutes, and then subjected to luminescence analysis using Promega's Glucose Uptake-Glo Assay kit. The detected luminescent signals represent the glucose uptake into the cultured cells.

Figure 17:
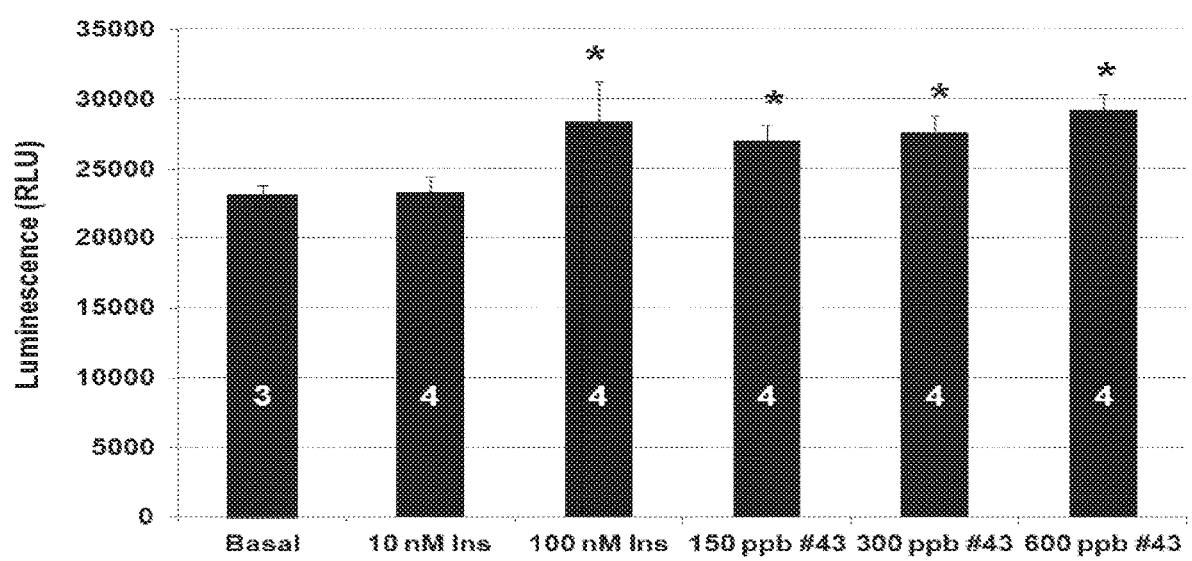
FIG. 17. Enhanced glucose uptake in AML-12 cells after the treatment of insulin and Compound #43 for 1.5 hours. Data are presented as mean±SEM of the indicated number of samples per group. * P value was less than 0.05, compared to the basal group.

As shown in FIG. 17, treatment with 10 nM of insulin did not enhance the glucose uptake. However, treatment of 100 nM of insulin resulted in a significant increase of glucose uptake in AML-12 cells. Further, treatment of Compound #43 at all three tested doses resulted in a significant increase of glucose uptake, and the extent of increased glucose uptake in AML-12 cells treated with 600 ppb of Compound #43 was comparable to 100 nM insulin (FIG. 17). Since AML-12 cells were treated with Compound #43 under serum-free condition, the results indicate that like insulin, Compound #43 can act rapidly (less than 1.5 hr) to directly stimulate glucose uptake in the liver cells. The increased glucose uptake in the liver could be one of the reasons why Compound #43 can lower blood glucose level and improve glucose clearance in the insulin-resistant Lepr$^{db/db}$ mice (FIG. 3-8).

Example 7: Enhanced Expression of the Key Downstream Molecules of Insulin Signaling, Phosphorylated Pdk1, Akt and Foxo1, in the Skeletal Muscle of Insulin-Resistant Lepr$^{db/db}$ Mice, and the Cooperative Action of Both Insulin and Compound #43 in the Stimulation of Glucose Uptake in the Differentiated C2C12 (Skeletal Muscle) Cells Materials and Methods
Compounds Compound #43 was synthesized in the Chemistry Laboratory of Alltech, Inc. The purity of this tested compound was verified to be ≥99%, as determined by HPLC.

In Vivo Treatment of Compound #43 in Lepr$^{db/db}$ Mice

Male Lepr$^{db/db}$ mice (C57BL/6J strain, purchased from The Jackson Laboratory) at 38 days of age were intraperitoneally injected daily with physiological saline (0.09% NaCl) containing 0.2% DMSO or 0.136 mg of Compound #43 per kilogram body weight, diluted in the sterile physiological saline) for 52 days. After the treatment, gastrocnemius skeletal muscle samples were collected and stored at −80° C.

Skeletal Muscle Protein Preparation and Western Blot Analysis

Frozen skeletal muscles were minced in sterile ice-old PBS containing complete proteinase and phosphatase inhibitors (Thermo-Fisher Scientific, Waltham, Mass.) and subjected to homogenization using a tissue homogenizer (Thermo-Fisher Scientific, Waltham, Mass.). These tissue homogenates were diluted in Themo-Fisher's RIPA buffer (1 part homogenate/2 part of RIPA buffer) containing complete proteinase/phosphatase inhibitors to extract the proteins. Proteins in the homogenates were extracted in RIPA buffer at 4° C. overnight. These overnight-extracted protein/tissue lysates were centrifuged at 12000×g for 30 min at 4° C., and the protein levels in the supernatant of these tissue lysates were determined using the Pierce Micro-BCA protein assay kit (Thermo Scientific-Piece Biotechnology, Rockford, Ill.) according to the manufacturer's protocol.

One hundred micrograms of skeletal muscle proteins were subjected to SDS-PAGE gel separation and then transferred to PVDF membranes, as described previously (Reddy et al. 2008 Science). Membranes were blocked in a phosphate-buffered saline (PBS) containing 5% (w/v) of bovine serum albumin (Sigma, St. Louis, Mo.) and incubated with specific primary antibodies followed by the incubation with HRP-conjugated anti-mouse or anti-rabbit secondary antibodies (1:5000 dilution, Cell Signaling Inc.). All primary antibodies were purchased from Cell Signaling Inc, except the antibodies against β-tubulin (LI-COR bioscience). Positive signals on the membrane blots were detected using Amersham's enhanced chemiluminescence Western Blotting Prime Detection reagents (GE Healthcare Lifescience, Pittsburgh, Pa.). Images of these luminescence signals on the membrane blots were captured using the LI-COR Odyssey Fc Image system (Lincoln, Nebr.). The same membrane blot was stripped and re-blotted with another antibody as described in the GE WB ECL-prime-detection protocol (GE healthcare Lifescience, Pittsburgh, Pa.). Protein band densities in the Western blots were determined using the NIH ImageJ software and then normalized by β-tubulin level in each sample. Data are presented as mean±SEM of 5 animal samples.

C2C12 Cell Culture, Differentiation of C2C12 Cells, and Glucose Uptake Analysis

The mouse myoblast C2C12 cells were purchased from the American Type Culture Collection (ATCC, Manassas, Va.). These cells were amplified in DMEM media supplemented with 10% FBS. Equal number of C2C12 cells were then seeded on 96-well plates (5000 cells/well) and cultured in 10% FBS DMEM media at 37° C. for 5 days. Cells were replenished daily with fresh 10% FBS DMEM media. At day 5 of culture, C2C12 cells were differentiated using 0.5% horse serum (Sigma)-containing DMEM media (differentiation media) continuing for 7 days with daily replacement of fresh differentiation media, as previously described (Misu et al, Cell Metabolism 12, 483-495, 2010). At day 7 post-differentiation, differentiated C2C12 cells were rinsed with PBS twice and pretreated without or with 0.006% DMSO (Compound #43 solvent) or Compound #43 (300 or 600 ppb) in serum-free glucose-free DMEM media overnight. Then these cells were washed once with PBS, and then treated without (basal) or with insulin (200 nM), Compound #43 (300 and 600 ppb), or both insulin and Compound #43 in glucose/phenol red-free DMEM media at 37° C. for 1.5 hr. After treatment, media was removed and cells were washed once with PBS and incubated with 1 mM 2-deoxyglucose (2DG) at room temperature for 30 min. The 2DG-treated cells were then subjected to glucose uptake using Promega's Glucose Uptake-Glo Assay kit, according to the manufacturer's protocol. Luminescent signals were recorded using a Bio-Tek luminometer.

Statistical Analysis

Where applicable, a Student's t-test was used to determine the statistical significance of differences among different treatment groups with a P value less than 0.05.

Results:

1. Increased Phosphorylation of Insulin Downstream Signaling Molecules—Pdk1, Akt and Foxo1—in Skeletal Muscles of Insulin-Resistant $Lepr^{db/db}$ Mice after the Chronic Treatment of Compound #43

Besides liver, skeletal muscle is the other major organ critical for glucose homeostasis in response to systemic insulin. Glucose uptake in skeletal muscle plays a key role in maintaining normal glucose levels in the bloodstream. The animal studies revealed that Compound #43 can reduce blood glucose and HbA1c levels, as well as significantly improving glucose tolerance in the insulin-resistant $Lepr^{db/db}$ mice (FIG. 3-8). These effects could be due to restoration of insulin signaling (i.e., Pdk1/Akt) in the skeletal muscle to stimulate glucose uptake. Therefore, it was investigated whether chronic treatment of Compound #43 could partially repair damaged insulin signaling in the skeletal muscles of these insulin-resistant $Lepr^{db/db}$ mice.

$Lepr^{db/db}$ mice at postnatal day 38 were intraperitoneally injected with saline (containing 0.2% DMSO) or Compound #43 at the dose of 0.136 mg of Compound #43 per kilogram body weight daily for 52 days. After the above treatments, skeletal muscles were collected and subjected to Western blot analysis using specific antibodies against those insulin signaling molecules.

As shown in FIG. 18A, the protein band densities of phosphorylated Pdk1, Akt at Threonine 308, and Foxo1 at Serine 256, but not total Akt or Foxo1, were visibly higher in the skeletal muscles of Compound #43-treated mice than saline-treated mice. Quantitative analysis of these Western blots showed that pPdk1 protein levels were increased in the skeletal muscles of $Lepr^{db/db}$ mice after the treatments of Compound #43, when compared to saline-treated mice (FIG. 18B). The increased levels of pPdk1 in the skeletal muscles of Compound #43-treated mice approached statistical significance (P=0.11). Further, the protein levels of two Insulin/Pdk1 downstream signaling molecules, pAkt and pFoxo1, were significantly elevated in the skeletal muscles of $Lepr^{db/db}$ mice after treatment with Compound #43 (FIG. 18B). In contrast, there was no significant change of total Akt and Foxo1 protein levels in the skeletal muscles of Compound #43-treated mice. The increased phosphorylation of Pdk1 and the significant increase of phosphorylated Akt and phosphorylated Foxo1 suggest that the insulin downstream signaling cascade is active in the skeletal muscles of $Lepr^{db/db}$ mice after the chronic treatment of Compound #43, even though $Lepr^{db/db}$ mice are known to be unable to respond to insulin. In other words, the results demonstrate that Compound #43 can restore insulin action, bypass insulin or both, to activate PI3K to induce the phosphorylation of Pdk1/Akt in skeletal muscle, thus allowing them to perform their key functions in the regulation of glucose homeostasis in these severely insulin-resistant type II diabetic mice.

2. Enhanced Glucose Uptake in Differentiated Mouse C2C12 (Skeletal Muscle) Cells after the Treatment of Both Insulin and Compound #43

In humans and other mammals, skeletal muscle normally accounts for 75% of whole body insulin-stimulated glucose uptake. Impaired ability of skeletal muscle to respond to insulin is severely disruptive to systemic glucose homeostasis. It is well documented that the process of glucose uptake in skeletal muscle is mainly mediated through the PI3K/Pdk1/Akt signaling cascade in response to insulin. The activation of PI3K/Pdk1/Akt signaling molecules in the skeletal muscle of the insulin-resistant $Lepr^{db/db}$ mice (FIG. 18) suggests that Compound #43 likely can directly regulate glucose uptake in the skeletal muscle and potentiate insulin action in the process. To test these possibilities, glucose uptake experiments were conducted on the differentiated mouse C2C12 (skeletal muscle) cells.

In brief, equal numbers of C2C12 cells were seeded on 96-well plates (5000 cells/well), and cultured in 10% FBS DMEM media at 37° C. for 5 days. These cells were differentiated using 0.5% horse serum (Sigma)-containing DMEM media for 7 days to become skeletal muscle cells, as previously described (Misu et al, Cell Metabolism 12, 483-495, 2010). The completely differentiated C2C12 cells were pretreated without or with 0.006% DMSO (Compound #43 solvent) or Compound #43 (300 or 600 ppb) in serum-free glucose-free DMEM media overnight. Then these cells were incubated without (basal) or with insulin (200 nM), Compound #43 (300 and 600 ppb), or both insulin and Compound #43, in glucose/phenol red-free DMEM media at 37° C. for 1.5 hr. After treatments, cells were incubated with 1 mM 2-deoxyglucose (2DG) at room temperature for 30 minutes, and then subjected to luminescence analysis using the Promega's Glucose Uptake-Glo Assay kit. The detected luminescent signals represent the glucose uptake into the cultured differentiated C2C12 cells.

Figure 19:
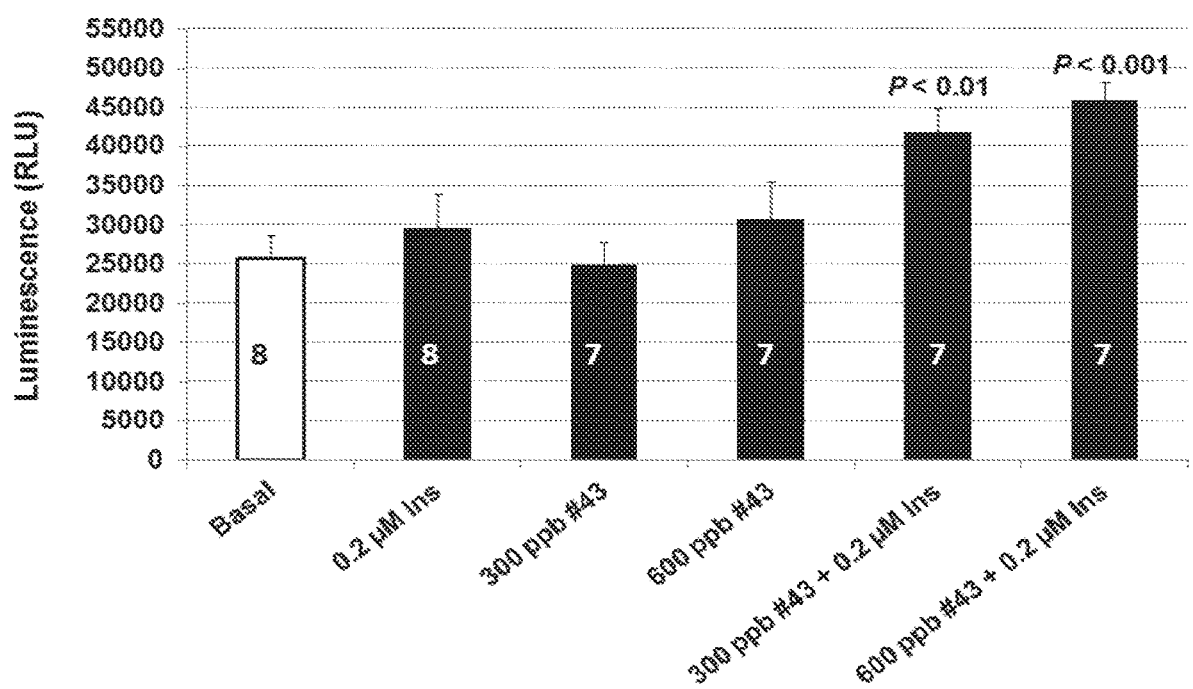
FIG. 19. Effects of insulin and Compound #43 on the glucose uptake in the differentiated mouse C2C12 (skeletal muscle) cells. Equal number of C2C12 cells were seeded on 96-well plates (5000 cells/well), cultured in 10% FBS DMEM media for 5 days, differentiated in 0.5% horse serum-containing DMEM media for 7 days. The completely differentiated C2C12 cells were pretreated without or with Compound #43 (300 or 600 ppb) in serum/glucose-free DMEM media overnight, and then incubated without (basal) or with insulin, Compound #43, or both in glucose-free DMEM media at 37° C. for 1.5 hr. After the treatments, cells were incubated with 1 mM of 2-deoxyglucose (2DG) at room temperature for 30 minutes, and then subjected to luminescence analysis using Promega's Glucose Uptake-Glo Assay kit. Data are presented as mean±SEM of indicated number of samples per group. P value was derived by comparison to the basal group.

As shown in FIG. 19, treatment with 200 nM of insulin alone or 600 ppb of Compound #43, but not 300 ppb of Compound #43, resulted in a 16-19% increase (albeit not statistically significant, when compared to basal group) of glucose uptake in these cultured skeletal muscle cells. Since there was a trend towards increased glucose uptake in these cultured skeletal muscle cells after the treatment of the higher dose (600 ppb) of Compound #43 with the potency similar to 200 nM of insulin, it is possible that Compound #43 at a dose of higher than 600 ppb can directly and significantly enhance glucose uptake in these differentiated muscle cells. Regardless, the results showed that Compound #43 at the tested dose of 600 ppb can stimulate glucose uptake with a potency comparable to 200 nM insulin.

Co-treatment of both insulin (200 nM) and Compound #43 (300 ppb) resulted in a robust and significant increase (63%) in glucose uptake by differentiated C2C12 cells (FIG. 19). A more pronounced increase (79%) of glucose uptake was observed in these differentiated cells after the co-treatment of 200 nM of insulin and 600 ppb of Compound #43. The extent of increased glucose uptake in differentiated C2C12 cells after co-treatment of both insulin and Compound #43 were much higher than insulin or Compound #43 alone, indicating that there was a synergistic action between insulin and Compound #43. Therefore, the above studies demonstrate that Compound #43 can cooperate with insulin to significantly enhance glucose uptake in differentiated skeletal muscle cells.

Together, the above studies suggest that Compound #43 can activate or restore the insulin signaling (as indicated by the enhanced phosphorylation of Pdk1/Akt/Foxo1) in the skeletal muscle of insulin-resistant diabetic $Lepr^{db/db}$ mice, and can potentiate insulin action to enhance the glucose uptake in the cultured skeletal muscle (differentiated C2C12) cells. These results provide further molecular evidence that Compound #43 can lower blood glucose levels and improve the glucose tolerance in the insulin-resistant $Lepr^{db/db}$ mice (FIG. 3-8).

Example 8: Activation of Insulin Receptor (Insr) Signaling in the Skeletal Muscle and Liver of Insulin-Resistant $Lepr^{db/db}$ Mice and in Cultured Mouse Skeletal Muscle and Human Liver Cells after Compound #43 Treatment, and Insulin-Like Effects of Compound #43 on the Phosphorylation of AS160-Key for GLUT4 Translocation from Cellular Vesicles to Plasma Membrane for Glucose Uptake-in the Differentiated Mouse C2C12 (Skeletal Muscle) Cells and Human Liver HepG2 Cells It is well documented that, after the binding of insulin to the alpha subunit of Insr, Insrβ undergoes tyrosine auto-phosphorylation starting at Y1146, then at Y1150/51, which subsequently activates PI3K/Pdk1 to induce the phosphorylation of Akt in the liver and skeletal muscle. AS160, also known as TBC1 domain family member 4 (TBC1D4), is an Akt substrate that plays a critical role in keeping GLUT4 proteins in cytosolic vesicles. Activation of Insr/PI3k/Pdk1/Akt signaling in response to insulin phosphor fates AS160, promoting the translocation of GLUT4 proteins from cytosolic vesicles to the plasma membrane to facilitate glucose uptake in skeletal muscle cells as well as into liver cells. Thus, the potential for Compound #43 to cause tyrosine phosphorylation of Insrβ was investigated in skeletal muscle and liver of insulin-resistant $Lepr^{db/db}$ mice and in differentiated mouse C2C12 (skeletal muscle) cells as well as human liver HepG2 cells. In addition, it was investigated whether Compound #43 could mimic but bypass insulin to activate Akt, the downstream signaling molecule of insulin receptor in differentiated mouse C2C12 cells. Further, the effects of Compound #43 on the phosphorylation of the Akt target substrate, AS160, were investigated in both differentiated mouse C2C12 and human liver HepG2 cells.

Materials and Methods
Compound

Compound #43 was synthesized in the Chemistry Laboratory of Alltech, Inc. The purity of this tested compound was verified to be ≥99%, as determined by HPLC.

In Vivo Treatment of Compound #43 in $Lepr^{db/db}$ Mice

Male $Lepr^{db/db}$ mice (C57BL/6J strain, purchased from The Jackson Laboratory) at postnatal day 38 were intraperitoneally injected daily with physiological saline (0.09% NaCl) containing 0.2% DMSO, or 0.136 mg of Compound #43 per kilogram body weight, diluted in the sterile physiological saline) for 52 days. After the treatment, gastrocnemius skeletal muscle and liver samples were collected and stored at −80° C.

Skeletal Muscle and Liver Protein Preparation

Frozen skeletal muscle and liver tissues were minced in sterile ice-old PBS containing complete proteinase and phosphatase inhibitors (Thermo-Fisher Scientific, Waltham, Mass.) and subjected to homogenization using a tissue homogenizer (Thermo-Fisher Scientific, Waltham, Mass.). These tissue homogenates were diluted in Themo-Fisher's premade RIPA buffer (1 part homogenate/2 part of RIPA buffer) containing complete proteinase/phosphatase inhibitors to extract the proteins. Proteins in the homogenates were extracted in RIPA buffer at 4° C. overnight. These overnight-extracted protein/tissue lysates were centrifuged at 12000×g for 30 min at 4° C., and the protein levels in the supernatant of these tissue lysates were determined using the Pierce Micro-BCA protein assay kit (Thermo Scientific-Piece Biotechnology, Rockford, Ill.) according to the manufacturer's protocol.

Cell Culture of HepG2 and C2C12 Cells, Differentiation of C2C12 Cells, Cell Treatments and Preparation of Cultured Cell Protein Extracts The human hepatoma HepG2 cells and mouse myoblast C2C12 cell lines were purchased from the American Type Culture Collection (ATCC, Manassas, Va.). HepG2 cells were cultured in Eagle's Minimum Essential Medium (EMEM) supplemented with 10% FBS, while C2C12 cells were amplified in DMEM media supplemented with 10% FBS.

HepG2 cells were seeded on 6-well plates ($7 \times 10^5$ cells/well) and cultured in 10% FBS EMEM media for 30 hr. Then these cells were washed twice with PBS to remove residual sera, and serum-starved in plain EMEM media overnight. These serum-starved HepG2 cells were treated without or with Compound #43 (600 ppb) in serum-free media for 0 minute (right before the treatment), 30 and 60 minutes.

To differentiate the C2C12 cells, equal number of these myoblast cells were firstly seeded on 12-well plates (60,000 cells/well) and cultured in 10% FBS DMEM media at 37° C. for 5 days. These cells were replenished daily with fresh 10% FBS DMEM media. At day 5 after the culture, C2C12 cells were differentiated using 0.5% horse serum (Sigma)-containing DMEM media (differentiation media) for 7 days with daily replacement of fresh differentiation media, similar to previous described (Misu et al, Cell Metabolism 12, 483-495, 2010). At day 7 after the differentiation, differentiated C2C12 cells were rinsed with PBS twice and incubated in serum-free DMEM media overnight. Then these serum-starved cells were treated without (basal) or with insulin (200 nM), Compound #43 (600 ppb), or both insulin and Compound #43 in serum-free DMEM media at 37° C. for 5 and 60 minutes.

After the above treatments, cultured HepG2 cells or differentiated C2C12 cells were rinsed twice with ice-cold PBS and lysed in ice-cold RIPA buffer containing complete proteinase and phosphatase inhibitors (Thermo-Fisher Scientific, Waltham, Mass.) on ice for 30 min. Cell lysates were collected using a cell scraper and transfer pipette, and then centrifuged at 12000×g for 30 min at 4° C. to remove the DNA pellet and obtain the protein extract. Protein levels in the supernatant of these cell lysates were determined using the Pierce Micro-BCA protein assay kit (Thermo Scientific-Piece Biotechnology, Rockford, Ill.) according to the manufacturer's protocol.

Western Blot Analysis

One hundred micrograms of skeletal muscle or liver tissue proteins, five micrograms of HepG2 cell protein extracts, or eight micrograms of differentiated C2C12 cell protein extracts were subjected to SDS-PAGE gel separation and then transferred to PVDF membranes, as described previously (Reddy et al. 2008 Science). Membranes were blocked in a phosphate-buffered saline (PBS) containing 5% (w/v) of bovine serum albumin (Sigma, St. Louis, Mo.) and incubated with specific primary antibodies followed by the incubation with HRP-conjugated anti-mouse or anti-rabbit secondary antibodies (1:5000 dilution, Cell Signaling Inc.). All primary antibodies were purchased from Cell Signaling Inc, except the antibodies against β-tubulin (LI-COR bioscience). Positive signals on the membrane blots were detected using the Amersham's enhanced chemiluminescence Western Blotting Prime Detection reagents (GE Healthcare Lifescience, Pittsburgh, Pa.). Images of these luminescence signals on the membrane blots were captured using the LI-COR Odyssey Fc Image system (Lincoln, Nebr.). The same membrane blot was stripped and re-blotted with another antibody as described in the GE WB ECL-prime-detection protocol (GE healthcare Lifescience, Pittsburgh, Pa.). Protein band densities in the Western blots were determined using the NIH ImageJ software and then normalized by β-tubulin or ACTB protein level in each sample. Data are presented as mean±SEM of 3-5 samples per group.

Enzyme-Linked Immunosorbent Assay (ELISA) of Phospho-Insrβ at Y1146 or Y1150/51

Liver protein samples from Saline- or Compound #43-treated Lepr$^{db/db}$ mice were subjected to ELISA assay using the PathScan Phospho-Insulin Receptor β (Tyr1146 or Tyr1150/1151) Sandwish ELISA kits (Cell Signaling Technology, Danvers, Mass.) according to the Manufacturer's protocols, with the exception of incubating protein extracts with the capturing pInsrβY1146 or pInsrβY1150/1151 antibodies at 4° C. overnight (instead of incubation at 37° C. for 2 hr as described in the protocol). Four hundred micrograms of liver protein extracts were used for the detection of phosphor-Insrβ at Y1146, and six hundred micrograms of liver protein extracts for the detection of phosphor-Insrβ at Y1150/1151. The absorbance at 450 nm (OD450) of tested samples was recorded using a Bio-tek microplater reader. The level of the internal protein control, β-tubulin, in each sample was determined by Western blot analysis using 100 μg of protein extract and a specific β-tubulin monoclonal antibody, followed by quantitative analysis of β-tubulin protein band density in the Western blot using the NIH Image J software. The OD450 of each tested sample was then normalized by its β-tubulin protein level to obtain the level of phospho-Insrβ at Y1146 or Y1150/1151.

Statistical Analysis

Where applicable, a Student's t-test was used to determine the statistical significance of difference among treatment groups, with a P value less than 0.05 being deemed significant.

Results:

1. Enhanced Tyrosine Phosphorylation of Insrβ in Skeletal Muscles of Insulin-Resistant Lepr$^{db/db}$ Mice after Chronic Treatment with Compound #43

As discussed above, skeletal muscle is absolutely essential for glucose homeostasis in response to systemic insulin. The animal studies revealed that Compound #43 can reduce blood glucose and HbA1c levels, and improve the glucose tolerance in the insulin-resistant Lepr$^{db/db}$ mice (FIG. 3-8). These effects could be due to the potential restoration of insulin receptor functioning in skeletal muscle, allowing glucose uptake to occur in these insulin-resistant Lepr$^{db/db}$ mice. The enhanced phosphorylation of Pdk1 and Akt in the skeletal muscle of Compound #43-treated insulin-resistant Lepr$^{db/db}$ mice (FIG. 18) suggest that Compound #43 may bypass but mimic insulin or restore the insulin action to activate the insulin signaling cascade molecules upstream of the Pdk1/Akt cascade in the skeletal muscle. Tyrosine phosphorylation of Insrβ at Y1146 reflects the first step of activated insulin receptor signaling following the binding of insulin to Insrα, and this is the key event upstream of PI3K/Pdk1/Akt signaling in skeletal muscle. Therefore, it was investigated whether chronic treatment with Compound #43 could regulate the phosphorylation of Insrβ in the skeletal muscle of these insulin-resistant Lepr$^{db/db}$ mice.

Lepr$^{db/db}$ mice at postnatal day 38 were intraperitoneally injected with saline (containing 0.2% compound solvent DMSO) or Compound #43 at a dose of 0.136 mg of Compound #43 per kilogram body weight daily for 52 days. After the above treatments, skeletal muscle samples were collected and subjected to Western blot analysis using specific antibodies against the aforementioned insulin signaling molecules.

Figure 18:
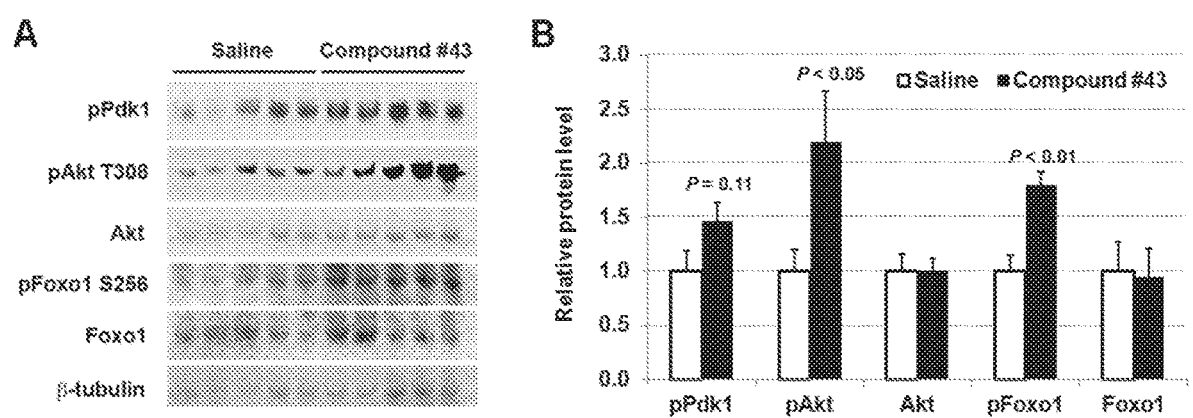
FIG. 18. Enhanced phosphorylation of insulin downstream signaling molecules—Pdk1, Akt and Foxo1—in skeletal muscles of insulin-resistant $Lepr^{db/db}$ mice in response to treatment with Compound #43. $Lepr^{db/db}$ mice at postnatal day 38 were intraperitoneally injected with saline (containing 0.2% the compound solvent DMSO) or Compound #43 at the dose of 0.136 mg of Compound #43 per kilogram body weight daily for 52 days. Western blots were performed on skeletal muscle protein extracts (100 µg protein per lane) isolated from saline or Compound #43-treated Lepr$^{db/db}$ mice. (A) Images of Western blots. (B) Quantitative protein levels (normalized by β-tubulin protein levels in each sample). Data are presented as mean±SEM of five mice. P value was derived by comparison to the control (saline) group.

As shown in FIG. 20A, the protein band densities of phosphorylated Insrβ at Tyrosine 1146, but not total Insrβ, were much higher in the skeletal muscle of Compound #43-treated Lepr$^{db/db}$ mice than saline-treated mice. Quantitative analysis of these Western blots showed that phosphorylated Insrβ protein levels were robustly increased (about a 2.5 fold-increase) in the skeletal muscle of Lepr$^{db/db}$ mice after treatment with Compound #43, when compared to saline-treated mice (FIG. 20B). In contrast, there was no significant change of total Insrβ protein levels in the skeletal muscles of Compound #43-treated mice (FIG. 20C). These results are consistent with the observation of increased phosphorylation of Pdk1 and Akt, the key insulin signaling molecules downstream of Insr in the skeletal muscle of Compound #43-treated Lepr$^{db/db}$ mice (FIG. 18). Together, the results clearly demonstrate that insulin receptor is activated in the skeletal muscle of Lepr$^{db/db}$ mice after chronic treatment with Compound #43, even though Lepr$^{db/db}$ mice are engineered to be unable to respond to insulin. In other words, the results suggest that Compound #43 can either restore insulin action, bypass insulin or both, to stimulate tyrosine phosphorylation of Insrβ to subsequently activate PI3K/Pdk1/Akt signaling in the skeletal muscle of these severe type II insulin-resistant diabetic mice.

These findings, together with the observation of enhanced glucose clearance from the bloodstream, reduced fasting levels of blood glucose, reduced levels of HbA1C and enhancement, in synergy with insulin, of glucose uptake in skeletal muscle, strongly indicate that Compound #43 may be an effective treatment for both type I and type II diabetes.

2. Compound #43 Mimics but Bypasses Insulin to Stimulate Phosphorylation of Insrβ at Y1146, Pdk1, Akt, and AS160 in Differentiated Mouse C2C12 (Skeletal Muscle) Cells To further investigate whether Compound #43 can directly activate insulin receptor signaling in the skeletal muscle, serum-starved differentiated mouse C2C12 (skeletal muscle) cells were incubated without or with Compound #43 (600 ppb), insulin (200 nM, a positive control) or both in serum-free and glucose-free DMEM media for a very short time period (i.e., 5 minutes) and 60 minutes. Then, Western blot analyses were performed to examine the protein expression levels of activated Insr (i.e., pInsrβ at Y1146) and its downstream signaling molecules including phosphorylated Pdk1, Akt and As160 in these differentiated skeletal muscle cells.

The protein expression of activated Insr in these cultured skeletal muscle cells were measured after insulin or Compound #43 treatments. As expected, treatment with insulin for 5 minutes resulted in a significant increase of pInsrβ at Y1146, but not total Insrβ, in differentiated C2C12 cells (FIG. 21A-B), indicating that these differentiated C2C12 cells rapidly respond to insulin. Further, treatment with 600 ppb of Compound #43 also resulted in a significant increase of pInsrβ at Y1146, but not total Insrβ, in these cultured skeletal muscle cells (FIG. 21A-B). Co-treatment with insulin and Compound #43 for 5 minutes tended to increase pInsrβ protein levels in these differentiated C2C12 cells (FIG. 21A-B), indicating that the stimulation of Insrβ after Compound #43 or Insulin treatment is a transient event. Indeed, prolonged treatments (60 minutes) with insulin, Compound #43 or both resulted in a decrease in pInsrβ levels (FIG. 21C-D), further indicating that the activation of Insr after insulin or Compound #43 treatment is indeed a transient event and that there exists a negative feedback to regulate Insrβ tyrosine phosphorylation in skeletal muscle cells. Regardless, the enhanced tyrosine phosphorylation of Insrβ at Y1146 observed in these cultured skeletal muscle cells after the short-time (5 minutes) treatment of Compound #43 is consistent with the activation of Insrβ in the insulin-resistant of Lepr$^{db/db}$ mice described above (FIG. 20). Since these differentiated C2C12 cells were serum-starved, cultured and treated with Compound #43 under totally serum-free conditions, the results suggest that Compound #43 can mimic but bypass insulin to directly and quickly activate Insrβ in these differentiated skeletal muscle cells.

Figure 21:
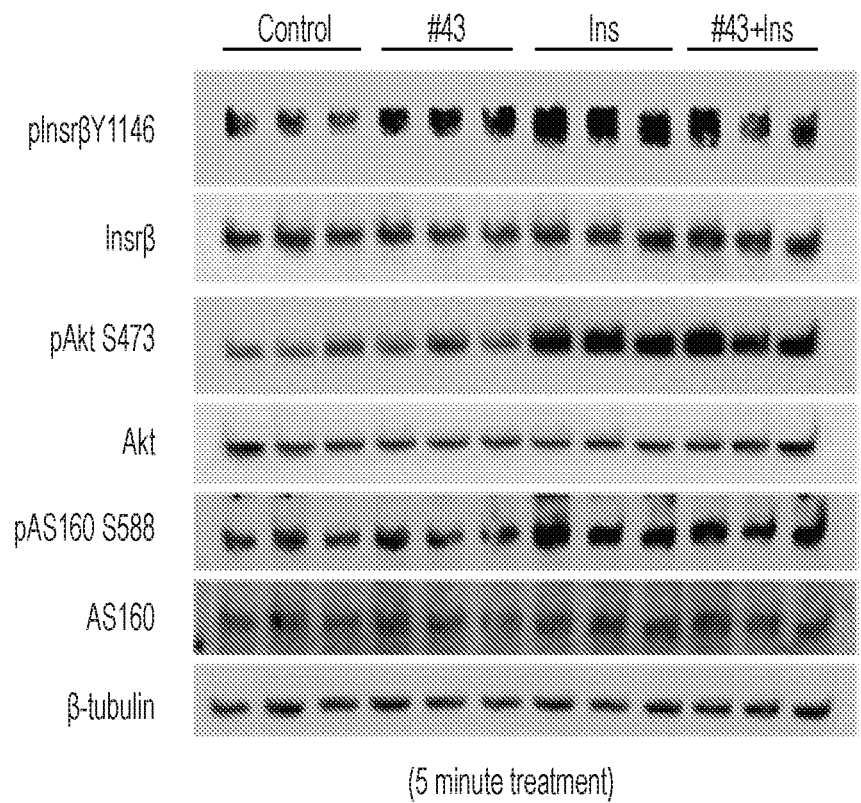
FIG. 21. Activation of Insr and stimulation of phosphorylation of Pdk1/Akt/AS160 in differentiated mouse C2C12 (skeletal muscle) cells by Compound #43. Equal number of C2C12 cells were seeded on 12-well plates (60,000 cells/well), cultured in 10% FBS DMEM media for 5 days, differentiated in 0.5% horse serum-containing DMEM media for 7 days. Completely differentiated C2C12 cells were serum-starved overnight and then treated without or with Compound #43 (600 ppb) or insulin (200 nM) in serum-free DMEM media at 37° C. for (A-B) 5 minutes or (C-D) 30 minutes, and then subjected to Western blot analysis. (A, C) Images of Western blots. (B, D) Quantitative protein levels (normalized by β-tubulin protein level in each sample). Data are presented as mean±SEM of three samples per group. *P<0.05,  P<0.01, *P<0.001 when compared to the control group (without Compound #43 treatment).
Figure 21:
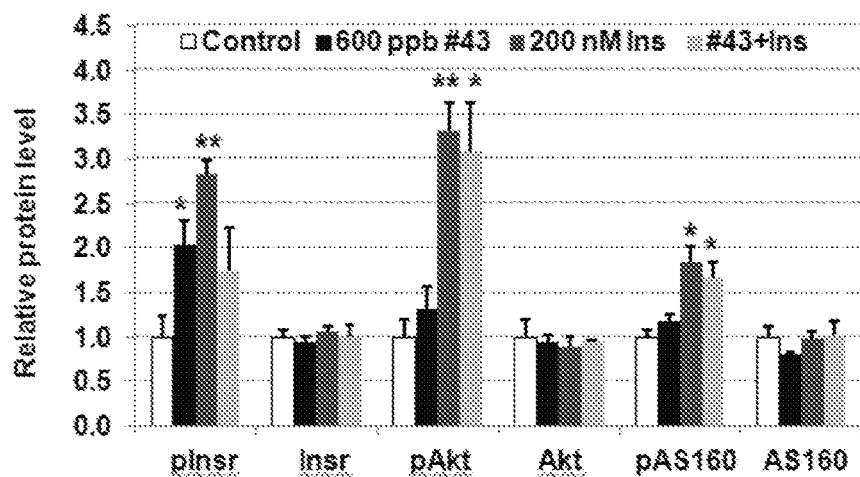
Figure 21:
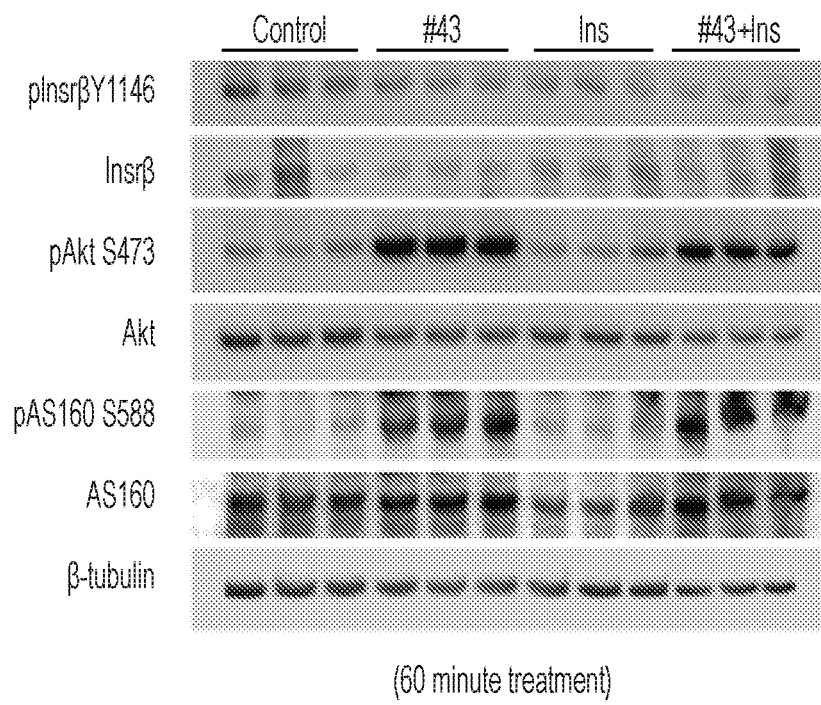
Figure 21:
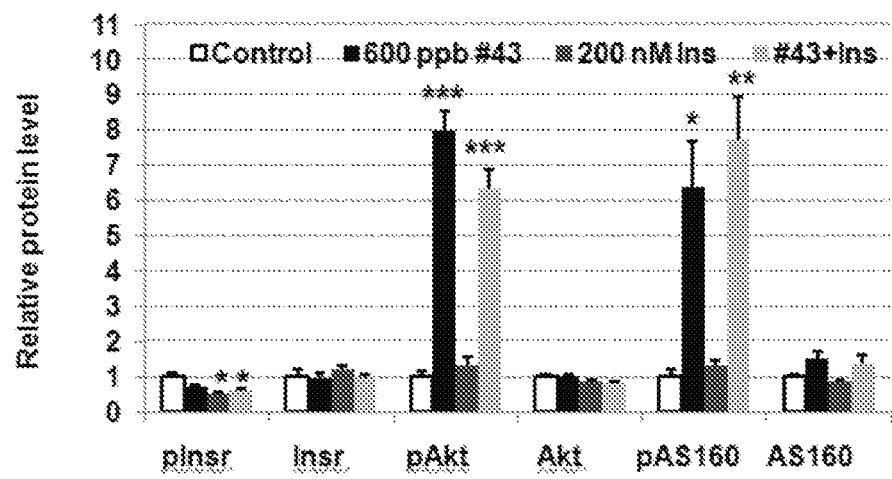

Since tyrosine phosphorylation of Insrβ will activate the PI3K/Pdk1 signaling to enhance the phosphorylation of Akt in response to insulin, it was investigated whether Compound #43 could mimic insulin to regulate Akt phosphorylation in these differentiated C2C12 skeletal muscle cells. As shown in FIG. 21A, treatment of insulin for 5 minutes resulted in a significant increase of phosphorylated Akt, but not total Akt, protein levels. However, the increased phosphorylation of Akt was not observed in these differentiated C2C12 cells after 60 minutes of insulin treatment (FIG. 21C-D). In contrast, treatment of Compound #43 for 5 minutes did not cause a significant increase of phosphorylated Akt protein levels in these C2C12 cells, while a robust increased of phosphorylated Akt proteins levels was observed in these cells after the treatment of Compound #43 for 60 minutes (FIG. 21C-D). Co-treatment of both insulin and Compound #43 resulted in a significant increase of pAkt protein levels at both tested time points (6 min and 60 min, FIG. 21). The levels of increased phosphorylation of Akt in the insulin and Compound #43 co-treated group was comparable to insulin alone at 5 minutes, while the protein levels of phosphorylated Akt at 60 minutes after the co-treatment of both insulin and Compound #43 were nearly identical to the levels after the treatment of Compound #43 alone. These results suggest that insulin can transiently activate the Insr downstream signaling molecule Akt in these skeletal muscle cells. Further, the results revealed that Compound #43 could mimic but bypass insulin to activate Akt in these cells, albeit not as quickly as insulin does. Furthermore, the results also indicate that there was no synergistic action between insulin and Compound #43 in the stimulation of Akt phosphorylation in these differentiated skeletal muscle cells. However, the results revealed that co-treatment of both Compound #43 and insulin can increase the duration of the activated Akt signaling.

As discussed above, AS160 is an Akt target substrate and is required for keeping GLUT4 proteins in the vesicles inside the skeletal muscle cells. Phosphorylation of AS160 at S588 in response to insulin/Insrβ/PI3K/Akt signaling will cause the translocation of GLUT4 proteins from cytosolic vesicles to the plasma membrane to facilitate glucose uptake. The in vivo studies revealed that Compound #43 can lower blood glucose levels and improve glucose tolerance in the insulin-resistant Lepr$^{db/db}$ mice diabetic mice (FIG. 3-8). In addition, in cultured skeletal muscles cells, increased glucose uptake was observed following Compound #43 treatment, especially after co-treatment with both insulin and Compound #43 (FIG. 19). Thus it is possible that Compound #43 can regulate GLUT4 translocation in skeletal muscle cells for glucose uptake through the phosphorylation of AS160. Therefore, the protein levels of phosphorylated AS160 at S588 were measured in the differentiated C2C12 (skeletal muscle) cells after the treatments of insulin, Compound #43, or both in serum-free media for 5 and 60 minutes.

As shown in FIG. 21A-B, treatment with insulin for 5 min did not affect protein expression of AS160, but resulted in a significant increase (about 2-fold) in the phosphorylation of AS160 at S588 in these differentiated C2C12 cells. However, no obvious increase in phosphorylated AS160 was observed after insulin treatment for 60 minutes (FIG. 21C-D). These results suggest that insulin can transiently enhance the phosphorylation of AS160 for GLUT4 translocation in skeletal muscle cells.

In contrast, treatment with Compound #43 alone for 5 minutes did not affect the protein levels of phosphorylated AS160 and total AS160 in these differentiated C2C12 cells (FIG. 21A-B). However, a robust increase (about 6-fold) in the levels of phosphorylated AS160 at S588 was observed in skeletal muscle cells after treatment with Compound #43 for 60 minutes (FIG. 21C-D). These results suggest that Compound #43 can mimic insulin, albeit not as quickly as insulin does, to induce phosphorylation of AS160 for GLUT4 translocation in these cultured skeletal muscle cells.

Co-treatment with both insulin and Compound #43 at both tested time points (5 and 60 minutes) resulted in a significant increase of phosphorylated AS160 protein levels (FIG. 21). The level of increased phosphorylation of AS160 in the co-treatment group at 5 minutes was comparable to insulin alone (FIG. 21A-B), indicating that the observed AS160 phosphorylation in the co-treatment group is mainly due to the effect of insulin at this time point. Similarly, at 60 minutes after the treatment, the protein levels of phosphorylated-AS160 in the co-treatment group were nearly identical to the levels after the treatment of Compound #43 alone (FIG. 21C-D), indicating that the observed AS160 phosphorylation in the co-treatment group at this time point is mainly due to the effect of Compound #43 alone. These results suggest that co-treatment of both Compound #43 and insulin can increase the duration of the phosphorylation of AS160 to promote GLUT4 translocation for glucose uptake in these differentiated, insulin-responsive cells.

Figure 20:
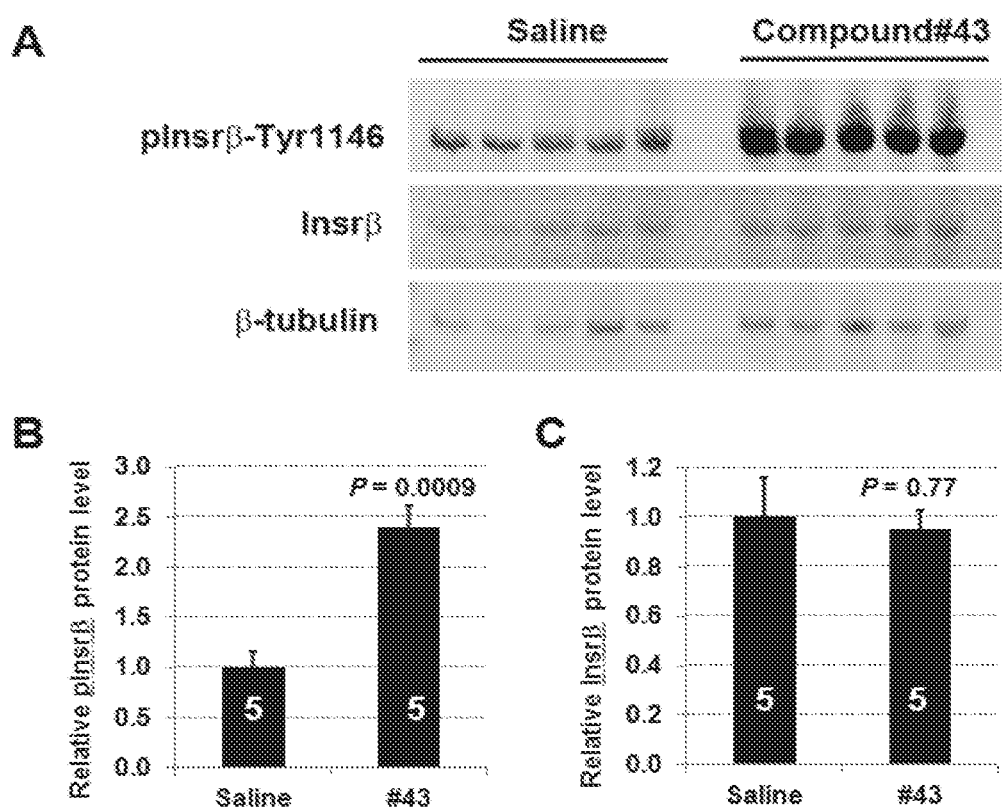
FIG. 20. Restoration of insulin receptor function (indicated by elevated phosphorylation of Insrβ at Tyrosine 1146) in the skeletal muscle of insulin-resistant Lepr$^{db/db}$ mice after chronic treatment with Compound #43. Lepr$^{db/db}$ mice at postnatal day 38 were intraperitoneally injected with saline (containing 0.2% the compound solvent DMSO) or Compound #43 at a dose of 0.136 mg of Compound #43 per kilogram body weight daily for 52 days. Western blots were performed on skeletal muscle protein extracts (100 µg protein per lane) isolated from saline or Compound #43-treated Lepr$^{db/db}$ mice. (A) Images of Western blots. (B-C) Quantitative protein levels (normalized by β-tubulin protein level in each sample). Data are presented as mean±SEM of five mice. P values were calculated by comparison of treatment values to values in the control/saline group.

Together, the results demonstrate that Compound #43 can mimic but bypass insulin to directly and quickly activate Insr (indicated by tyrosine phosphorylation of Insrβ) in differentiated C2C12 cells. This is consistent with the observed activation of Insrβ in the skeletal muscle of insulin-resistant Lepr$^{db/db}$ diabetic mice (FIG. 20). The activated Insr can then activate PI3K/Pdk1/Akt signaling in skeletal muscle (which is further supported by the in vivo studies shown in FIG. 18) to subsequently phosphorylate AS160 (a known Akt target substrate), leading to enhanced GLUT4 translocation from cytosolic vesicles to the cell membrane for glucose uptake. In fact, an increase of glucose uptake was observed in the cultured skeletal muscle cells after the treatment of Compound #43, especially after the co-treatments of both insulin and Compound #43 (FIG. 19). Enhanced glucose uptake in skeletal muscle after Compound #43 treatment can lower blood glucose levels and improve glucose tolerance in diabetic mice (FIG. 3-8). In short, these results indicate that Compound #43 can mimic but bypass insulin, to directly activate Insrβ/PI3K/Pdk1/Akt signaling to phosphorylate AS160 in skeletal muscle cells, resulting in enhanced GLUT4 translocation from cytosolic vesicles to plasma membrane to promote glucose uptake into skeletal muscle, thereby countering a key characteristic and pathology of both type 1 and type 2 diabetes.

3. Enhanced Tyrosine Phosphorylation of Insrβ in the Liver of Insulin-Resistant Lepr$^{db/db}$ Mice after Chronic Treatment with Compound #43

Figure 12:
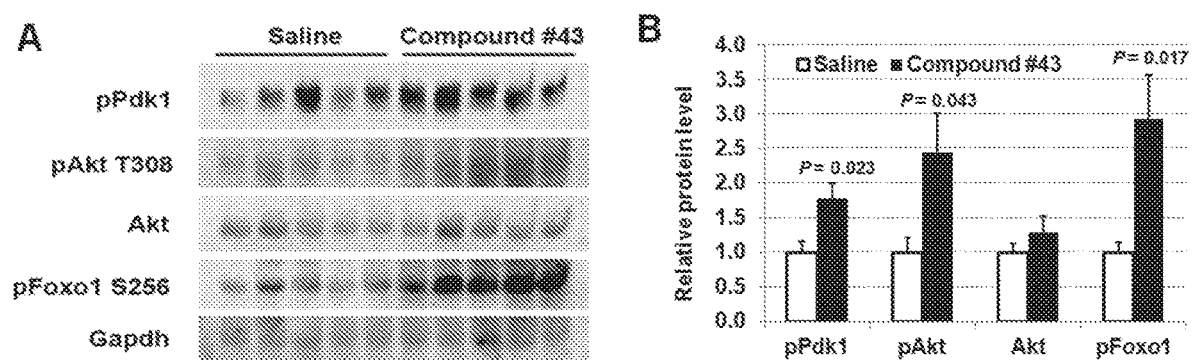
FIG. 12. Chronic treatment of Compound #43 enhanced the phosphorylation of Pdk1/Akt/Foxo1 signaling in the livers of insulin-resistant $Lepr^{db/db}$ mice by Western blot analysis. $Lepr^{db/db}$ mice at postnatal day 38 were intraperitoneally injected with saline (containing 0.2% the compound solvent DMSO) or Compound #43 at a dose of 25 μg selenium per kilogram body weight daily for 52 days. Western blots were performed on liver tissues (100 ug protein per lane) from saline or Compound #43-treated mice. (A) Western blot images. Protein levels in each sample were normalized by Gapdh level and data are presented as mean±SEM of five mice per group in (B). P value was compared to the saline group.
Figure 13:
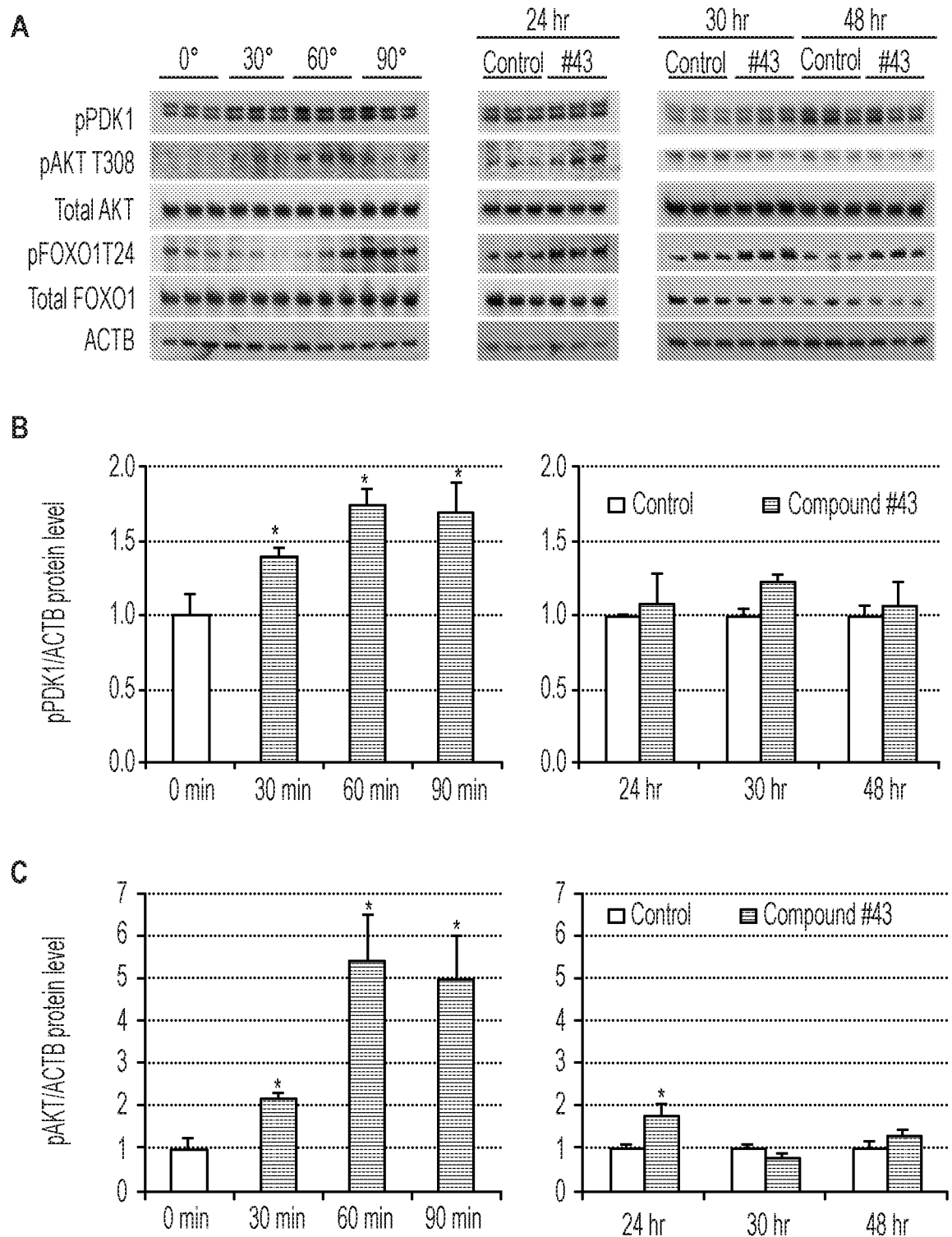
FIG. 13. Transient activation of PDK1 and AKT and subsequent inactivation of FOXO1 in human liver HepG2 cells by Compound #43. HepG2 cells were serum-starved overnight, incubated without or with Compound #43 (600 ppb) for the indicated time, and then subjected to Western blot analysis. (A) Representative Western blots. (B-F) Quantitative data of protein expressions of (B) pPDK1, (C) pAKT, (D) total AKT, (E) pFOXO1T24, and (F) total FOXO1 in Western blots are presented as mean±SEM of 3 samples. * P less than 0.05 when compared to the protein level at 0 min (right before compound treatment) or its control group at each time point.
Figure 13:
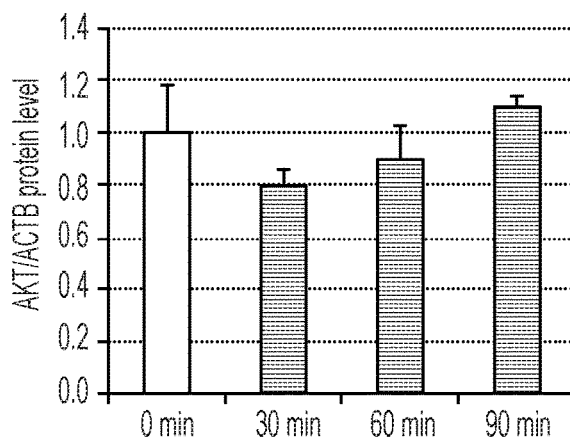
Figure 13:
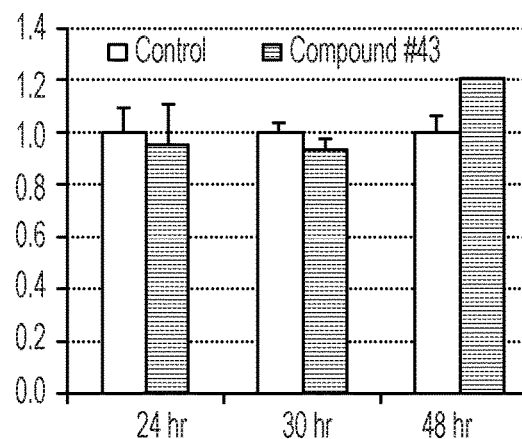
Figure 13:
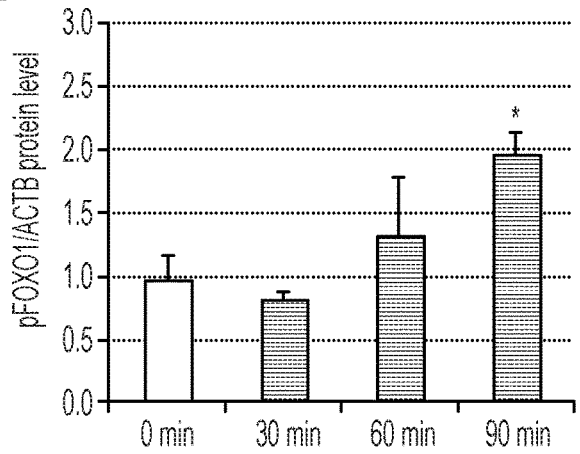
Figure 13:
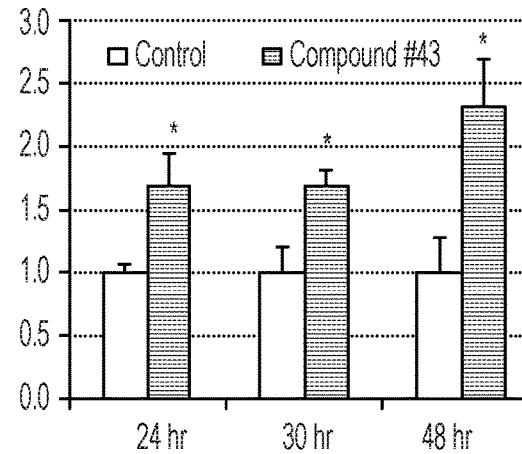
Figure 13:
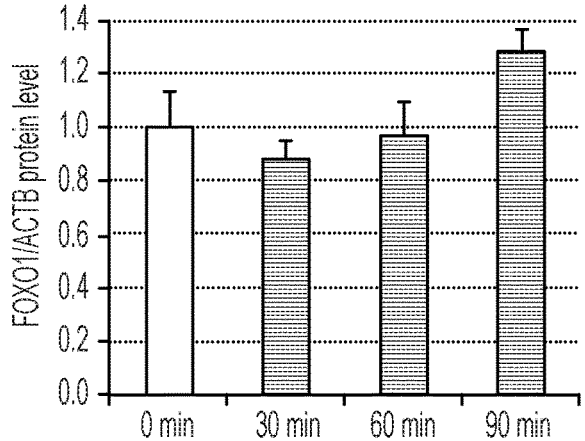
Figure 13:
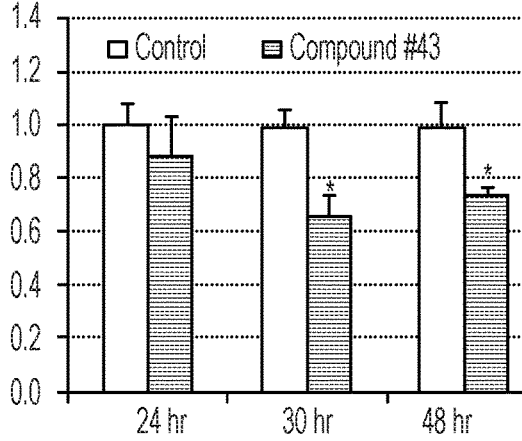
Figure 14:
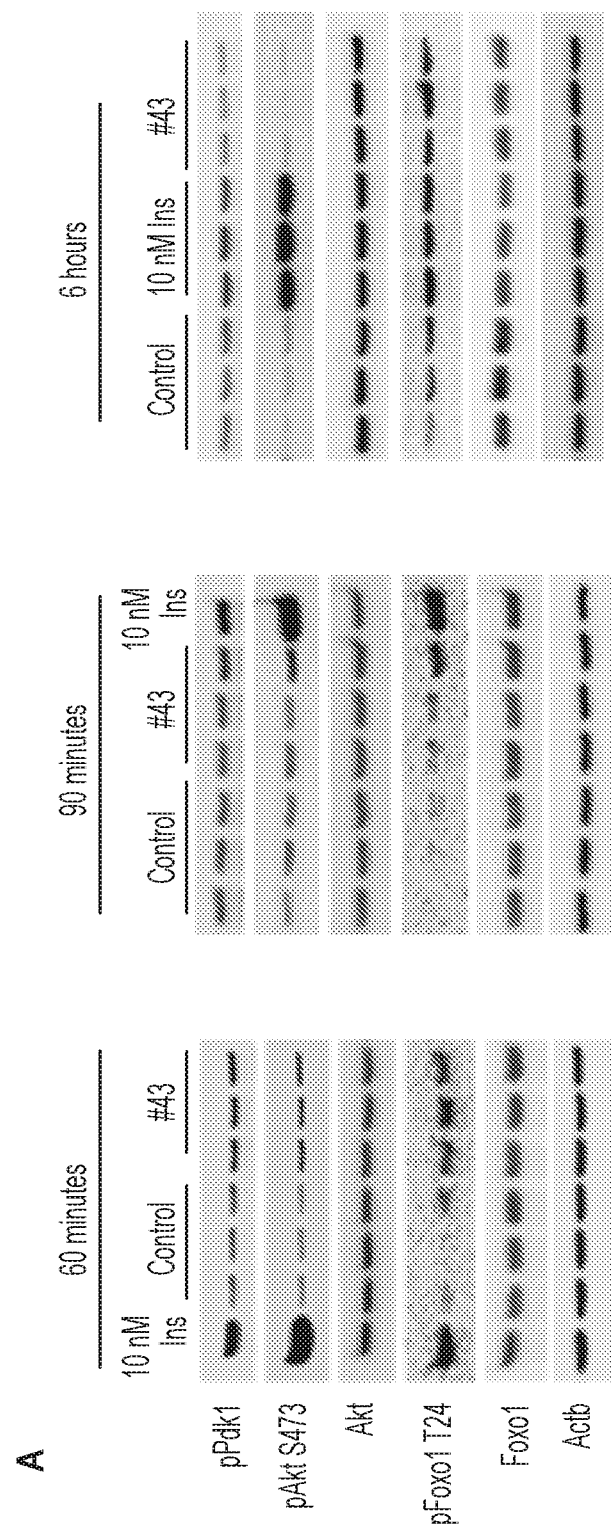
FIG. 14. Transient activation of Pdk1 and Akt and enhanced Foxo1 phosphorylation by Compound #43 in mouse liver AML-12 cells cultured under simulated diabetic condition. AML-12 cells were cultured in 10% FBS but ITS/Dex-free DMEM/F12 media for 24 hr, and then serum-starved in plain DMEM/F12 media overnight. These serum-starved AML12 cells were treated with diabetic stimuli, 8-CPT (0.1 mM) and Dex (0.5 μM), in combination without (Control) or with 10 nM insulin or Compound #43 (300 ppb) in plain DMEM/F12 media for the indicated time points, and then subjected to Western blot analysis. (A) Representative Western blots. (B-E) Quantitative data of protein expressions in Western blots are presented as mean±SEM of 3 samples. * P<0.05 when compared to the Control (no insulin/Compound #43 treatment) at each time point. Different letters in (E) represents a statistical significance (P<0.05) between those two groups.
Figure 14:
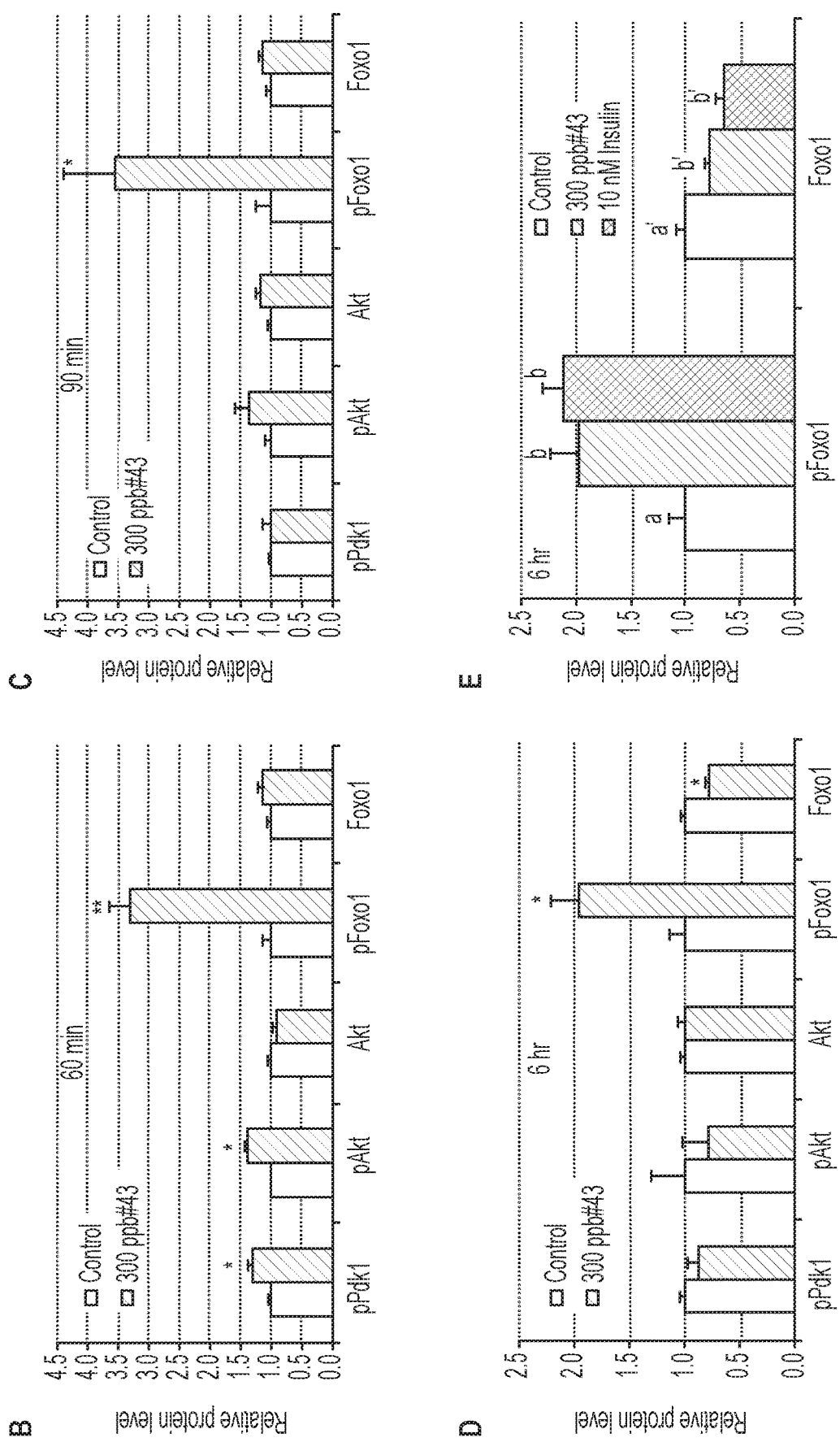

The studies described in Example 6 revealed that Compound #43 can enhance the phosphorylation of Pdk1/Akt/Foxo1 in the liver both in vivo and in vitro (FIG. 12-14). All these effects could be attributed to the activation of their upstream signaling molecule, Insr, in liver cells after Compound #43 treatment, similar to those in skeletal muscle cells described above. As discussed above, tyrosine phosphorylation of Insrβ at Y1146 and, subsequently, at Y1150/1151 reflects the first few steps of activated insulin receptor signaling following the binding of insulin to Insrα, and is the key event upstream of PI3K/Pdk1/Akt/Foxo1 signaling in the the liver. Therefore, it was investigated whether chronic treatment with Compound #43 could regulate the tyrosine phosphorylation of Insrβ in the liver of these insulin-resistant Lepr$^{db/db}$ mice.

Lepr$^{db/db}$ mice at postnatal day 38 were intraperitoneally injected with saline (containing 0.2% compound solvent DMSO) or Compound #43 at the dose of 0.136 mg of Compound #43 per kilogram body weight daily for 52 days. After the above treatments, liver samples were collected and subjected to ELISA assays of phosphor-Insrβ at Y1146 and phosphor-Insrβ at Y1150/1151 (to obtain OD450) and Western blot analysis of internal control β-tubulin. The level of phosphor-Insrβ at Y1146 or at Y1150/1151 in each sample was obtained after the OD450 in each sample was normalized by its β-tubulin protein level.

Figure 22:
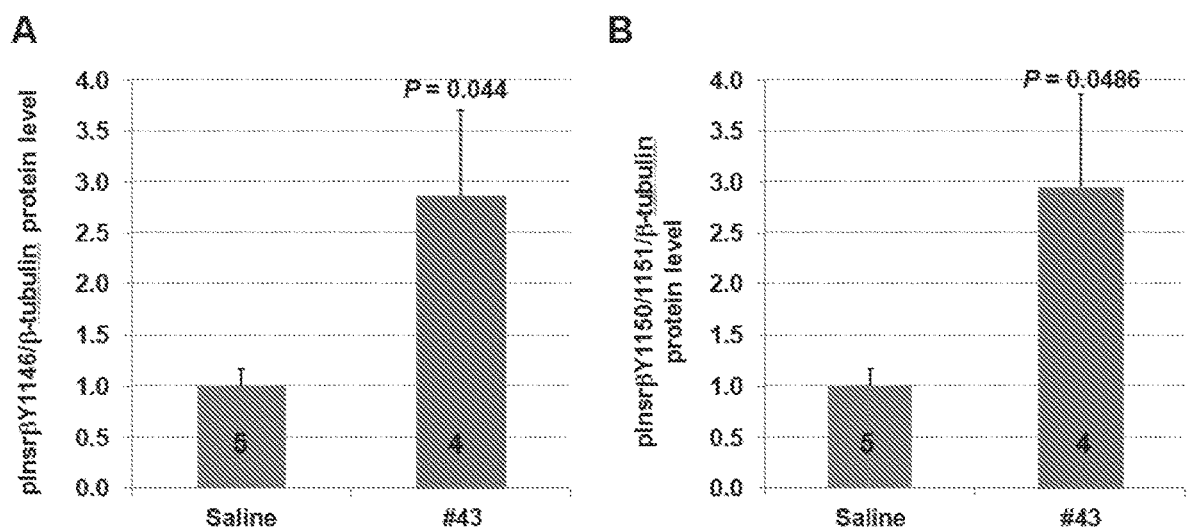
FIG. 22. Restoration of insulin receptor function (indicated by elevated tyrosine phosphorylation of Insrβ) in the livers of insulin-resistant Lepr$^{db/db}$ mice after chronic treatment with Compound #43. Lepr$^{db/db}$ mice at postnatal day 38 were intraperitoneally injected with saline (containing 0.2% the compound solvent DMSO) or Compound #43 at a dose of 0.136 mg of Compound #43 per kilogram body weight daily for 52 days. Liver protein extracts isolated from saline- or Compound #43-treated Lepr$^{db/db}$ mice were subjected to ELISA assays of (A) phospho-Insrβ at Y1146 and (B) phospho-Insrβ at Y1150/1151, and Western blot analysis of β-tubulin. (A) The protein levels of phosphor-Insrβ at Y1146 (normalized by β-tubulin protein level in each sample). (B) The protein levels of phospho-Insrβ at Y1150/1151 (normalized by β-tubulin protein level in each sample). Data are presented as mean±SEM of the indicated number of mice. P values were calculated by comparison of treatment values to values in the saline group.

As shown in FIG. 22A, the protein levels of phosphorylated Insrβ at Tyrosine 1146 were significantly increased (about a 2.9 fold-increase) in the liver of Lepr$^{db/db}$ mice after treatment with Compound #43, when compared to saline-treated mice. Similarly, the protein levels of phosphorylated Insrβ at Tyrosine 1150/1151 were also significantly increased (about a 2.95 fold-increase) in the liver of Lepr$^{db/db}$ mice after chronic treatment with Compound #43, when compared to saline-treated mice (FIG. 22B). These results are consistent with the observation of increased phosphorylation of Pdk1 and Akt, the key insulin signaling molecules downstream of Insr in the livers of Compound #43-treated Lepr$^{db/db}$ mice (FIG. 12). Together, the results clearly demonstrate that insulin receptor is activated in the liver of Lepr$^{db/db}$ mice after chronic treatment with Compound #43, even though Lepr$^{db/db}$ mice are engineered to be unable to respond to insulin. In other words, the results suggest that Compound #43 can either restore insulin action, bypass insulin or both, to stimulate tyrosine phosphorylation of Insrβ to subsequently activate PI3K/Pdk1/Akt signaling in the liver of these severe type II insulin-resistant diabetic mice.

Figure 23:
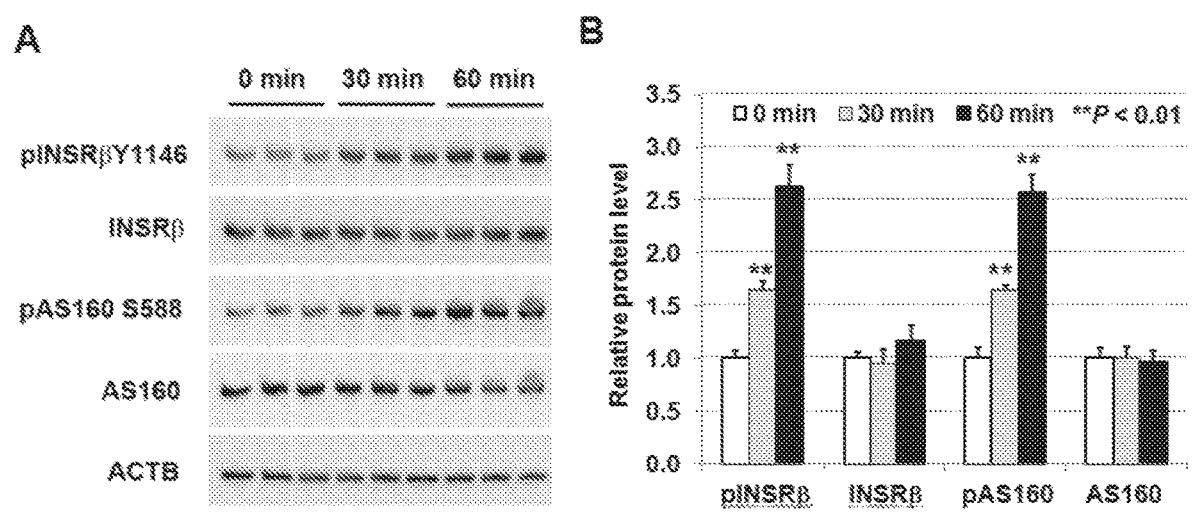
FIG. 23. Activation of INSR and stimulation of AS160 phosphorylation in human liver HepG2 cells by Compound #43. HepG2 cells were seeded on 6-well plates (7×10$^5$ cells/well), cultured in 10% FBS EMEM media for 30 hr, and then serum-starved overnight. These serum-starved HepG2 cells were then treated with Compound #43 (600 ppb) at 37° C. for 30 and 60 minutes (min), and then subjected to Western blot analysis. (A) Images of Western blots. (B) Quantitative protein levels (normalized by ACTB protein level in each sample). Data are presented as mean±SEM of three samples per group. ** P<0.01, when compared to the control group (0 min group, before Compound #43 treatment).

4. Compound #43 Mimics but Bypasses Insulin to Stimulate Phosphorylation of Insrβ at Y1146 and AS160 at S588 in Human Liver HepG2 Cells To further investigate whether Compound #43 can mimic but bypass insulin to directly activate insulin receptor in the liver cells, human liver HepG2 cells were serum-starved overnight and then were incubated with Compound #43 (600 ppb) in serum-free and glucose-free DMEM media for 30 and 60 minutes. Western blot analyses were performed to examine the protein expression levels of activated INSR (i.e., pINSRβ at Y1146) in these human liver cells. As shown in FIG. 23, treatment with 600 ppb of Compound #43 for both 30 and 60 minutes resulted in a significant increase of phosphorylated INSRβ at Y1146, but not total INSRβ, in these cultured liver cells. These results are consistent with the increased phosphorylation of INSR downstream signaling molecules, PDK1 and AKT, in HepG2 cells after the treatment of Compound #43 for the same time periods (FIG. 13). Since these liver cells were serum-starved, and treatment of Compound #43 was performed under the totally serum-free condition, the results suggest that Compound #43 can mimic but bypass insulin to directly stimulate tyrosine phosphorylation of INSRβ, leading to the activation of PI3K/PI3K/AKT to inactivate FOXO1 for the inhibition of G6PC expression for glucose production, and the stimulation of the expression of GLUT4 for glucose uptake in the liver cells.

Beside FOXO1, AS160 is another AKT target substrate that plays a critical role for glucose translocation from cellular vesicles to the plasma membrane in insulin-target tissues such as adipose cells and skeletal muscle. The in vivo and in vitro studies showed that Compound #43 can lower blood glucose levels and improve glucose tolerance in diabetic mice (FIG. 3-8) and can enhance glucose uptake in cultured AML-12 liver cells (FIG. 17), indicating that enhanced glucose uptake in the liver could be one of the mechanisms of Compound #43 in lowering blood glucose levels and improving glucose tolerance against type I and II diabetes. The enhanced glucose uptake elicited after Compound #43 treatment may well result from the enhanced GLUT4 expression (indicated by FIGS. 15-16), the potential enhanced GLUT4 translocation, or both, to stimulate glucose uptake into liver cells. To address the latter scenario, phosphorylated AS160 (an AKT targeted substrate) protein levels were measured in Compound #43-treated HepG2 cells.

As shown in FIG. 23, treatment with 600 ppb of Compound #43 for both 30 and 60 minutes resulted in a significant increase of phosphorylated AS160 at S588, but not total AS160 protein levels, in these cultured human liver cells. These results are consistent with the increased phosphorylation of PDK1 and AKT, two critical signaling molecules upstream of AS160, in HepG2 cells after treatment with Compound #43 for the same time periods (FIG. 13). As phosphorylation of AS160 can enhance the GLUT4 translocation from cellular vesicles to cell membrane for glucose uptake, the results suggest that Compound #43 can mimic but bypass insulin to stimulate GLUT4 translocation from cytosolic vesicle to plasma membrane for glucose uptake in human liver cells. In support of this, it will be recalled that enhanced glucose uptake was observed in cultured AML-12 liver cells after treatment of Compound #43 for 1.5 hr (FIG. 17). Thus in liver cells, Compound #43 will not only stimulate GLUT4 expression mediated through Insr/PI3k/Pdk1/Akt/Foxo1 signaling (indicated by FIGS. 12-17), but also enhanced GLUT4 translocation from cytosolic vesicles to plasma membrane mediated through Insr/PI3K/Pdk1/Akt/AS160 (indicated by FIGS. 12-17, 23), thus enhancing glucose uptake.

In summary, all the above studies reveal that Compound #43 can restore insulin receptor function (as indicated by the enhanced tyrosine phosphorylation of Insrβ) in both skeletal muscles and liver of the insulin-resistant diabetic $Lepr^{db/db}$ mice. The in vitro studies further demonstrate that Compound #43 can closely mimic insulin to activate insulin receptor in both skeletal muscle cells and human liver cells. In addition, the results demonstrate that Compound #43, like insulin, can activate Pdk1/Akt signaling to induce the phosphorylation of AS160 (an AKT target substrate) in both cultured skeletal muscle cells and human liver cells. Enhanced phosphorylation of AS160 promotes GLUT4 translocation from cytosolic vesicles to plasma membrane to enhance glucose uptake in both the liver and skeletal muscle cells resulting in lower blood glucose levels and improved glucose tolerance in diabetic situations.

It should be stressed that these two tissues, liver and skeletal muscle, are by far the most critical in the development and pathogenesis of type II diabetes. Compound #43, through its ability to restore the insulin signaling cascade in these tissues, could be of immense therapeutic value in the treatment of type II diabetes.

Furthermore, because Compound #43 can function as an insulin-mimetic in insulin-responsive cells to which no insulin has been added, there exists a strong possibility that it could be an effective treatment for type I diabetes also.

Example 9: Chronic Treatments of Compound #43 Resulted in a Decrease of Serum Insulin and Alanine Aminotransferase (ALT) Levels but not Serum Creatinine Levels in Insulin-Resistant Diabetic Db/Db Mice Materials and Methods
Compound Compound #43 was synthesized in the Chemistry Laboratory of Alltech, Inc. The purities of all tested compounds were verified to be ≥99%, as determined by HPLC.

Animals 5-week-old male diabetic spontaneous mutation (leptin receptor mutation) $Lepr^{db/db}$ mice (C57BL/6J strain) were purchased from The Jackson Laboratory (Bar Harbor, Me.), and housed in a pathogen-free vivarium with free access to chow and water. 3-month-old wild-type (non-diabetic) C57 mice were also purchased from the Jackson Laboratory.

Chronic Treatments with Compound #43

Male $Lepr^{db/db}$ mice at 38 days of age were intraperitoneally (ip) injected daily with physiological saline (0.09% NaCl) containing 0.2% DMSO, and Compound #43 (0.136 mg per kilogram body weight, diluted in sterile physiological saline) for 52 days. Sera from 3-month-old wild-type (non-diabetic) C57 mice were also collected. After the treatments, these serum samples were collected and subjected to insulin, ALT and creatinine assays.

Serum Insulin, ALT and Creatinine Assays

The serum levels of insulin, ALT and creatinine were determined using Themo-Fisher Scientific's Insulin Mouse ELISA kit (Cat #EMINS), Sigma's ALT Activity Assay kit (Cat #MAK052), and Abcam's Creatinine Assay kit (Cat #Ab65340) according to the manufacturer's protocol, respectively.

Statistical Analysis

Where applicable, a Student's t-test was used to determine the statistical significance of difference between saline- and compound-treated groups, with a P value less than 0.05 being deemed significant. Data are presented as mean±SEM of the indicated numbers of mice in the figures.

Results and Discussion

Figure 24:
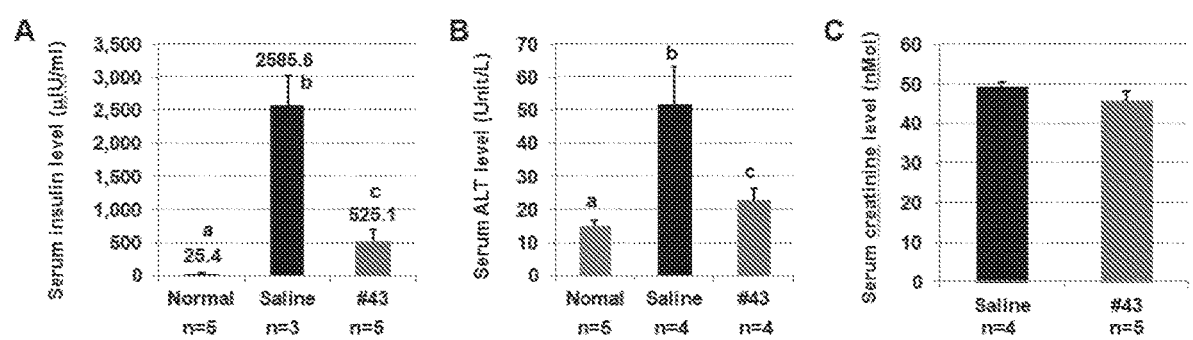
FIG. 24. Chronic treatment of Compound #43 resulted in a decrease of serum insulin and alanine aminotransferase (ALT), but not creatinine, levels in Lepr$^{db/db}$ mice. Male Lepr$^{db/db}$ mice at 38 days of age were intraperitoneally (ip) injected daily with physiological saline (0.09% NaCl) containing 0.2% DMSO, or Compound #43 at a dose of 0.136 mg per kilogram body weight, diluted in sterile physiological saline) for 52 days. Sera from 3-month-old wild-type (non-diabetic) C57 mice were also collected. These serum samples were collected and subjected to (A) insulin, (B) ALT and (C) creatinine assays. Numbers on the top of each column in (A) are the mean values of insulin levels. Different letters in the bars represents a statistical significance between those two groups.

As shown in FIG. 24A, $Lepr^{db/db}$ mice displayed hyperinsulinemia with the insulin levels about 2586 µIU/ml (about 100 times higher than non-diabetic wild-type mice). However compound #43 treatment resulted in dramatically decrease of serum insulin levels (about 80% decrease), even though its level was still higher than non-diabetic wild-type mice (FIG. 24A). These results suggest that compound #43 has the potential to treatment hyperinsulinemia in diabetic patients.

The alanine aminotransferase (ALT) test is typically used to detect liver injury. As shown in FIG. 24B, serum ALT levels in saline-treated $Lepr^{db/db}$ mice were significantly higher than non-diabetic mice. However, compound #43 treatment resulted in a significant decrease of serum ALT levels. These results suggested that the chronic treatment of compound #43 (treated daily for 52 days) did not display liver toxicity; instead, it may have a protective effect against liver damage.

The blood creatinine test is widely used to assess kidney function and elevated creatinine level signifies impaired kidney function or kidney disease. As shown in FIG. 24C, there was no significant change in serum creatinine levels in $Lepr^{db/db}$ mice after compound #43 treatment. These results suggest that the chronic treatment of compound #43 (treated daily for 52 days) likely do not have toxic effect on the kidney function.

Together the above results suggest the potential use of compound #43 against hyperinsulimemia in diabetic subjects. In addition, the above results also suggest that Compound #43 have little or no toxic effect on the liver and kidney functions. Instead, Compound #43 may display some protective effect against liver damage.

Figure 25:
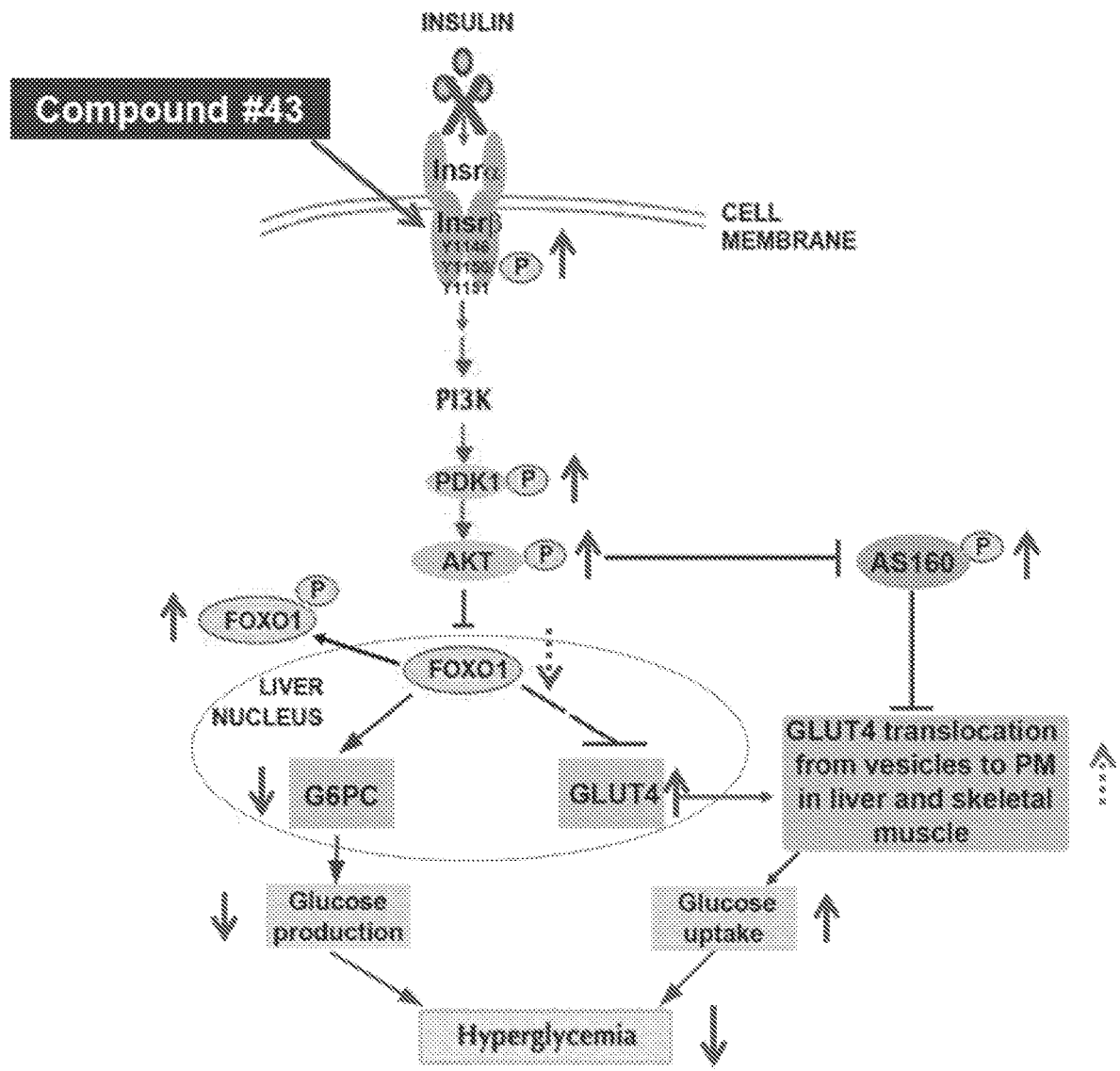
FIG. 25. Mode of action of Compound #43 against type I and II diabetes.

Conclusion (Mode of Action; FIG. 25)

The experimental results in this disclosure are shown by solid red arrows while the expected results (based on published literature) are shown by dashed arrows. Compound #43 can mimic but bypass insulin to quickly induce tyrosine phosphorylation of insulin receptor subunit on the inner surface of the cell membrane, thus precluding the need for insulin to bind and activate insulin receptor α at the cell surface. This results in the activation of the PI3K/PDK1/AKT signaling cascade in both liver and skeletal muscle. In other words, normal insulin signaling can be restored without a need for insulin or active cell surface insulin receptor to be present. In liver cells, activation of AKT causes a robust increase in FOXO1 phosphorylation, resulting in a significant decrease in the expression of the FOXO1-direct target gene G6PC; this leads to the inhibition of glucose production in the hepatocytes of diabetic subjects. In addition, expression of the FOXO1-indirect target gene GLUT4 and the phosphorylation of the AKT target substrate AS160 (TBC1D4), which is key for GLUT4 translocation from cytosolic vesicles to the plasma membrane, are enhanced in liver cells after Compound #43 treatment, resulting in more GLUT4 transport proteins in the liver cell membrane and improved glucose uptake from the bloodstream. All of this points to improved glucose tolerance in type I and II diabetic subjects. In skeletal muscle cells, Compound #43 can also mimic, yet bypass, insulin to activate INSRβ/PDK1/AKT signaling, leading to phosphorylation of AS160 (TBCID4). Again, this results in enhanced translocation of GLUT4 from cytosolic vesicles to the plasma membrane to facilitate glucose uptake into skeletal muscle cells, eventually leading to a significant decrease in blood glucose and a dramatic improvement of glucose tolerance in both type I and II diabetic subjects. As shown, Compound #43 can potentiate insulin action by the inhibition of G6PC expression in liver cells. Uncontrolled glucose production by liver—a process driven by G6PC expression—is both a key feature and a key problem in type 2 diabetes. Suppression of glucose production in diabetic liver is a key mechanism of action for the most widely used class of anti-diabetic drugs, the biguanides, e.g., metformin. The ability of compound #43 to block this process makes it potentially very valuable in the treatment of type 2 diabetes. Furthermore, Compound #43 can restore insulin receptor function in the skeletal muscle of insulin-resistant diabetic mice, and can potentiate insulin action to stimulate glucose uptake in cultured skeletal muscle cells. Together, these results indicate great potential for the use of Compound #43 against type I and II diabetes in humans.

Example 10: Direct Activation of Insulin Receptor Proteins by Compound #43 in a Cell-Free System Materials and Methods
Compounds
Compound #43 and its sulfur analog, Compound #68, were synthesized in the Chemistry Laboratory of Alltech, Inc. The purities of these tested compounds were verified to be ≥99%, as determined by HPLC.
In Vitro Phosphorylation of Insulin Receptor (Insr), and the Detection of Activated Insr (Indicated by Phosphorylated Tyrosine Residues at 1146, 1150 and 1151 of the Insr Beta Subunit) by Western Blot Analysis
In vitro phosphorylation of Insr was performed according to Sigma's protocol with the following modifications. In brief, 10 μl of native insulin receptor solution containing 0.8 μl of original native INSR stock solution (Sigma, Catalog #I9266; diluted in enzyme dilution buffer containing 50 mM HEPES, pH 7.6, 150 mM NaCl and 0.1% Triton X-100) were incubated with equal volume of solutions containing insulin (Sigma), DMSO (Compound #43 solvent), Compound #43 or Compound #68 (diluted in 50 mM HEPES, pH 7.6 and 100 μg/ml bovine serum albumin) on ice for 30 min. Then 20 μl of 2× kinase buffer containing 0.2 mM ATP, 50 mM HEPES, pH 7.6, 50 mM $MgCl_2$ and 4 mM $MnCl_2$ were added to the above reactions, mixed and incubated on ice for 45 minutes.
Five microliters of the above reactions were immediately subjected to Western blot analysis using specific antibodies against phosphorylated tyrosine residues at 1146, 1150 and 1151 of Insrβ proteins (Cell Signaling Inc.). Protein band density was determined using the NIH Image J software.

Figure 26:
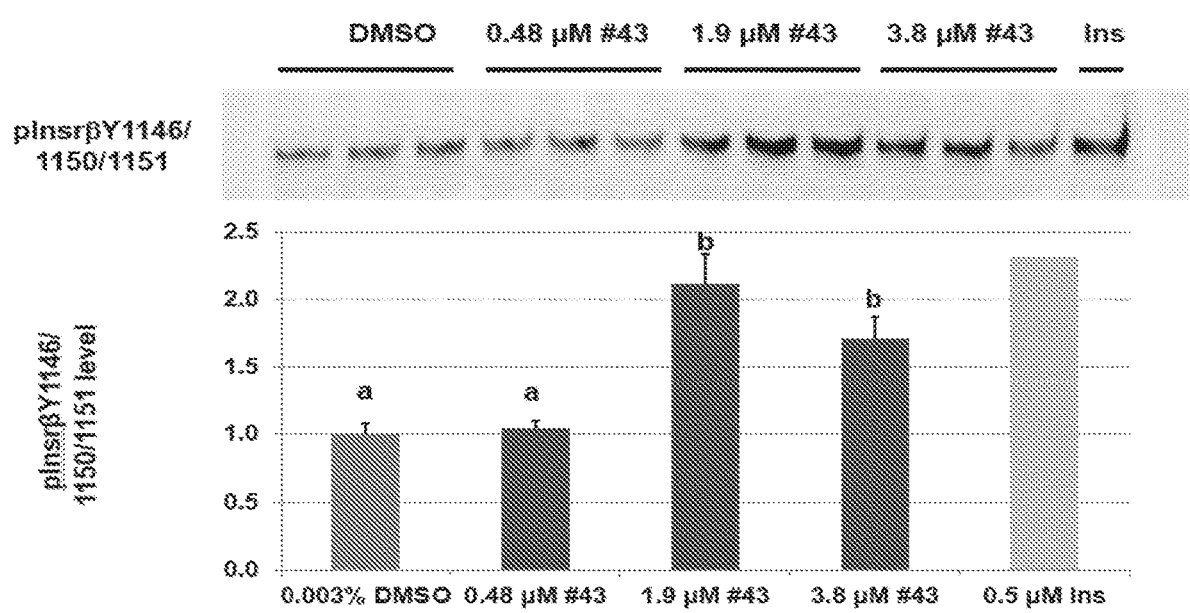
FIG. 26. Direct activation of insulin receptor by Compound #43 and insulin in a cell-free system. Equal amounts of native insulin receptor proteins, containing both alpha and beta subunits were incubated with 0.003% DMSO (Compound #43 solvent), Compound #43 or insulin (Ins, 0.5 µM) in the presence of ATP, and then subjected to Western blot analysis to detect phosphorylated Insrβ (activated Insr) at Y1146, 1150 and 1151. Different alphabetic letter in the bar graph denotes statistically significant changes between those groups.
Figure 27:
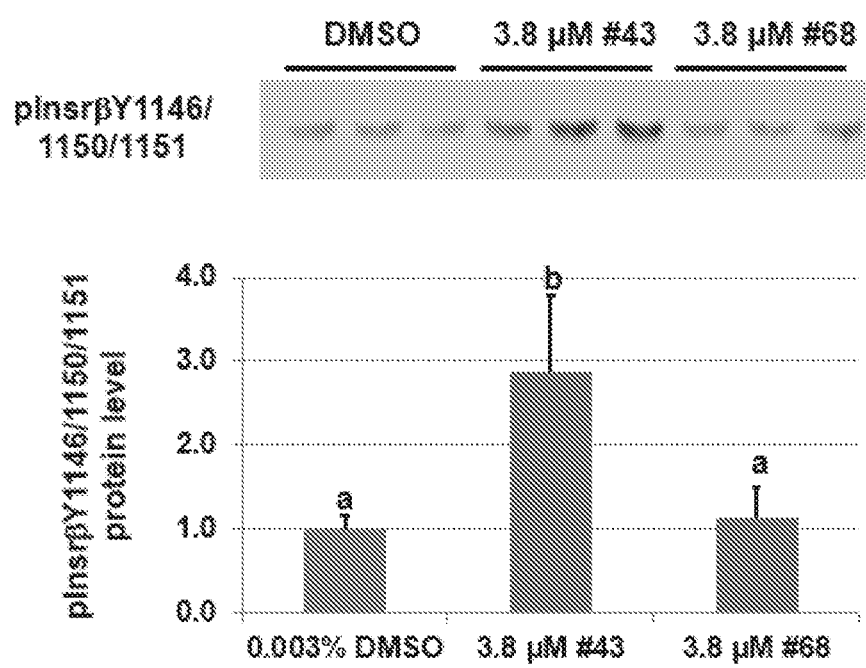
FIG. 27. Compound #68 was less effective than Compound #43 in the activation of insulin receptor in the cell-free system. Equal amounts of native insulin receptor were incubated with 0.003% DMSO (Compound #43 solvent), Compound #43 or Compound #68 in the presence of ATP. The activated Insr proteins were detected by Western blot analysis of phosphorylated Insrβ at Y1146, 1150 and 1151. Different alphabetic letters in the bar graph mean statistically significant changes occurred between those groups.

Statistical Analysis
Where applicable, a Student's t-test was used to determine the statistical significance of difference among treatment groups, with a P value less than 0.05 being deemed significant.
Results:
1. Native Insulin Receptor Protein Purified from Rat Liver Tissues was Activated in the In Vitro Cell-Free System by Compound #43 and Insulin
Studies in cultured liver and differentiated skeletal muscle cells, as well as in T2D diabetic mice, revealed that Compound #43 can activate insulin receptor both in vitro and in vivo. To investigate whether Compound #43 has a direct effect on the activation of Insr, in vitro cell-free phosphorylation assays of native insulin receptor proteins (purified from rat liver tissues) were performed. Activated Insr was detected using specific antibodies against phosphorylated Insrβ at tyrosine residues 1146, 1150 and 1151. As expected, insulin treatment was able to induce the phosphorylation of Insrβ at Y1146/1150/1151, in this cell-free in vitro system (FIG. 26). Importantly, Compound #43, at doses of 1.9 and 3.8 was also able to significantly enhance the phosphorylation of Insrβ at Y1146/1150/1151 with the elevated phosphorylation levels being directly comparable to 0.5 μM insulin (FIG. 26). These results confirm that Compound #43 can faithfully mimic insulin to directly activate the insulin receptor, providing further molecular evidence that Compound #43 has the potential to replace insulin against diabetes, including type I diabetes.
2. Compound #68, the Sulfur Analog of Compound #43, is Far Less Effective than Compound #43 in the Activation of Insr in the Cell-Free System
Studies in cultured liver cells and type 2 diabetic (T2D) $Lepr^{db/db}$ mice showed that Compound #68, the sulfur analog of Compound #43, was less effective than Compound #43 in the inhibition of glucose production in vitro (FIG. 1) and the attenuation of hyperglycemia in T2D mice (FIG. 4). To investigate whether there is a differential effect between Compound #43 and Compound #68 in the activation of Insr in the cell-free system, equal amounts of native insulin receptor proteins were incubated with the same molar concentration (3.8 μM) of Compound #43 or Compound #68, and then subjected to the in vitro phosphorylation assay. As shown in FIG. 27, Compound #43 but not Compound #68 at the tested dose was able to activate Insr. These studies suggest that Compound #68 was less effective at the tested dose than Compound #43 in the activation of Insr, which may explain the lower efficacy of Compound #68 in the inhibition of liver glucose production (FIG. 1) and against hyperglycemia in T2D mice (FIG. 4).

Example 11: Deceased Blood Glucose Levels in Streptozotocin (STZ)-Induced Type 1 Diabetic (T1D) Mice after Acute Treatment of Compound #43

Materials and Methods
Compounds
Streptozotocin (STZ) was purchased from Sigma. Compound #43 was synthesized in the Chemistry Laboratory of Alltech, Inc. The purity of Compound #43 was verified to be ≥99%, as determined by HPLC.
Type 1 Diabetic (T1D) Mouse Model and Effects of Compound #43 on Blood Glucose Levels in these T1D Mice
Five-week-old C57/BL6 male mice were intraperitoneally injected with streptozotocin (STZ, 55 mg/kg mouse body weigh) daily for 5 days, and then housed in the vivarium for another 14 days for recovery. Blood glucose levels of these mice were measured using a glucometer. Those animals with a blood glucose level higher than 500 mg/dL were considered to be type I diabetic (T1D). These T1D mice with unfasted blood glucose levels between 500-550 mg/dL were fasted overnight and injected intraperitoneally with Compound #43 at a dose of 5.4 mg/kg body weight or physiological saline containing 2% DMSO (Compound #43 stock solvent). At 1, 2 and 3 hours post-injection, blood glucose levels in these mice were measured using the glucometer.

Statistical Analysis

A Student's t-test was used to determine the statistical significance of difference between control (DMSO) and Compound #43 group at each time point. A P value less than 0.05 denotes statistically significant differences between those two groups.

Results

Figure 28:
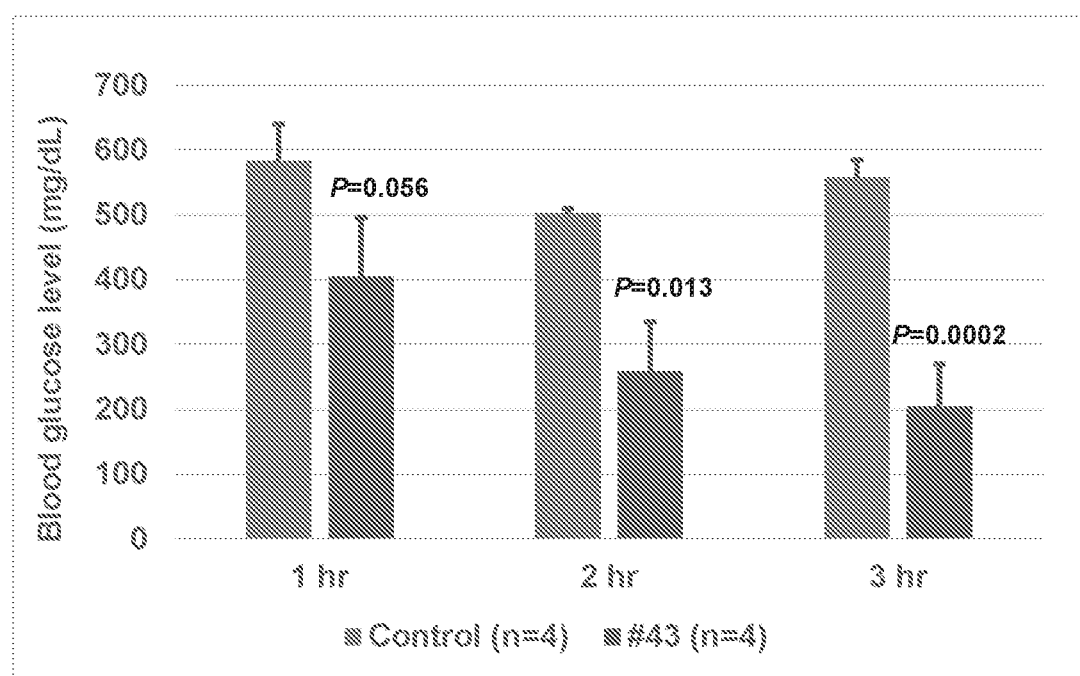
FIG. 28. Reduced blood glucose levels in STZ-induced T1D mice after acute treatment of Compound #43. STZ-induced T1D mice with unfasted blood glucose levels between 500-550 mg/dL were fasted overnight, and injected intraperitoneally with Compound #43 at a dose of 5.4 mg/kg body weight or with physiological saline containing 2% DMSO (Compound #43 stock solvent, referred to as Control group) for 1, 2 and 3 hours. Mice were then subjected to blood glucose measurement. P values were derived by comparing Compound #43 treatments to the control/saline group at each time point.

To investigate the potential of Compound #43 against hyperglycermia in T1D mice, STZ-induced T1D mice with blood glucose levels between 500-550 mg/dL were fasted overnight, intraperitoneally injected with physiological saline containing DMSO or Compound #43 (5.4 mg/kilogram body weight) for 1, 2 and 3 hours, and then subjected to the measurement of blood glucose levels. As shown in FIG. 28, there was no obvious change in the blood glucose levels in control mice (with the injection of DMSO-containing saline) during the 3-hour time period. However, a trend of decreased blood glucose levels was observed in these T1D mice after the treatment with Compound #43 for 1 hour (FIG. 28). More importantly, a significant decrease in blood glucose levels was observed in these T1D mice after Compound #43 treatment for both 2 and 3 hours (FIG. 28). Together, these results confirm that Compound #43 attenuates hyperglycemia in T1D mice.

While some embodiments are illustrated in the examples, it is apparent that they may be altered to provide other embodiments of the instant disclosure. Therefore, it will be appreciated that the scope of the invention is to be defined by the appended claims rather than by the specific embodiments that have been represented by way of example.

The invention claimed is:

1. A method for treating an insulin resistance disorder comprising administering a therapeutically effective amount of a compound of formula (2):

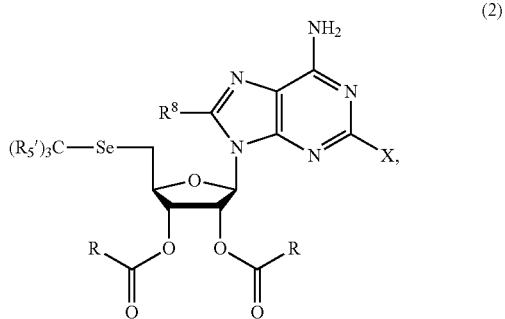

(2)

or a pharmaceutically acceptable salt, stereoisomer, or isotopic, conformational, or geometric isomer thereof, wherein:
$R^8$ is H or halogen;
X is H or halogen;
each $R_5'$ is independently H or halogen; and
each R is independently $C_{1-6}$alkyl, each of which, independently, may optionally be substituted 1-3 times by halogen.

2. The method of claim 1, wherein the insulin resistance disorder is diabetes, obesity, metabolic syndrome, insulin-resistance syndromes, syndrome X, insulin resistance, high blood pressure, hypertension, high blood cholesterol, hyperlipidemia, dyslipidemia, an atherosclerotic disease, hyperglycemia, hyperinsulinemia, hyperproinsulinemia, impaired glucose tolerance, delayed insulin release, a diabetic complication, a cancer, a disorder associated with pregnancy or poor female reproductive health, lipodystrophy, a cholesterol related disorder, osteoarthritis, osteoporosis, or a type II diabetes related vascular disorder.

3. The method of claim 2, wherein the insulin resistance disorder is stroke, coronary artery disease, myocardial infarction, coronary heart disease, angina pectoris, congestive heart failure, cognitive functions in dementia, retinopathy, neuropathy, nephropathy, glomerulonephritis, glomerulosclerosis, nephrotic syndrome, hypertensive nephrosclerosis, endometrial cancer, breast cancer, prostate cancer, colon cancer, menstrual irregularities, infertility, irregular ovulation, polycystic ovarian syndrome (PCOS), gallstones, cholescystitis, cholelithiasis, gout, obstructive sleep apnea, or respiratory problems.

4. The method of claim 1, wherein the compound is of formula (2'):

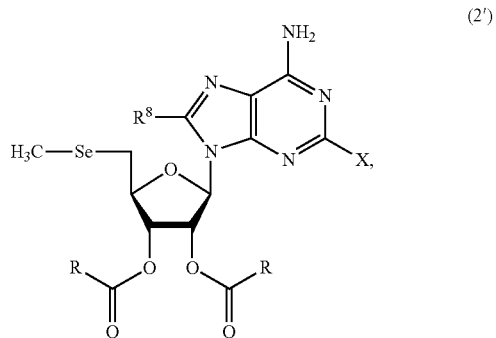

(2')

or a pharmaceutically acceptable salt, stereoisomer, or isotopic, conformational, or geometric isomer thereof.

5. The method of claim 1, wherein $R^8$ is H.

6. The method of claim 1, wherein X is H.

7. The method of claim 1, wherein each R is independently $C_{1-3}$alkyl, each of which, independently, may optionally be substituted 1-3 times by halogen.

8. The method of claim 1, wherein each R is independently unsubstituted $C_{1-3}$alkyl.

9. The method of claim 1, wherein the compound is of the formula:

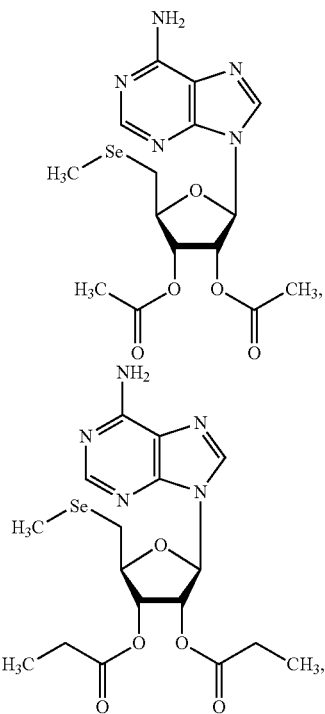

-continued

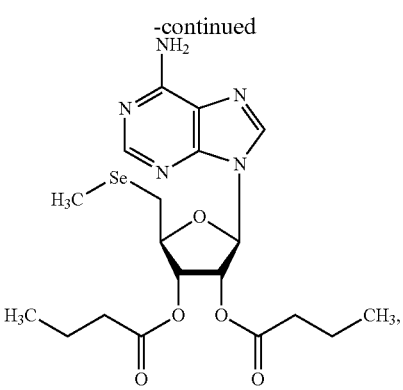

or a pharmaceutically acceptable salt, stereoisomer, or isotopic, conformational, or geometric isomer thereof.

10. The method of claim 9, wherein the compound is of the formula:

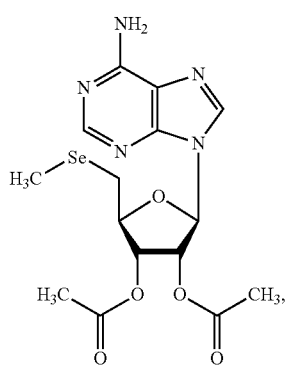

or a pharmaceutically acceptable salt, stereoisomer, or isotopic, conformational, or geometric isomer thereof.

11. The method of claim 1, wherein the compound is administered intraperitoneally.

12. The method of claim 1, wherein the compound is administered orally.

13. A method for treating diabetes comprising administering a therapeutically effective amount of a compound of formula (2):

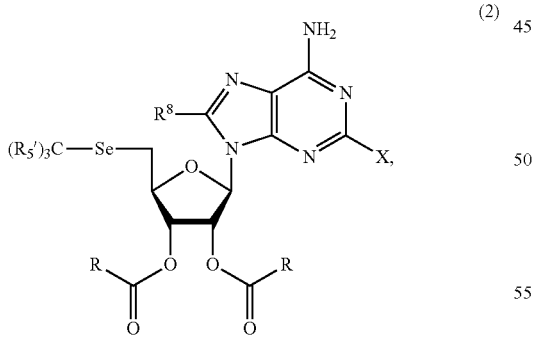

or a pharmaceutically acceptable salt, stereoisomer, or isotopic, conformational, or geometric isomer thereof, wherein:

$R^8$ is H or halogen;

X is H or halogen;

each $R_5'$ is independently H or halogen; and each R is independently $C_{1-6}$alkyl, each of which, independently, may optionally be substituted 1-3 times by halogen.

14. The method of claim 13, wherein the diabetes is type I diabetes or type II diabetes.

15. The method of claim 13, wherein the compound is of formula (2'):

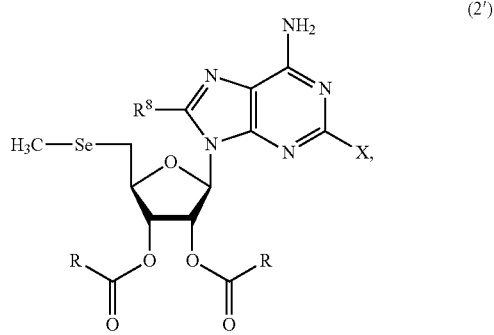

or a pharmaceutically acceptable salt, stereoisomer, or isotopic, conformational, or geometric isomer thereof.

16. The method of claim 13, wherein $R^8$ is H.

17. The method of claim 13, wherein X is H.

18. The method of claim 13, wherein each R is independently $C_{1-3}$alkyl, each of which, independently, may optionally be substituted 1-3 times by halogen.

19. The method of claim 13, wherein each R is independently unsubstituted $C_{1-3}$alkyl.

20. The method of claim 13, wherein the compound is of the formula:

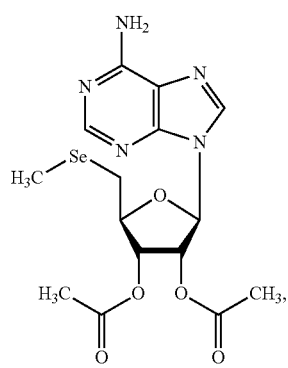

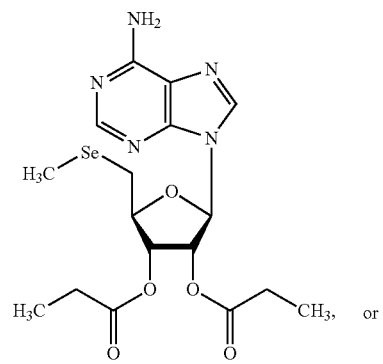

or

-continued

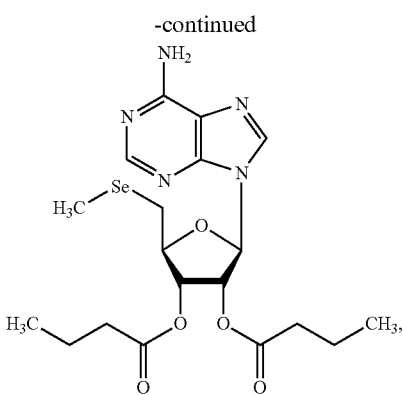

or a pharmaceutically acceptable salt, stereoisomer, or isotopic, conformational, or geometric isomer thereof.

21. The method of claim 20, wherein the compound is of the formula:

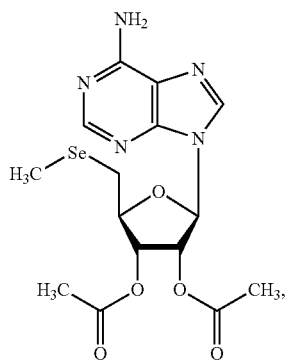

or a pharmaceutically acceptable salt, stereoisomer, or isotopic, conformational, or geometric isomer thereof.

22. A method for treating a degenerative disease selected from the group consisting of cardiovascular disease and cardiac failure, Alzheimer's disease, Parkinson's diseases, and sarcopenia, comprising administering a therapeutically effective amount of a compound of formula (2):

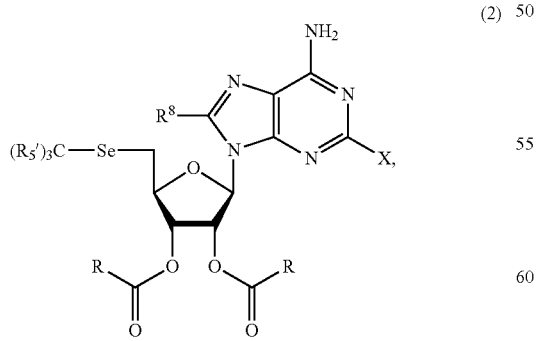

(2)

or a pharmaceutically acceptable salt, stereoisomer, or isotopic, conformational, or geometric isomer thereof, wherein:

$R^8$ is H or halogen;
X is H or halogen;
each $R_5'$ is independently H or halogen; and
each R is independently $C_{1-6}$alkyl, each of which, independently, may optionally be substituted 1-3 times by halogen.

23. The method of claim 22, wherein the compound is of formula (2'):

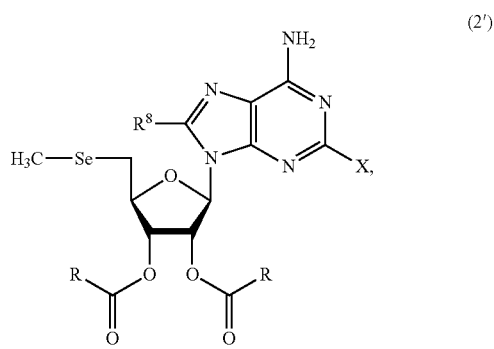

(2')

or a pharmaceutically acceptable salt, stereoisomer, or isotopic, conformational, or geometric isomer thereof.

24. The method of claim 22, wherein $R^8$ is H.

25. The method of claim 22, wherein X is H.

26. The method of claim 22, wherein each R is independently $C_{1-3}$alkyl, each of which, independently, may optionally be substituted 1-3 times by halogen.

27. The method of claim 22, wherein each R is independently unsubstituted $C_{1-3}$alkyl.

28. The method of claim 22, wherein the compound is of the formula:

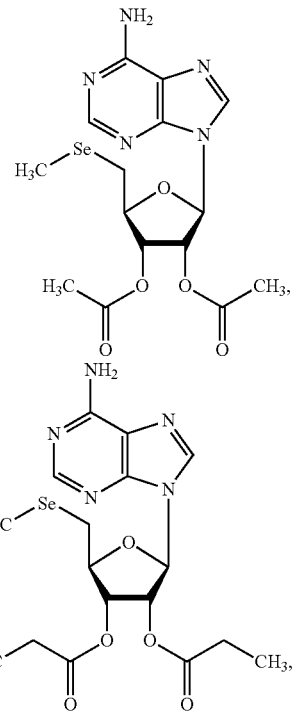

or

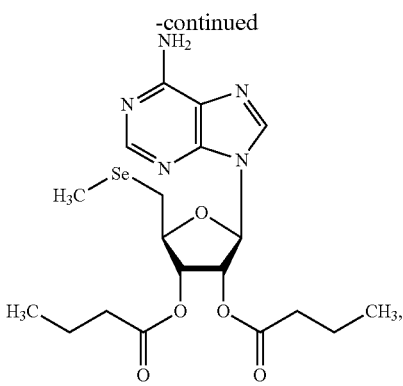

or a pharmaceutically acceptable salt, stereoisomer, or isotopic, conformational, or geometric isomer thereof.

29. The method of claim 28, wherein the compound is of the formula:

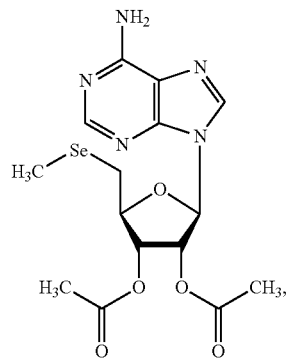

or a pharmaceutically acceptable salt, stereoisomer, or isotopic, conformational, or geometric isomer thereof.

30. A method of preparing a compound of formula (I):

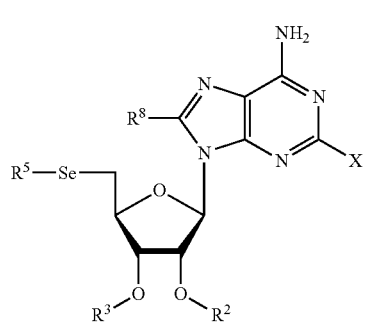
(I)

or a salt thereof,
comprising treating a compound of formula:

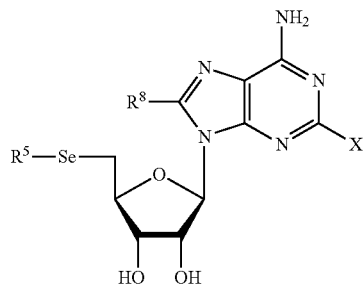

or a salt thereof,
with an agent selected from the group consisting of $(C_{1-6}alkylC(O))_2O$ and 1,1'-carbonyldiimidazole (CDI); or treating a compound of formula:

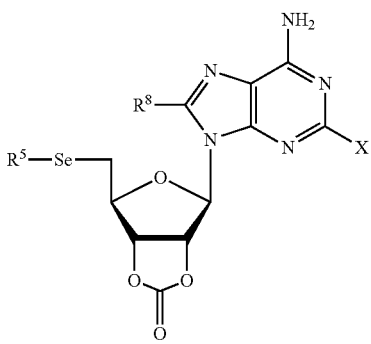

or a salt thereof,
with morpholine;
wherein:
each of $R^2$ and $R^3$ is independently H or —C(O)—R, wherein each R is independently $C_{1-6}$alkyl or 3-8 membered carbocyclic or heterocyclic, wherein $R^2$ and $R^3$ cannot be both H;
or $R^2$ together with $R^3$ form —$(CH_2)_n$—C(O)—$(CH_2)_m$—, wherein each of n and m is independently 0-3, and n+m≤3;
$R^5$ is —$C_{1-6}$alkyl or —$C_{1-6}$alkyl-CH(NH$_2$)COOH;
$R^8$ is H or halogen; and
X is H or halogen,
wherein each of the carbocyclic, heterocyclic, —$(CH_2)_n$—, and —$(CH_2)_m$— moieties, independently, may optionally be substituted 1-3 times by —OH, halogen, NH$_2$, CN, or $C_{1-6}$alkyl; and
each $C_{1-6}$alkyl moiety, independently, may optionally be substituted 1-3 times by —OH, halogen, NH$_2$, or CN.

31. A method of preparing a pharmaceutical composition comprising a compound of formula (1):

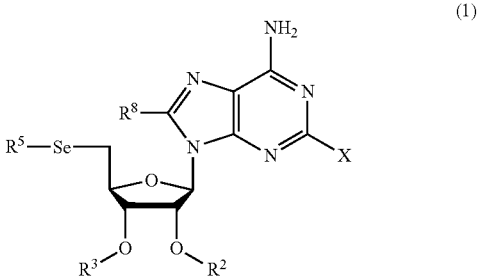
(1)

or a pharmaceutically acceptable salt, ester, stereoisomer, or isotopic, conformational, or geometric isomer thereof, wherein:
each of $R^2$ and $R^3$ is independently H or —C(O)—R, wherein each R is independently a $C_{1-6}$ alkyl or a 3-8 membered carbocyclic or heterocyclic, wherein $R^2$ and $R^3$ cannot be both H;
or $R^2$ together with $R^3$ form —$(CH_2)_n$—C(O)—$(CH_2)_m$—, wherein each of n and m is independently 0-3, and n+m≤3;
$R^5$ is —$C_{1-6}$alkyl or —$C_{1-6}$alkyl-CH(NH$_2$)COOH;
$R^8$ is H or halogen; and
X is H or halogen,
wherein each of the carbocyclic, heterocyclic, —$(CH_2)_n$—, and —$(CH_2)_m$— moieties, independently, may optionally be substituted 1-3 times by —OH, halogen, NH$_2$, CN, or $C_{1-6}$alkyl; and each $C_{1-6}$alkyl moiety, independently, may optionally be substituted 1-3 times by —OH, halogen, $NH_2$, or CN, the method comprising bringing into association the compound, or a pharmaceutically acceptable salt, ester, stereoisomer, or isotopic, conformational, or geometric isomer thereof, with one or more pharmaceutically acceptable carriers or excipients, and optionally one or more accessory ingredients.

\* \* \* \* \*